United States Patent
de Juan, Jr. et al.

(10) Patent No.: US 10,874,548 B2
(45) Date of Patent: Dec. 29, 2020

(54) THERAPEUTIC AGENT FORMULATIONS FOR IMPLANTED DEVICES

(71) Applicant: ForSight Vision4, Inc., Menlo Park, CA (US)

(72) Inventors: Eugene de Juan, Jr., Menlo Park, CA (US); Yair Alster, Menlo Park, CA (US); Steven M. Chamow, Menlo Park, CA (US); Kathleen Cogan Farinas, Menlo Park, CA (US); K. Angela Macfarlane, Menlo Park, CA (US); Cary J. Reich, Menlo Park, CA (US); Randolph E. Campbell, Menlo Park, CA (US); Signe Erickson, Menlo Park, CA (US); Blaine Bueche, Menlo Park, CA (US)

(73) Assignee: ForSight Vision4, Inc., Menlo Park, CA (US)

( * ) Notice: Subject to any disclaimer, the term of this patent is extended or adjusted under 35 U.S.C. 154(b) by 722 days.

(21) Appl. No.: 15/606,647

(22) Filed: May 26, 2017

(65) Prior Publication Data

US 2017/0258634 A1    Sep. 14, 2017

Related U.S. Application Data

(63) Continuation of application No. 13/988,298, filed as application No. PCT/US2011/061535 on Nov. 18, 2011, now abandoned.
(Continued)

(51) Int. Cl.
| | |
|---|---|
| *A61F 9/00* | (2006.01) |
| *A61P 27/02* | (2006.01) |

(Continued)

(52) U.S. Cl.
CPC ......... *A61F 9/0017* (2013.01); *A61K 9/0051* (2013.01); *A61K 9/1647* (2013.01); *A61K 9/1652* (2013.01); *A61K 31/573* (2013.01)

(58) Field of Classification Search
CPC .. A61K 9/0051; A61K 9/1647; A61K 9/1652; A61K 31/573; A61F 9/0017
(Continued)

(56) References Cited

U.S. PATENT DOCUMENTS

| | | |
|---|---|---|
| 2,564,977 A | 8/1951 | Hu et al. |
| 2,585,815 A | 2/1952 | McLintock |

(Continued)

FOREIGN PATENT DOCUMENTS

| | | |
|---|---|---|
| CN | 101327356 A | 12/2008 |
| CN | 101600476 A | 12/2009 |

(Continued)

OTHER PUBLICATIONS

".Beta.-Cyclodextrin, Sulfobutyl Ethers, Sodium Salts." ChemicalBook. Web. Jan. 24, 2016. 1 page. <http://www.chemicalbook.com/ChemicalProductProperty_EN_CB41208906.htm>.
(Continued)

*Primary Examiner* — Andrew J Mensh
(74) *Attorney, Agent, or Firm* — Mintz, Levin, Cohn, Ferris, Glovsky and Popeo, P.C.

(57) ABSTRACT

An injectable formulation of therapeutic agent may comprise the therapeutic agent and a stabilizer such that a substantial portion of the stabilizer remains in the therapeutic device to stabilize the therapeutic agent when the therapeutic agent is released from the therapeutic device. The injectable formulation may comprise one or more of binding agent particles or erodible material particles, such that the formulation can be injected into the therapeutic device. The binding agent particles can bind reversibly to the therapeutic
(Continued)

agent so as to modulate release of the therapeutic agent, and the erodible material particles can generate protons of an acid so as to increase stability of the therapeutic agent and may modulate release of the therapeutic agent. The therapeutic agent can be combined with one or more of the stabilizer, the binding agent particles or the erodible particles to increase stability of the therapeutic agent and may modulate release.

16 Claims, 23 Drawing Sheets

Related U.S. Application Data

(60) Provisional application No. 61/415,674, filed on Nov. 19, 2010.

(51) Int. Cl.
*A61K 9/00* (2006.01)
*A61K 9/16* (2006.01)
*A61K 31/573* (2006.01)

(58) Field of Classification Search
USPC .......................................... 604/20, 294, 298
See application file for complete search history.

(56) References Cited

U.S. PATENT DOCUMENTS

| | | |
|---|---|---|
| 2,886,497 A | 5/1959 | Butler |
| 3,232,117 A | 2/1966 | Gilmont |
| 3,416,530 A | 12/1968 | Ness |
| 3,618,604 A | 11/1971 | Ness |
| 3,641,237 A | 2/1972 | Gould et al. |
| 3,828,777 A | 8/1974 | Ness |
| 3,831,583 A | 8/1974 | Edmunds, Jr. et al. |
| 3,845,201 A | 10/1974 | Haddad et al. |
| 3,902,495 A | 9/1975 | Weiss et al. |
| 3,914,402 A | 10/1975 | Shell |
| 3,916,899 A | 11/1975 | Theeuwes et al. |
| 3,926,188 A | 12/1975 | Baker et al. |
| 3,949,748 A | 4/1976 | Malmin |
| 3,949,750 A | 4/1976 | Freeman |
| 3,961,628 A | 6/1976 | Arnold |
| 3,977,404 A | 8/1976 | Theeuwes |
| 3,995,635 A | 12/1976 | Higuchi et al. |
| 4,008,719 A | 2/1977 | Theeuwes et al. |
| 4,014,333 A | 3/1977 | McIntyre |
| 4,014,334 A | 3/1977 | Theeuwes et al. |
| 4,014,335 A | 3/1977 | Arnold |
| 4,034,756 A | 7/1977 | Higuchi et al. |
| 4,034,758 A | 7/1977 | Theeuwes |
| 4,077,407 A | 3/1978 | Theeuwes et al. |
| 4,111,201 A | 9/1978 | Theeuwes |
| 4,111,203 A | 9/1978 | Theeuwes |
| 4,135,514 A | 1/1979 | Zaffaroni et al. |
| 4,160,452 A | 7/1979 | Theeuwes |
| 4,164,559 A | 8/1979 | Miyata et al. |
| 4,179,497 A | 12/1979 | Cohen et al. |
| 4,186,184 A | 1/1980 | Zaffaroni |
| 4,200,098 A | 4/1980 | Ayer et al. |
| 4,220,152 A | 9/1980 | Dresback |
| 4,220,153 A | 9/1980 | Dresback |
| 4,256,108 A | 3/1981 | Theeuwes |
| 4,298,000 A | 11/1981 | Thill et al. |
| 4,300,557 A | 11/1981 | Refojo et al. |
| 4,309,776 A | 1/1982 | Berguer |
| 4,326,525 A | 4/1982 | Swanson et al. |
| 4,327,725 A | 5/1982 | Cortese et al. |
| 4,343,787 A | 8/1982 | Katz |
| 4,439,196 A | 3/1984 | Higuchi |
| 4,439,198 A | 3/1984 | Brightman, II et al. |
| 4,475,916 A | 10/1984 | Himmelstein |
| 4,484,922 A | 11/1984 | Rosenwald |
| 4,519,801 A | 5/1985 | Edgren |
| 4,609,374 A | 9/1986 | Ayer |
| 4,627,850 A | 12/1986 | Deters et al. |
| 4,634,418 A | 1/1987 | Binder |
| 4,634,427 A | 1/1987 | Hannula et al. |
| 4,673,405 A | 6/1987 | Guittard et al. |
| 4,693,886 A | 9/1987 | Ayer |
| 4,712,550 A | 12/1987 | Sinnett |
| 4,730,013 A | 3/1988 | Bondi et al. |
| 4,737,150 A | 4/1988 | Baeumle et al. |
| 4,774,091 A | 9/1988 | Yamahira et al. |
| 4,777,049 A | 10/1988 | Magruder et al. |
| 4,781,675 A | 11/1988 | White |
| 4,851,228 A | 7/1989 | Zentner et al. |
| 4,853,229 A | 8/1989 | Theeuwes |
| 4,863,457 A | 9/1989 | Lee |
| 4,865,846 A | 9/1989 | Kaufman |
| 4,883,459 A | 11/1989 | Calderon |
| 4,959,217 A | 9/1990 | Sanders et al. |
| 4,979,938 A | 12/1990 | Stephen et al. |
| 5,049,142 A | 9/1991 | Herrick et al. |
| 5,053,030 A | 10/1991 | Herrick et al. |
| 5,084,021 A | 1/1992 | Baldwin |
| 5,098,443 A | 3/1992 | Parel et al. |
| 5,128,145 A | 7/1992 | Edgren et al. |
| 5,141,748 A | 8/1992 | Rizzo |
| 5,147,647 A | 9/1992 | Darougar |
| 5,164,188 A | 11/1992 | Wong |
| 5,171,270 A | 12/1992 | Herrick |
| 5,174,999 A | 12/1992 | Magruder et al. |
| 5,238,687 A | 8/1993 | Magruder et al. |
| 5,277,912 A | 1/1994 | Lowe et al. |
| 5,282,829 A | 2/1994 | Hermes |
| 5,300,114 A | 4/1994 | Gwon et al. |
| 5,322,691 A | 6/1994 | Darougar et al. |
| 5,334,189 A | 8/1994 | Wade |
| 5,336,175 A | 8/1994 | Mames |
| 5,378,475 A | 1/1995 | Smith et al. |
| 5,413,572 A | 5/1995 | Wong et al. |
| 5,443,505 A | 8/1995 | Wong et al. |
| 5,466,233 A | 11/1995 | Weiner et al. |
| 5,476,511 A | 12/1995 | Gwon et al. |
| 5,519,030 A | 5/1996 | Shigemitsu et al. |
| 5,554,132 A | 9/1996 | Straits et al. |
| 5,562,915 A | 10/1996 | Lowe et al. |
| 5,578,042 A | 11/1996 | Cumming |
| 5,681,572 A | 10/1997 | Seare, Jr. |
| 5,725,493 A | 3/1998 | Avery et al. |
| 5,766,242 A | 6/1998 | Wong et al. |
| 5,770,076 A | 6/1998 | Chu et al. |
| 5,773,019 A | 6/1998 | Ashton et al. |
| 5,797,898 A | 8/1998 | Santini, Jr. et al. |
| 5,807,581 A | 9/1998 | Rosenblatt et al. |
| 5,824,072 A | 10/1998 | Wong |
| 5,830,173 A | 11/1998 | Avery et al. |
| 5,830,546 A | 11/1998 | Ehret et al. |
| 5,836,935 A | 11/1998 | Ashton et al. |
| 5,868,697 A | 2/1999 | Richter et al. |
| 5,902,598 A | 5/1999 | Chen et al. |
| 5,916,584 A | 6/1999 | O'Donoghue et al. |
| 5,928,662 A | 7/1999 | Phillips |
| 5,951,512 A | 9/1999 | Dalton |
| 5,968,008 A | 10/1999 | Grams |
| 5,972,369 A | 10/1999 | Roorda et al. |
| 5,985,328 A | 11/1999 | Chu et al. |
| 6,001,386 A | 12/1999 | Ashton et al. |
| 6,123,861 A | 9/2000 | Santini, Jr. et al. |
| 6,196,993 B1 | 3/2001 | Cohan et al. |
| 6,251,090 B1 | 6/2001 | Avery et al. |
| 6,303,290 B1 | 10/2001 | Liu et al. |
| 6,331,313 B1 | 12/2001 | Wong et al. |
| 6,331,523 B1 | 12/2001 | Kljavin et al. |
| 6,375,972 B1 | 4/2002 | Guo et al. |
| 6,395,300 B1 | 5/2002 | Straub et al. |
| 6,413,540 B1 | 7/2002 | Yaacobi |
| 6,416,777 B1 | 7/2002 | Yaacobi |
| 6,420,399 B1 | 7/2002 | Graff et al. |
| 6,472,162 B1 | 10/2002 | Coelho et al. |

(56) References Cited

U.S. PATENT DOCUMENTS

| | | |
|---|---|---|
| 6,534,524 B1 | 3/2003 | Kania et al. |
| 6,551,291 B1 | 4/2003 | de Juan, Jr. et al. |
| 6,573,293 B2 | 6/2003 | Tang et al. |
| 6,605,066 B1 | 8/2003 | Gravagna et al. |
| 6,663,668 B1 | 12/2003 | Chaouk et al. |
| 6,669,950 B2 | 12/2003 | Yaacobi |
| 6,685,940 B2 | 2/2004 | Andya et al. |
| 6,713,081 B2 | 3/2004 | Robinson et al. |
| 6,719,750 B2 | 4/2004 | Varner et al. |
| 6,740,077 B1 | 5/2004 | Brandau et al. |
| 6,756,049 B2 | 6/2004 | Brubaker et al. |
| 6,756,058 B2 | 6/2004 | Brubaker et al. |
| 6,878,714 B2 | 4/2005 | Askew et al. |
| 6,932,983 B1 | 8/2005 | Straub et al. |
| 6,976,982 B2 | 12/2005 | Santini, Jr. et al. |
| 6,986,900 B2 | 1/2006 | Yaacobi |
| 6,995,162 B2 | 2/2006 | Chen et al. |
| 7,026,329 B2 | 4/2006 | Crain et al. |
| 7,074,426 B2 | 7/2006 | Kochinke |
| 7,077,848 B1 | 7/2006 | de Juan, Jr. et al. |
| 7,090,681 B2 | 8/2006 | Weber et al. |
| 7,094,222 B1 | 8/2006 | Siekas et al. |
| 7,094,226 B2 | 8/2006 | Yaacobi |
| 7,105,530 B2 | 9/2006 | Boloor et al. |
| 7,117,870 B2 | 10/2006 | Prescott |
| 7,125,905 B2 | 10/2006 | Tang et al. |
| 7,141,023 B2 | 11/2006 | Diermann et al. |
| 7,141,152 B2 | 11/2006 | Le Febre |
| 7,141,581 B2 | 11/2006 | Bender et al. |
| 7,181,287 B2 | 2/2007 | Greenberg |
| 7,195,774 B2 | 3/2007 | Carvalho et al. |
| 7,195,778 B2 | 3/2007 | Fleshner-Barak et al. |
| 7,211,272 B2 | 5/2007 | Renner et al. |
| 7,211,600 B2 | 5/2007 | Lipson et al. |
| 7,235,576 B1 | 6/2007 | Riedl et al. |
| 7,262,203 B2 | 8/2007 | Boloor et al. |
| 7,276,050 B2 | 10/2007 | Franklin |
| 7,297,709 B2 | 11/2007 | Dai et al. |
| 7,351,834 B1 | 4/2008 | Riedl et al. |
| 7,452,913 B2 | 11/2008 | Sun et al. |
| 7,468,065 B2 | 12/2008 | Weber et al. |
| 7,476,510 B2 | 1/2009 | Kapur et al. |
| 7,528,255 B2 | 5/2009 | Riedl et al. |
| 7,572,924 B2 | 8/2009 | Tang et al. |
| 7,585,517 B2 | 9/2009 | Cooper et al. |
| 7,615,141 B2 | 11/2009 | Schwartz et al. |
| 7,621,907 B2 | 11/2009 | Rodstrom |
| 7,625,927 B2 | 12/2009 | Klimko et al. |
| 7,678,078 B1 | 3/2010 | Peyman et al. |
| 7,686,016 B2 | 3/2010 | Wharton et al. |
| 7,687,643 B2 | 3/2010 | Tasker et al. |
| 7,709,049 B2 | 5/2010 | Chappa |
| 7,772,404 B2 | 8/2010 | Borchardt et al. |
| 7,883,717 B2 | 2/2011 | Varner et al. |
| 7,893,040 B2 | 2/2011 | Loftsson et al. |
| 7,897,623 B2 | 3/2011 | Riedl et al. |
| 7,906,136 B2 | 3/2011 | Wong et al. |
| 7,909,800 B2 | 3/2011 | Cazzini |
| 7,914,442 B1 | 3/2011 | Gazdzinski |
| 7,939,094 B2 | 5/2011 | Schwarz et al. |
| 7,943,782 B2 | 5/2011 | Henry |
| 7,960,564 B2 | 6/2011 | Borchardt et al. |
| 7,973,068 B2 | 7/2011 | Demopulos et al. |
| 7,989,631 B2 | 8/2011 | Alva et al. |
| 8,058,445 B2 | 11/2011 | Tasker |
| 8,063,091 B2 | 11/2011 | Dai et al. |
| 8,114,885 B2 | 2/2012 | Boloor et al. |
| 8,211,830 B2 | 7/2012 | Bailey et al. |
| 8,277,830 B2 | 10/2012 | de Juan, Jr. et al. |
| 2002/0026176 A1 | 2/2002 | Varner et al. |
| 2002/0086051 A1 | 7/2002 | Viscasillas |
| 2002/0106395 A1 | 8/2002 | Brubaker |
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2003/0003129 A1 | 1/2003 | Yaacobi |
| 2003/0005945 A1 | 1/2003 | Onishi et al. |
| 2003/0014036 A1 | 1/2003 | Varner et al. |
| 2003/0118649 A1 | 6/2003 | Gao et al. |
| 2003/0119177 A1 | 6/2003 | Gruber et al. |
| 2003/0176854 A1 | 9/2003 | Rodstrom |
| 2003/0185872 A1 | 10/2003 | Kochinke |
| 2003/0212383 A1 | 11/2003 | Cote et al. |
| 2003/0235603 A1 | 12/2003 | Schwarz et al. |
| 2004/0011651 A1 | 1/2004 | Becker et al. |
| 2004/0019325 A1 | 1/2004 | Shekalim |
| 2004/0024371 A1 | 2/2004 | Plicchi et al. |
| 2004/0029832 A1 | 2/2004 | Zeldis |
| 2004/0092911 A1 | 5/2004 | Yaacobi |
| 2004/0106906 A1 | 6/2004 | Yaacobi |
| 2004/0131654 A1 | 7/2004 | Yaacobi |
| 2004/0131655 A1 | 7/2004 | Yaacobi |
| 2004/0171997 A1 | 9/2004 | Wilson et al. |
| 2004/0208910 A1 | 10/2004 | Ashton et al. |
| 2004/0209359 A1 | 10/2004 | Yayon et al. |
| 2004/0230183 A1 | 11/2004 | Breegi et al. |
| 2004/0247487 A1 | 12/2004 | Commercon et al. |
| 2004/0260380 A1 | 12/2004 | Marco et al. |
| 2004/0260381 A1 | 12/2004 | Marco et al. |
| 2005/0064010 A1 | 3/2005 | Cooper et al. |
| 2005/0074497 A1 | 4/2005 | Schultz |
| 2005/0112175 A1 | 5/2005 | Yaacobi |
| 2005/0112759 A1 | 5/2005 | Radisic et al. |
| 2005/0113806 A1 | 5/2005 | De Carvalho et al. |
| 2005/0119737 A1 | 6/2005 | Bene et al. |
| 2005/0143363 A1 | 6/2005 | De Juan et al. |
| 2005/0154399 A1 | 7/2005 | Weber et al. |
| 2005/0163711 A1 | 7/2005 | Nycz et al. |
| 2005/0181018 A1 | 8/2005 | Peyman |
| 2005/0244467 A1 | 11/2005 | Nivaggioli et al. |
| 2005/0244469 A1 | 11/2005 | Whitcup et al. |
| 2005/0244472 A1 | 11/2005 | Hughes et al. |
| 2005/0255144 A1 | 11/2005 | Schultz |
| 2005/0256499 A1 | 11/2005 | Pettis et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0277802 A1 | 12/2005 | Larsen et al. |
| 2005/0281861 A1 | 12/2005 | Hughes et al. |
| 2005/0281863 A1 | 12/2005 | Anderson et al. |
| 2005/0287188 A1 | 12/2005 | Anderson et al. |
| 2006/0013835 A1 | 1/2006 | Anderson et al. |
| 2006/0039952 A1 | 2/2006 | Yaacobi |
| 2006/0052754 A1 | 3/2006 | Fields |
| 2006/0057277 A1 | 3/2006 | Chappa |
| 2006/0073182 A1 | 4/2006 | Wong et al. |
| 2006/0104969 A1 | 5/2006 | Oray et al. |
| 2006/0110428 A1 | 5/2006 | deJuan et al. |
| 2006/0129215 A1 | 6/2006 | Helmus et al. |
| 2006/0154981 A1 | 7/2006 | Klimko et al. |
| 2006/0172941 A1 | 8/2006 | Rastelli et al. |
| 2006/0182783 A1 | 8/2006 | Hughes et al. |
| 2006/0189608 A1 | 8/2006 | Bingaman |
| 2006/0200097 A1 | 9/2006 | Humayun et al. |
| 2006/0233858 A1 | 10/2006 | Tzekov et al. |
| 2006/0246112 A1 | 11/2006 | Snyder et al. |
| 2006/0257450 A1 | 11/2006 | Mudumba et al. |
| 2006/0258000 A1 | 11/2006 | Allen et al. |
| 2006/0258994 A1 | 11/2006 | Avery |
| 2007/0020336 A1 | 1/2007 | Loftsson et al. |
| 2007/0021357 A1 | 1/2007 | Tobia et al. |
| 2007/0026037 A1 | 2/2007 | Kloke et al. |
| 2007/0059336 A1 | 3/2007 | Hughes et al. |
| 2007/0071756 A1 | 3/2007 | Peyman |
| 2007/0072933 A1 | 3/2007 | Peyman |
| 2007/0077270 A1 | 4/2007 | Wen |
| 2007/0078359 A1 | 4/2007 | Luloh et al. |
| 2007/0088414 A1 | 4/2007 | Campbell et al. |
| 2007/0119450 A1 | 5/2007 | Wharton et al. |
| 2007/0128644 A1 | 6/2007 | Munenaka |
| 2007/0131610 A1 | 6/2007 | Peng et al. |
| 2007/0131611 A1 | 6/2007 | Peng et al. |
| 2007/0134305 A1 | 6/2007 | Zilberman |
| 2007/0141111 A1 | 6/2007 | Suokas et al. |

(56) References Cited

U.S. PATENT DOCUMENTS

| | | |
|---|---|---|
| 2007/0191863 A1 | 8/2007 | De Juan et al. |
| 2007/0197491 A1 | 8/2007 | Robin et al. |
| 2007/0203174 A1 | 8/2007 | Klimko et al. |
| 2007/0212388 A1 | 9/2007 | Patravale et al. |
| 2007/0212397 A1 | 9/2007 | Roth |
| 2007/0219632 A1 | 9/2007 | Castillejos |
| 2007/0233037 A1 | 10/2007 | Gifford et al. |
| 2007/0235331 A1 | 10/2007 | Simpson et al. |
| 2007/0243230 A1 | 10/2007 | de Juan et al. |
| 2007/0260201 A1 | 11/2007 | Prausnitz et al. |
| 2007/0265599 A1 | 11/2007 | Castillejos |
| 2007/0269487 A1 | 11/2007 | de Juan et al. |
| 2008/0003219 A1 | 1/2008 | Peyman |
| 2008/0004329 A1 | 1/2008 | Jamieson et al. |
| 2008/0015545 A1 | 1/2008 | Sanchez et al. |
| 2008/0020045 A1 | 1/2008 | Chappa et al. |
| 2008/0038316 A1 | 2/2008 | Wong et al. |
| 2008/0057561 A1 | 3/2008 | Takahashi et al. |
| 2008/0066739 A1 | 3/2008 | LeMahieu et al. |
| 2008/0066741 A1 | 3/2008 | LeMahieu et al. |
| 2008/0069854 A1 | 3/2008 | Xiao et al. |
| 2008/0089923 A1 | 4/2008 | Burkstrand et al. |
| 2008/0111282 A1 | 5/2008 | Xie et al. |
| 2008/0124372 A1 | 5/2008 | Hossainy et al. |
| 2008/0139674 A1 | 6/2008 | Archambeau et al. |
| 2008/0145406 A1 | 6/2008 | Asgharian et al. |
| 2008/0146679 A1 | 6/2008 | Archambeau et al. |
| 2008/0147021 A1 | 6/2008 | Jani |
| 2008/0152694 A1 | 6/2008 | Lobl et al. |
| 2008/0154241 A1 | 6/2008 | Burkstrand et al. |
| 2008/0161741 A1 | 7/2008 | Bene et al. |
| 2008/0167600 A1 | 7/2008 | Peyman |
| 2008/0172014 A1 | 7/2008 | Whitcup et al. |
| 2008/0181930 A1 | 7/2008 | Rodstrom et al. |
| 2008/0195218 A1 | 8/2008 | Jones |
| 2008/0207502 A1 | 8/2008 | Rastelli et al. |
| 2008/0213611 A1 | 9/2008 | Asgari |
| 2008/0216736 A1 | 9/2008 | David |
| 2008/0228127 A1 | 9/2008 | Burns et al. |
| 2008/0233053 A1 | 9/2008 | Gross et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0241219 A1 | 10/2008 | Whitcup et al. |
| 2008/0241220 A1 | 10/2008 | Whitcup et al. |
| 2008/0241221 A1 | 10/2008 | Whitcup et al. |
| 2008/0241222 A1 | 10/2008 | Whitcup et al. |
| 2008/0241223 A1 | 10/2008 | Nivaggioli et al. |
| 2008/0249501 A1 | 10/2008 | Yamasaki |
| 2008/0269318 A1 | 10/2008 | Romano |
| 2008/0286338 A1 | 11/2008 | Rosenthal et al. |
| 2008/0292679 A1 | 11/2008 | Lyons et al. |
| 2008/0293691 A1 | 11/2008 | Brigandi et al. |
| 2009/0005864 A1 | 1/2009 | Eggleston |
| 2009/0012485 A1 | 1/2009 | Michaels et al. |
| 2009/0036827 A1 | 2/2009 | Cazzini |
| 2009/0043253 A1 | 2/2009 | Podaima |
| 2009/0047335 A1 | 2/2009 | Rastelli et al. |
| 2009/0074786 A1* | 3/2009 | Dor .................. A61P 27/02 424/141.1 |
| 2009/0081271 A1 | 3/2009 | Clarke et al. |
| 2009/0081272 A1 | 3/2009 | Clarke et al. |
| 2009/0082631 A1 | 3/2009 | Cronin et al. |
| 2009/0087494 A1 | 4/2009 | Kompella et al. |
| 2009/0092654 A1 | 4/2009 | de Juan, Jr. et al. |
| 2009/0093752 A1 | 4/2009 | Richard et al. |
| 2009/0099626 A1 | 4/2009 | de Juan, Jr. et al. |
| 2009/0104243 A1 | 4/2009 | Utkhede et al. |
| 2009/0105749 A1 | 4/2009 | de Juan et al. |
| 2009/0124997 A1 | 5/2009 | Pettis et al. |
| 2009/0192493 A1 | 7/2009 | Meng et al. |
| 2009/0196903 A1 | 8/2009 | Kliman |
| 2009/0214601 A1 | 8/2009 | Chappa et al. |
| 2009/0220572 A1 | 9/2009 | Deschatelets et al. |
| 2009/0224064 A1 | 9/2009 | Brodbeck et al. |
| 2009/0234449 A1 | 9/2009 | De Juan, Jr. et al. |
| 2009/0240208 A1 | 9/2009 | Cowan |
| 2009/0240215 A1 | 9/2009 | Humayun et al. |
| 2009/0247458 A1 | 10/2009 | Watson et al. |
| 2009/0258069 A1 | 10/2009 | Burnier et al. |
| 2009/0259212 A1 | 10/2009 | Sabbah |
| 2009/0263346 A1 | 10/2009 | Taft et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2009/0280470 A1 | 11/2009 | Fare et al. |
| 2009/0306025 A1 | 12/2009 | Lane |
| 2009/0306595 A1 | 12/2009 | Shih et al. |
| 2009/0318545 A1 | 12/2009 | Silver et al. |
| 2009/0324686 A1 | 12/2009 | Cooper et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2009/0326448 A1 | 12/2009 | Huo et al. |
| 2010/0003333 A1 | 1/2010 | Watson et al. |
| 2010/0004189 A1 | 1/2010 | Watson et al. |
| 2010/0008997 A1 | 1/2010 | Watson et al. |
| 2010/0009008 A1 | 1/2010 | Watson et al. |
| 2010/0010452 A1 | 1/2010 | Paques et al. |
| 2010/0011888 A1 | 1/2010 | Pawliszyn et al. |
| 2010/0015157 A1 | 1/2010 | Andya et al. |
| 2010/0015158 A1 | 1/2010 | Robinson et al. |
| 2010/0016786 A1 | 1/2010 | Drews et al. |
| 2010/0021464 A1 | 1/2010 | Archambeau et al. |
| 2010/0022943 A1 | 1/2010 | Mauch et al. |
| 2010/0022945 A1 | 1/2010 | Rodstrom |
| 2010/0023033 A1 | 1/2010 | Mauch et al. |
| 2010/0028442 A1 | 2/2010 | Archambeau et al. |
| 2010/0028443 A1 | 2/2010 | Watson et al. |
| 2010/0030136 A1 | 2/2010 | Dacquay et al. |
| 2010/0034870 A1 | 2/2010 | Sim et al. |
| 2010/0083963 A1 | 4/2010 | Wharton et al. |
| 2010/0100054 A1 | 4/2010 | Cormier et al. |
| 2010/0114017 A1 | 5/2010 | Lenker et al. |
| 2010/0114309 A1 | 5/2010 | de Juan, Jr. et al. |
| 2010/0158980 A1 | 6/2010 | Kopczynski et al. |
| 2010/0168535 A1 | 7/2010 | Robinson et al. |
| 2010/0174272 A1 | 7/2010 | Weiner |
| 2010/0185205 A1 | 7/2010 | Novakovic et al. |
| 2010/0189765 A1 | 7/2010 | Erickson et al. |
| 2010/0197512 A1 | 8/2010 | Trinkle et al. |
| 2010/0216702 A1 | 8/2010 | Szkudlinski et al. |
| 2010/0221309 A1 | 9/2010 | Myers et al. |
| 2010/0223979 A1 | 9/2010 | Ploehn et al. |
| 2010/0227904 A1 | 9/2010 | Kabra et al. |
| 2010/0255061 A1* | 10/2010 | de Juan, Jr. ......... A61F 9/0017 424/427 |
| 2010/0256597 A1 | 10/2010 | Prausnitz et al. |
| 2010/0266664 A1 | 10/2010 | Asgharian et al. |
| 2010/0286121 A1 | 11/2010 | Rohrs et al. |
| 2010/0286791 A1 | 11/2010 | Goldsmith |
| 2010/0297046 A1 | 11/2010 | Schwartz et al. |
| 2010/0297120 A1 | 11/2010 | Beliveau et al. |
| 2010/0297193 A1 | 11/2010 | Archambeau et al. |
| 2010/0303917 A1 | 12/2010 | Watson et al. |
| 2010/0303918 A1 | 12/2010 | Watson et al. |
| 2010/0310664 A1 | 12/2010 | Watson et al. |
| 2010/0310665 A1 | 12/2010 | Watson et al. |
| 2010/0316723 A1 | 12/2010 | Watson et al. |
| 2010/0330146 A1 | 12/2010 | Chauhan et al. |
| 2010/0331548 A1 | 12/2010 | Liu et al. |
| 2011/0009571 A1 | 1/2011 | Taft et al. |
| 2011/0014264 A1 | 1/2011 | Helmus et al. |
| 2011/0033933 A1 | 2/2011 | Gharib et al. |
| 2011/0034448 A1 | 2/2011 | Chang et al. |
| 2011/0081384 A1 | 4/2011 | Archambeau et al. |
| 2011/0098686 A1 | 4/2011 | Varner et al. |
| 2011/0104155 A1 | 5/2011 | Rekik |
| 2011/0108025 A1 | 5/2011 | Fink et al. |
| 2011/0111006 A1 | 5/2011 | Wong et al. |
| 2011/0112188 A1 | 5/2011 | Tobia et al. |
| 2011/0117083 A1 | 5/2011 | Bais et al. |
| 2011/0125178 A1 | 5/2011 | Drews et al. |

(56) References Cited

U.S. PATENT DOCUMENTS

| | | |
|---|---|---|
| 2011/0159073 A1 | 6/2011 | deJuan et al. |
| 2011/0190723 A1 | 8/2011 | Fangrow |
| 2011/0206646 A1 | 8/2011 | Alfonso et al. |
| 2011/0281901 A1 | 11/2011 | Gupta |
| 2012/0028918 A1 | 2/2012 | Gupta |
| 2012/0029445 A1 | 2/2012 | de Juan, Jr. et al. |
| 2012/0029470 A1 | 2/2012 | Juan, Jr. et al. |
| 2012/0040986 A1 | 2/2012 | Riedl et al. |
| 2013/0012531 A1 | 1/2013 | King et al. |
| 2013/0165860 A1 | 6/2013 | Doud et al. |
| 2013/0204209 A1 | 8/2013 | de Juan, Jr. et al. |
| 2013/0218081 A1 | 8/2013 | Roth |
| 2013/0245544 A1 | 9/2013 | de Juan, Jr. et al. |
| 2013/0245573 A1 | 9/2013 | de Juan, Jr. et al. |
| 2013/0274691 A1 | 10/2013 | de Juan, Jr. et al. |
| 2013/0274692 A1 | 10/2013 | Alster et al. |
| 2013/0304031 A1 | 11/2013 | Varner |
| 2013/0324918 A1 | 12/2013 | de Juan, Jr. et al. |
| 2013/0324942 A1 | 12/2013 | de Juan, Jr. et al. |
| 2014/0033800 A1 | 2/2014 | Farinas et al. |
| 2014/0073714 A1 | 3/2014 | Reich et al. |
| 2014/0121609 A1 | 5/2014 | de Juan, Jr. et al. |
| 2014/0221941 A1 | 8/2014 | Erickson et al. |
| 2014/0243795 A1 | 8/2014 | Varner et al. |
| 2014/0276482 A1 | 9/2014 | Astafieva et al. |
| 2014/0296800 A1 | 10/2014 | Erickson et al. |
| 2014/0358125 A1 | 12/2014 | de Juan, Jr. et al. |
| 2015/0080846 A1 | 3/2015 | de Juan, Jr. et al. |
| 2015/0250647 A1 | 9/2015 | de Juan, Jr. et al. |
| 2015/0297402 A1 | 10/2015 | de Juan, Jr. et al. |
| 2016/0101046 A1 | 4/2016 | Reich et al. |
| 2016/0184134 A1 | 6/2016 | Varner et al. |
| 2016/0258855 A1 | 9/2016 | Farinas et al. |
| 2017/0165110 A1 | 6/2017 | Erickson et al. |
| 2017/0172794 A1 | 6/2017 | Varner et al. |
| 2017/0258634 A1 | 9/2017 | de Juan, Jr. et al. |
| 2018/0161202 A1 | 6/2018 | de Juan, Jr. et al. |
| 2018/0243130 A1 | 8/2018 | Doud et al. |
| 2018/0243131 A1 | 8/2018 | Erickson et al. |
| 2018/0289542 A1 | 10/2018 | de Juan, Jr. et al. |
| 2018/0292403 A1 | 10/2018 | de Juan, Jr. et al. |
| 2019/0336335 A1 | 11/2019 | de Juan, Jr. et al. |
| 2020/0030142 A1 | 1/2020 | Erickson et al. |

FOREIGN PATENT DOCUMENTS

| | | |
|---|---|---|
| CN | 102365109 A | 2/2012 |
| EP | 0033042 B1 | 8/1984 |
| EP | 0 228 185 A1 | 11/1986 |
| EP | 0498471 A2 | 8/1992 |
| EP | 0500143 A2 | 8/1992 |
| EP | 0671165 A2 | 9/1995 |
| EP | 0295248 B2 | 4/1999 |
| EP | 0944658 B1 | 6/2003 |
| EP | 1671624 A1 | 6/2006 |
| EP | 1385452 | 9/2006 |
| EP | 1409065 | 1/2007 |
| EP | 1337284 B1 | 12/2007 |
| EP | 1911481 | 4/2008 |
| EP | 1521572 B1 | 3/2009 |
| JP | 01-149716 | 6/1989 |
| JP | 01-197429 A | 8/1989 |
| JP | 2001-518880 A | 10/2001 |
| JP | 2004-516889 A | 6/2004 |
| JP | 2004-524866 A | 8/2004 |
| JP | 2009-514888 A | 4/2009 |
| JP | 2009-523821 A | 6/2009 |
| JP | 2009-529968 A | 8/2009 |
| JP | 2010-521470 A | 6/2010 |
| WO | WO-88/04573 A1 | 6/1988 |
| WO | WO-90/07545 A2 | 7/1990 |
| WO | WO-95/28984 A1 | 11/1995 |
| WO | WO-97/29850 | 8/1997 |
| WO | WO-98/25982 | 6/1998 |
| WO | WO-98/43611 A1 | 10/1998 |
| WO | WO-99/11244 | 3/1999 |
| WO | WO-00/48660 | 8/2000 |
| WO | WO-01/26714 | 4/2001 |
| WO | WO-01/50943 | 7/2001 |
| WO | WO-01/68016 | 9/2001 |
| WO | WO-02/053128 A2 | 7/2002 |
| WO | WO-02/100318 | 12/2002 |
| WO | WO-03/028765 | 4/2003 |
| WO | WO-03/077972 | 9/2003 |
| WO | WO-03/082188 | 10/2003 |
| WO | WO-2004/000267 | 12/2003 |
| WO | WO-2004/112653 | 12/2004 |
| WO | WO-2005/016401 | 2/2005 |
| WO | WO-2005/027906 | 3/2005 |
| WO | WO-2005/028006 | 3/2005 |
| WO | WO-2005/091922 | 10/2005 |
| WO | WO-2005/107705 | 11/2005 |
| WO | WO-2005/110362 | 11/2005 |
| WO | WO-2005/110436 | 11/2005 |
| WO | WO-2005/110473 | 11/2005 |
| WO | WO-2005/117780 | 12/2005 |
| WO | WO-2006/014484 | 2/2006 |
| WO | WO-2006/015385 | 2/2006 |
| WO | WO-2006/023530 | 3/2006 |
| WO | WO-2006/031358 | 3/2006 |
| WO | WO-2006/031388 | 3/2006 |
| WO | WO-2006/044614 | 4/2006 |
| WO | WO-2006/050221 | 5/2006 |
| WO | WO-2006/068838 | 6/2006 |
| WO | WO-2006/071554 | 7/2006 |
| WO | WO-2006/082588 | 8/2006 |
| WO | WO-2006/108054 | 10/2006 |
| WO | WO-2006/127962 | 11/2006 |
| WO | WO-2006/138609 | 12/2006 |
| WO | WO-2007/012974 | 2/2007 |
| WO | WO-2007/035473 | 3/2007 |
| WO | WO-2007/035621 | 3/2007 |
| WO | WO-2007/038453 | 4/2007 |
| WO | WO-2007/044534 | 4/2007 |
| WO | WO-2007/047744 | 4/2007 |
| WO | WO-2007/064752 A2 | 6/2007 |
| WO | WO-2007/066339 | 6/2007 |
| WO | WO-2007/084582 | 7/2007 |
| WO | WO-2007/084765 | 7/2007 |
| WO | WO-2007/101204 | 9/2007 |
| WO | WO-2007/115259 A2 | 10/2007 |
| WO | WO-2007/117394 | 10/2007 |
| WO | WO-2007/131050 | 11/2007 |
| WO | WO-2007/133761 | 11/2007 |
| WO | WO-2007/133762 | 11/2007 |
| WO | WO-2008/003043 | 1/2008 |
| WO | WO-2008/005240 | 1/2008 |
| WO | WO-2008/011125 | 1/2008 |
| WO | WO-2008/019265 | 2/2008 |
| WO | WO-2008/033924 | 3/2008 |
| WO | WO-2008/040062 | 4/2008 |
| WO | WO-2008/045272 | 4/2008 |
| WO | WO-2008/052145 | 5/2008 |
| WO | WO-2008/060359 | 5/2008 |
| WO | WO-2008/061043 | 5/2008 |
| WO | WO-2008/076544 | 6/2008 |
| WO | WO-2008/094989 | 8/2008 |
| WO | WO-2008/115290 | 9/2008 |
| WO | WO-2008/116165 | 9/2008 |
| WO | WO-2008/144340 | 11/2008 |
| WO | WO-2008/144919 | 12/2008 |
| WO | WO-2009/012075 | 1/2009 |
| WO | WO-2009/023615 | 2/2009 |
| WO | WO-2009/046164 | 4/2009 |
| WO | WO-2009/055620 | 4/2009 |
| WO | WO-2009/055671 | 4/2009 |
| WO | WO-2009/055729 | 4/2009 |
| WO | WO-2009/055824 | 4/2009 |
| WO | WO-2009/061607 | 5/2009 |
| WO | WO-2009/073192 | 6/2009 |
| WO | WO-2009/086112 | 7/2009 |
| WO | WO-2009/089409 | 7/2009 |
| WO | WO-2009/094466 | 7/2009 |
| WO | WO-2009/112878 | 9/2009 |

(56) References Cited

FOREIGN PATENT DOCUMENTS

| | | |
|---|---|---|
| WO | WO-2009/117112 | 9/2009 |
| WO | WO-2009/124096 | 10/2009 |
| WO | WO-2009/128932 | 10/2009 |
| WO | WO-2009/134929 | 11/2009 |
| WO | WO-2009/137777 | 11/2009 |
| WO | WO-2009/143288 A1 | 11/2009 |
| WO | WO-2010/008424 | 1/2010 |
| WO | WO-2010/021993 | 2/2010 |
| WO | WO-2010/047753 | 4/2010 |
| WO | WO-2010/062628 | 6/2010 |
| WO | WO-2010/066714 | 6/2010 |
| WO | WO 2010//075565 | 7/2010 |
| WO | WO-2010/078063 | 7/2010 |
| WO | WO-2010/088548 | 8/2010 |
| WO | WO-2010/093945 | 8/2010 |
| WO | WO-2010/095940 | 8/2010 |
| WO | WO-2010/125416 | 11/2010 |
| WO | WO-2010/126908 | 11/2010 |
| WO | WO-2010/135369 | 11/2010 |
| WO | WO-2010/141729 | 12/2010 |
| WO | WO-2010/147661 | 12/2010 |
| WO | WO-2011/008896 | 1/2011 |
| WO | WO-2011/008897 | 1/2011 |
| WO | WO-2011/028850 | 3/2011 |
| WO | WO-2011/034627 | 3/2011 |
| WO | WO-2011/069053 A1 | 6/2011 |
| WO | WO-2011/0075481 A1 | 6/2011 |
| WO | WO-2011/079232 | 6/2011 |
| WO | WO-2011/140343 A1 | 11/2011 |
| WO | WO-2012/019047 A2 | 2/2012 |
| WO | WO-2012/019136 | 2/2012 |
| WO | WO-2012/042421 A1 | 4/2012 |
| WO | WO-2013/003620 | 1/2013 |
| WO | WO-2013/022801 | 2/2013 |
| WO | WO-2013/033176 A1 | 3/2013 |
| WO | WO-2013/151568 A1 | 10/2013 |
| WO | WO-2014/064652 A2 | 5/2014 |

OTHER PUBLICATIONS

"GrayBug." *GrayBug*. Web. Oct. 22, 2015. 1 page. www.graybug.com.

"Juvederm", Summary of Safety and Effectiveness Data. FDA, 2006, XP002670727, Retrieved from the Internet: URL:http://www.accessdata.fda.gov/cdrh_docs/pdf5/P050047b.pdf [retrieved on Mar. 1, 2012] p. 1, last paragraph.

"The Print® Technology Overview | Envisia." *Envisia*. Web. Oct. 22, 2015. 2 pages. http://www.envisiatherapeutics.com/print-overview/.

AMD Preclinical Studies. Anti-Factor D Fab Specifically Inhibits the Alternative Pathway. The Association for Research in Vision and Ophthalmology, Inc. 2010. p. 1.

Andrews, "Effect of nonsteroidal anti-inflammatory drugs on LFA-1 and ICAM-1 expression in gastric mucosa," Am J Physiol. Apr. 1994;266(4 Pt 1):G657-664.

Arakawa, Tsutomu, et. al. "Factors affecting short-term and long-term stabilities of proteins." Advanced Drug Delivery Reviews, vol. 10, No. 1, 1993, pp. 1-28.

Arvo, Agenda for the Summer Eye Research Conference, (Jul. 2009). 7 pages.

Avery et al., "Intravitreal bevacizumab (Avastin) in the treatment of proliferative diabetic retinopathy," Ophthalmology. Oct. 2006, 113(10):1695-1705.e6.

Bakri et al., "The effect of intravitreal triamcinolone acetonide on intraocular pressure," Ophthalmic Surgery, Lasers and Imaging, Sep./Oct. 2003; 34(5): 386-390.

Bird et al., Transport Phenomena, John Wiley & Sons, Inc., New York, 1960, pp. 196-201.

Black et al., Handbook of Biomaterial Properties, pp. 115 & 126, Chapman & Hall, 1998.

Block et al., "Solubility and dissolution of triamcinolone acetonide," Journal of Pharmaceutical Sciences,Apr. 1973; 62(4):617-621.

Breslin, C.W., et al., "Chapter 7. Slow Release Artificial Tears", *Symposium on Ocular Therapy* pp. 77-83, 1977.

Brewster and Loftsson, Advanced Drug Delivery Reviews, 59: 645-666 (2007).

Captisol® Cyclodextrins General. Captisol® FAQ Cyclodextrins General. Web. Jan. 24, 2016. 2 pages. <http://www.captisol.com/faq/cyclodextrins-general/>.

Castro et al., "Effect of COX inhibitors on VEGF-induced retinal vascular leakage and experimental corneal and choroidal neovascularization," Exp Eye Res. Aug. 2004;79(2):275-285.

Chirila et al., "The Vitreous Humor" in *Handbook of Biomaterial Properties*, eds. Black & Hastings. Chapman & Hall, London, 1998; pp. 125-131.

Cousins et al., "Program # 1251—Targeting Complement Factor 5 in Combination with Vascular Endothelial Growth Factor (VEGF) Inhibition for Neovascular Age Related Macular Degeneration (AMD): Results of a Phase 1 Study," [Presentation Abstract], AMD Clinical Trials Session # 220, May 3, 2010. 2 pages.

Deissler et al., "VEGF-induced effects on proliferation, migration and tight junctions are restored by ranibizumab (Lucentis) in microvascular retinal endothelial cells," Br J Ophthalmol 2008; 92:839-843.

Del Amo, et al., Current & future ophthalmic drug delivery systems . . . , *Drug Discovery Today*, vol. 13, Nos. 3/4, Feb. 2008. pp. 135-143.

Donoso et al., "The role of inflammation in the pathogenesis of age-related macular degeneration," Surv Ophthalmol. Mar.-Apr. 2006;51(2):137-52.

Duvvuri et al., Drug Delivery to the Retina: Challenges and Opportunities, *Expert Opinion on Biological Therapy*, 2003, vol. 3(1): 45-56.

European Medicine Agency, Scientific Discussion; retrieved from the Internet; <http://www.ema.europa.eu/docs/en_GB/document_library/EPAR_-Scientific_Discussion/human/000715/WC500043550.pdf>, EMEA 2007, 54 pages total. 2007.

Funatsu et al. "Association of vitreous inflammatory factors with diabetic macular edema," Ophthalmology 2009; 116:73-79.

Gaudana et al., Recent Perspectives in Ocular Drug Delivery, *Pharmaceutical Research*, 2008. 20 pages.

Gaudana R. et al., Ocular Therapeutic agent Delivery, AAPS J., 12(3): 348-360 (2010).

Gaudreault et al., "Preclinical Pharmacokinetics of Ranibizumab (rhuFabV2) after a Single Intravitreal Administration," Investigative Ophthalmology and Visual Science. 2005;46:726-733. Retrieved from the Internet: <<http://www.iovs.org/cgi/reprint/46/2/726>>.

Gillies et al., "Intravitreal triamcinolone for refractory diabetic macular edema: two-year results of a double-masked, placebo-controlled, randomized clinical trial," Ophthalmology. Sep. 2006;113(9):1533-1538.

Haller, An Overview of Sustained-release Drug Implants, Retinal Physician, Jan. 2008. 4 pages.

Hastedt & Wright, "Diffusion in porous materials above the percolation threshold," Pharm. Res. Sep. 1990; 7(9):893-901 (1990).

Heier et al, "Ketorolac versus prednisolone versus combination therapy in the treatment of acute pseudophakic cystoid macular edema," Ophthalmology. Nov. 2000;107(11):2034-2038 ;discussion 2039.

Iwase et al. "Sustained delivery of a HIF-1 antagonist for ocular neovascularization." Journal of Controlled Release. 172 (2013) 625-633.

Iwase et al.,Topical pazopanib blocks VEGF-induced vascular leakage and neovascularization in the mouse retina but is ineffective in the rabbit, Invest. Ophthalmol. Vis. Sci. (2013) 54(1):503-11.

Janoria et al., Novel Approaches to Retinal Drug Delivery, *Expert Opinion Drug Delivery*, (Jul. 2007) 4(4):371-388.

Jena et al., "A Novel Technique for Surface Area and Particle Size Determination of Components of Fuel Cells and Batteries," Porous Materials, Inc., Dec. 2006, 3 pages total. Downloaded from the Internet: <<http://www.pmiapp.com/publications/docs/A_Novel_technique_for_surface_area.pdf>>.

(56) References Cited

OTHER PUBLICATIONS

Kang et al., "Inhibitory effects of anti-inflammatory drugs on interleukin-6 bioactivity," Biol Pharm Bull. Jun. 2001, 24(6):701-703.
Katz, I.M., et al., "A Soluble Sustained-Release Ophthalmic Delivery Unit", 8:5 (May 1977) pp. 728-734.
Lamberts, D.W., M.D., et al., "A Clinical Study of Slow-Releasing Artificial Tears", *Ophthalmology* 85 (1978) pp. 794-800.
Lee, D.A., et al., "Glaucoma Filtration Surgery in Rabbits Using Bioerodible Polymers and 5-Fluorouracil", *Ophthalmology* 94:12 (1987) pp. 1523-1530.
Lee, D.A., et al., "The Use of Bioerodible Polymers and 5-Fluorouracil in Glaucoma Filtration Surgery", *Investigative Ophthalmology & Visual Science* 29-11 (1988) pp. 1692-1697.
Li, et al., An electrochemical introculardrug delivery device, *Science Direct, Sensors and Actuators*, www.sciencedirect.com, (2008) 41-48. Available online Jul. 4, 2007.
Lopez-Armada et al., "Modulation of cell recruitment by anti-inflammatory agents in antigen-induced arthritis," Ann Rheum Dis Nov. 2002;61(11):1027-1030.
Luncentis, Inn-Ranibizumab, "Scientific Discussion," European Medicines Agency ; retrieved from the Internet<http://www.ema.europa.eu/docs/en_GB/document_library/EPAR_-Assessment_Report_-_Variation/human/000715/WC500101009.pdf>. Oct. 21, 2010. 32 pages.
MAbPac Scx-10 Column for Monoclonal Antibody Variant Analysis, 2010. 4 pages. http://www.dionex.com/en-us/webdocs/87008-DS-MAbPac-SCX-10-Column-20Aug2010-LPN2567-03.pdf.
Merkel, Timothy J., et al. "The effect of particle size on the biodistribution of low-modulus hydrogel PRINT particles." *Journal of Controlled Release* 162.1 (2012): 37-44.
Metal Powder Industries Federation, Porous Metal Design Guidebook, 2007, 24 pages total. Downloaded from the Internet: <<http://www.mpif.org/DesignCenter/porous.pdf>>.
Miller, DP, et al., *Thermophysical Properties of Trehalose and Its Concentrated Aqueous Solutions*,Pharmaceutical Research, vol. 14, No. 5, 1997, pp. 578-590.
Molokhia et al, "Transscleral iontophoretic and intravitreal delivery of a macromolecule: Study of ocular distribution in vivo and postmortem with MRI", Experimental Eye Research 88 (2009) 418-425.
Moritera, T., et al., "Microspheres of Biodegradable Polymers as a Drug-Delivery System in the Vitreous", *Investigative Ophthalmology & Visual Science* 32-6 (1991) pp. 1785-1790.
Mott Corporation, "Sintered Metal Powder Media," American Filtration & Separation Society 2007, 2 pages total. Downloaded from the Internet:<<http://www.afssociety.org/education/0907oneminute.htm>>.
Navarro, "The Optical Design of the Human Eye: a Critical Review," J Optom, Jan.-Mar. 2009 2(1): 3-18.
Nutan, MTH, et al., *General Principles of Suspensions, in Pharmaceutical Suspensions Fron Formulation Development to Manufacturing*, editors AK Kulshreshtha, et al., Spinger, 2010. 29 pages.
Okabe et al., "Intraocular tissue distribution of betamethasone after intrascleral administration using a non-biodegradable sustained drug delivery device," Investigative Ophthalmology and Visual Science. 2003;44:2702-2707. Downloaded from the Internet: <<http://www.iovs.org/cgi/reprint/44/6/2702>>.
PCT International Search Report dated May 29, 2012, for PCT application No. PCT/US2011/061535.
Rosenfeld, "The Latest Research: Intravitreal Bevacizumab for Proliferative Diabetic Retinopathy," Review of Ophthalmology's Retina Online, Feb. 2006, 2 pages. Retrieved from the Internet: http://www.revophth.com/archive/newsletter/0206_retina.htm.
Saline (medicine)—Wikipedia, the free encyclopedia. http://web.archive.org/web/20110205192937/http://en.wikipedia.org/wiki/Saline_(medicine). Apr. 27, 2012. 4 pages.
Sanborn G.E., et al., Sustained-Release Ganciclovir Therapy for Treatment of Cytomegalovirus Retinitis, Use of an Intravitreal Device, Arch. Ophthalmol, vol. 110, 188-195 (Feb. 1992).
Sheardown and Saltzman, Novel Drug Delivery Systems for Posterior Segment Ocular Disease, *Opthalmology: Ocular Angiogenesis: Diseases, Mechanisms and Therapeutics*, 2007, pp. 393-408.
Smith et al., "Spectrophotometric determination of pKa values for fluorescein using activity coefficient corrections," WaterSA 2002; 28(4):395-402.
Smith, T.J., et al., "Intravitreal Sustained-Release Ganciclovir", *Arch. Ophthamol* 110 (1992) pp. 255-258.
Soheilian et al., "Pilot Study of Intravitreal Injection of Diclofenac for Treatment of Macular Edema of Various Etiologies," Retina, Mar. 2010; 30(3): 509-515.
Stay et al. Computer Simulation of Convective and Diffusive Transport of Controlled-Release Drugs in the vitreous Humor, *Pharm Res* 2003,20(1), pp. 96-102.
Stella et al. "Cyclodextrins." *Toxicologic Pathology.* 2008 36:30-42 (2008).
Theodossiadis et al., "Intravitreal administration of the anti-tumor necrosis factor agent infliximab for neovascular age-related macular degeneration," Am J Ophthalmol. May 2009;147(5):825-830.
Weiner, A.L. "Chapter 13: Polymeric Drug Delivery Systems for the Eye", *Polymeric Site-Specific Pharmacotherapy*, pp. 315-346, Edited by A.J. Domb (1994) John Wiley & Sons Ltd.
Williams, et al., "Treating Diabetic Macular Edema With Ocular NSAIDs," Retinal Physician, Nov. 2007; retrieved from the Internet Nov. 11, 2007. http://www.retinalphysician.com/article.aspx?article=101096>, 5 pages total.
Wright, P., et al. "Slow-Release Artificial Tear Inserts in the Treatment of Dry Eyes Resulting from the Oculomucocutaneous Syndrome", *British Journal of Ophthalmology* 67 (1983) pp. 393-397.
Xu, Jing, et al. "Future of the particle replication in nonwetting templates (Print) technology." *Angewandte Chemie International Edition* 52.26 (2013): 6580-6589.
Yao et al. (Prevention of Laser Photocoagulation Induced Choroidal Neovascularization Lesions by Intravitreal Doses of Ranibizumab in Cynomolgus Monkeys, ARVO 2009 abstract D906). 2 pages.
U.S. Appl. No. 13/814,466, filed Jun. 28, 2013, 2013/0274691.
U.S. Appl. No. 14/753,574, filed Jun. 29, 2015, 2015/0297402.
U.S. Appl. No. 15/102,191, filed Jun. 6, 2016, 2016/0302965.
U.S. Appl. No. 15/807,396, filed Nov. 8, 2017, 2018/0292403.
U.S. Appl. No. 15/877,146, filed Jan. 22, 2018, 2018/0243130.
U.S. Appl. No. 16/004,085, filed Jun. 8, 2018, 2018/0289542.
U.S. Appl. No. 16/091,493, filed Oct. 4, 2018, 2019/0117454.
U.S. Appl. No. 16/380,786, filed Apr. 10, 2019, 2019/0350754.
U.S. Appl. No. 16/386,854, filed Apr. 17, 2019, 2019/0336335.
U.S. Appl. No. 16/434,966, filed Jun. 7, 2019, 2019/0365757.
U.S. Appl. No. 16/540,617, filed Aug. 14, 2019, 2020/0030142.
U.S. Appl. No. 16/671,749, filed Nov. 1, 2019, 2020-0060874.
PCT/US2018/61262, Nov. 15, 2018, WO 2019/10396.

* cited by examiner

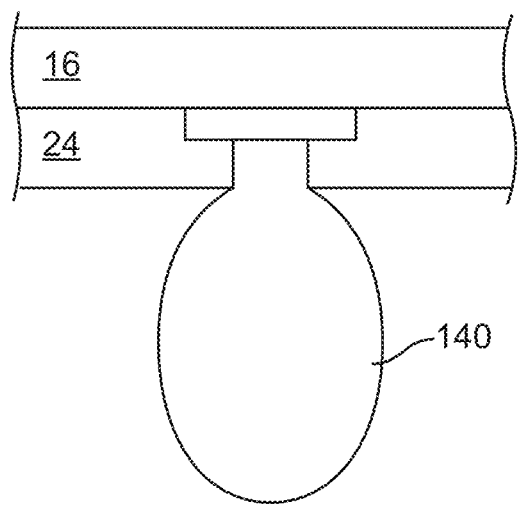
FIG. 1A-2-2
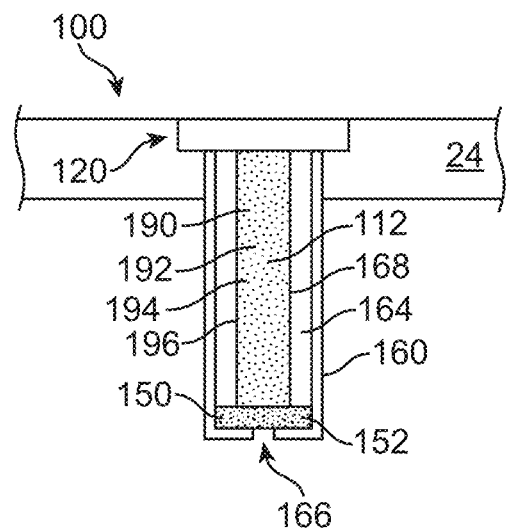
FIG. 1B
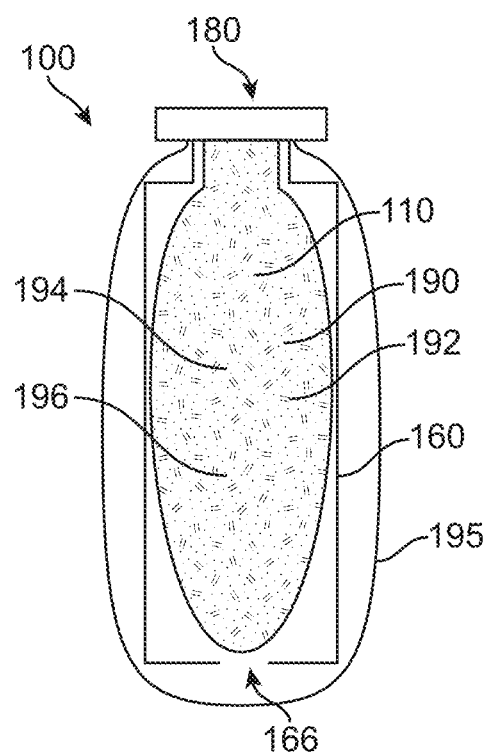
FIG. 1C
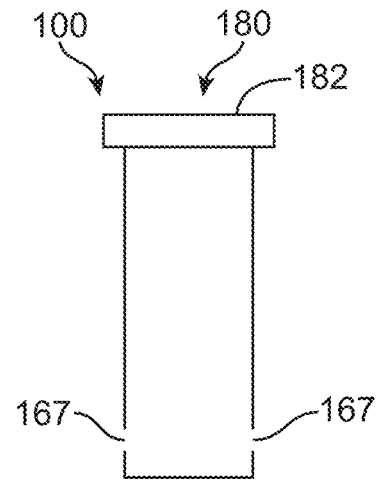
FIG. 1C-A

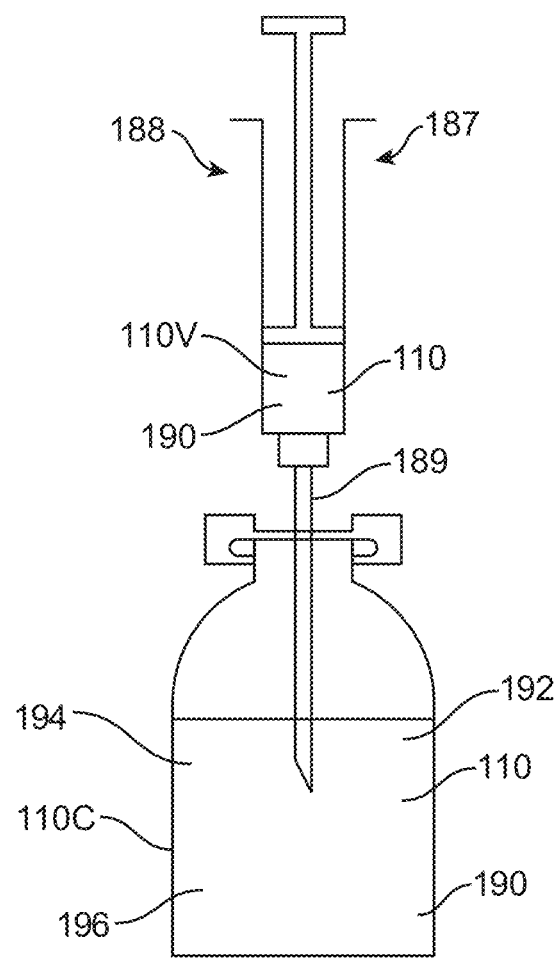
FIG. 1C-B

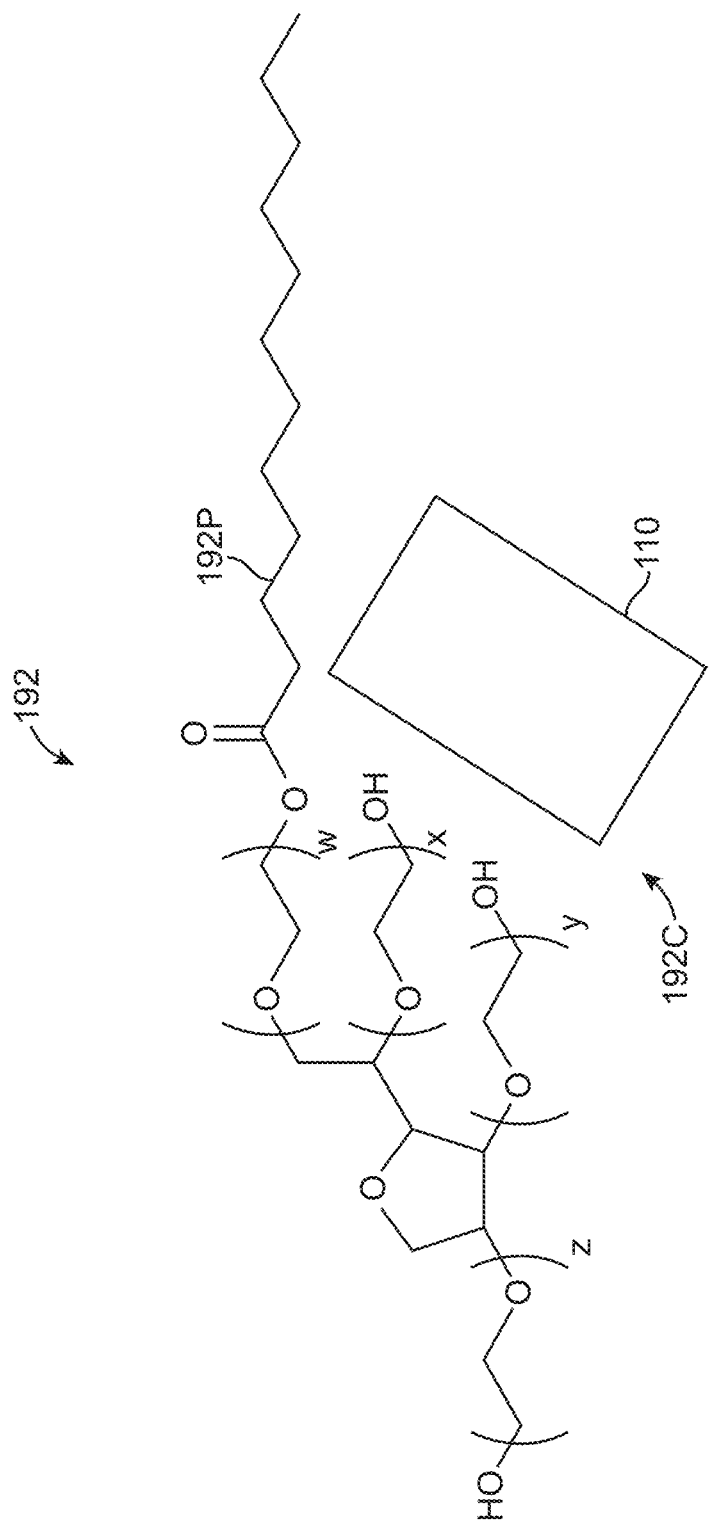
FIG. 3B1

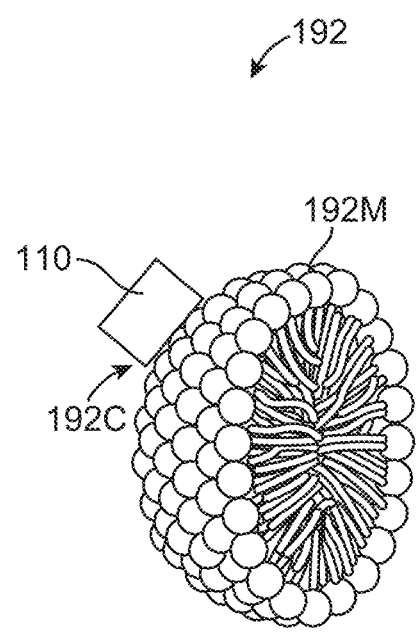
FIG. 3B2

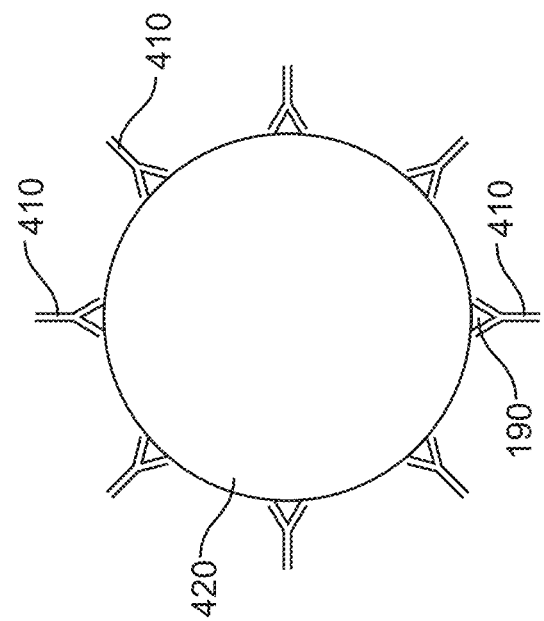
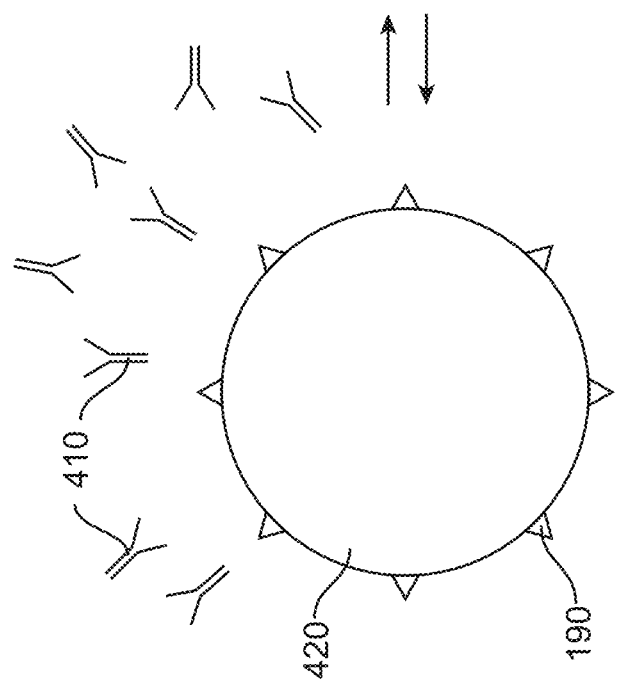

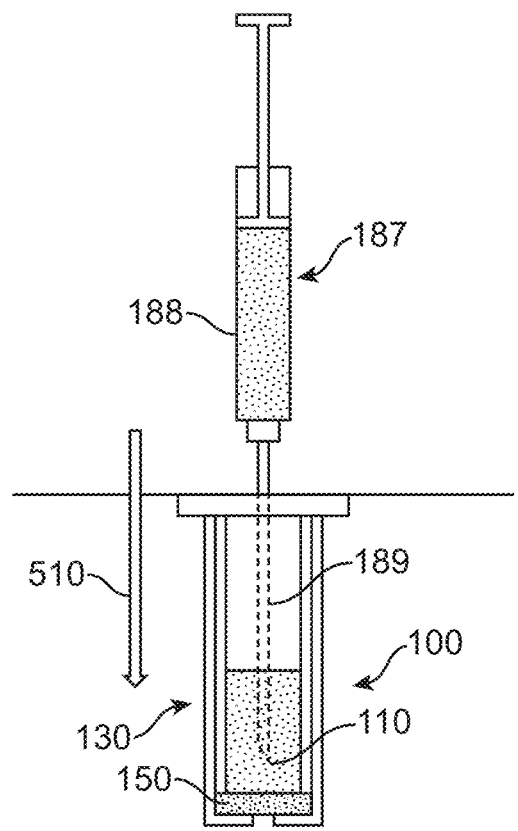
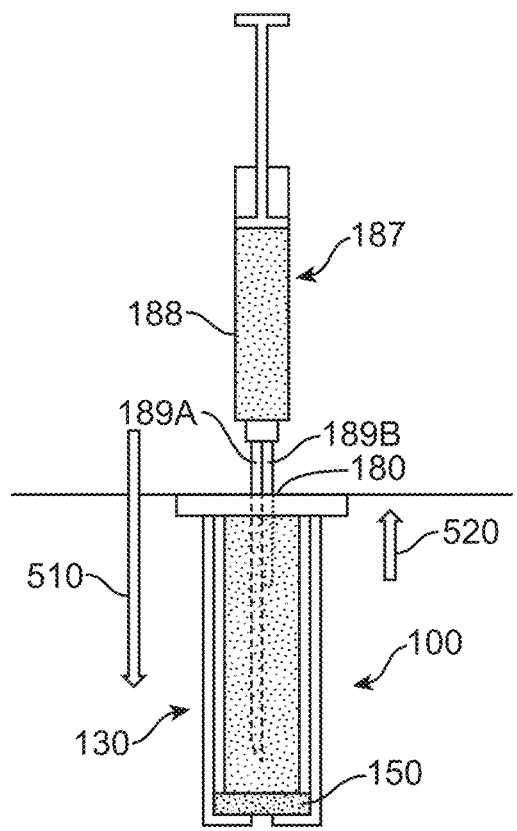
FIG. 5A          FIG. 5A-1
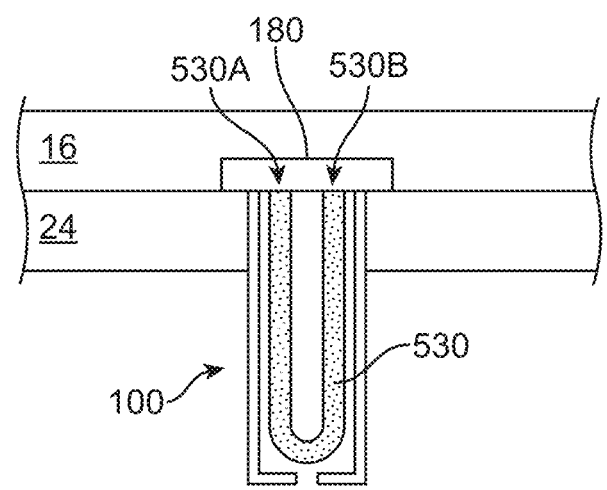
FIG. 5B

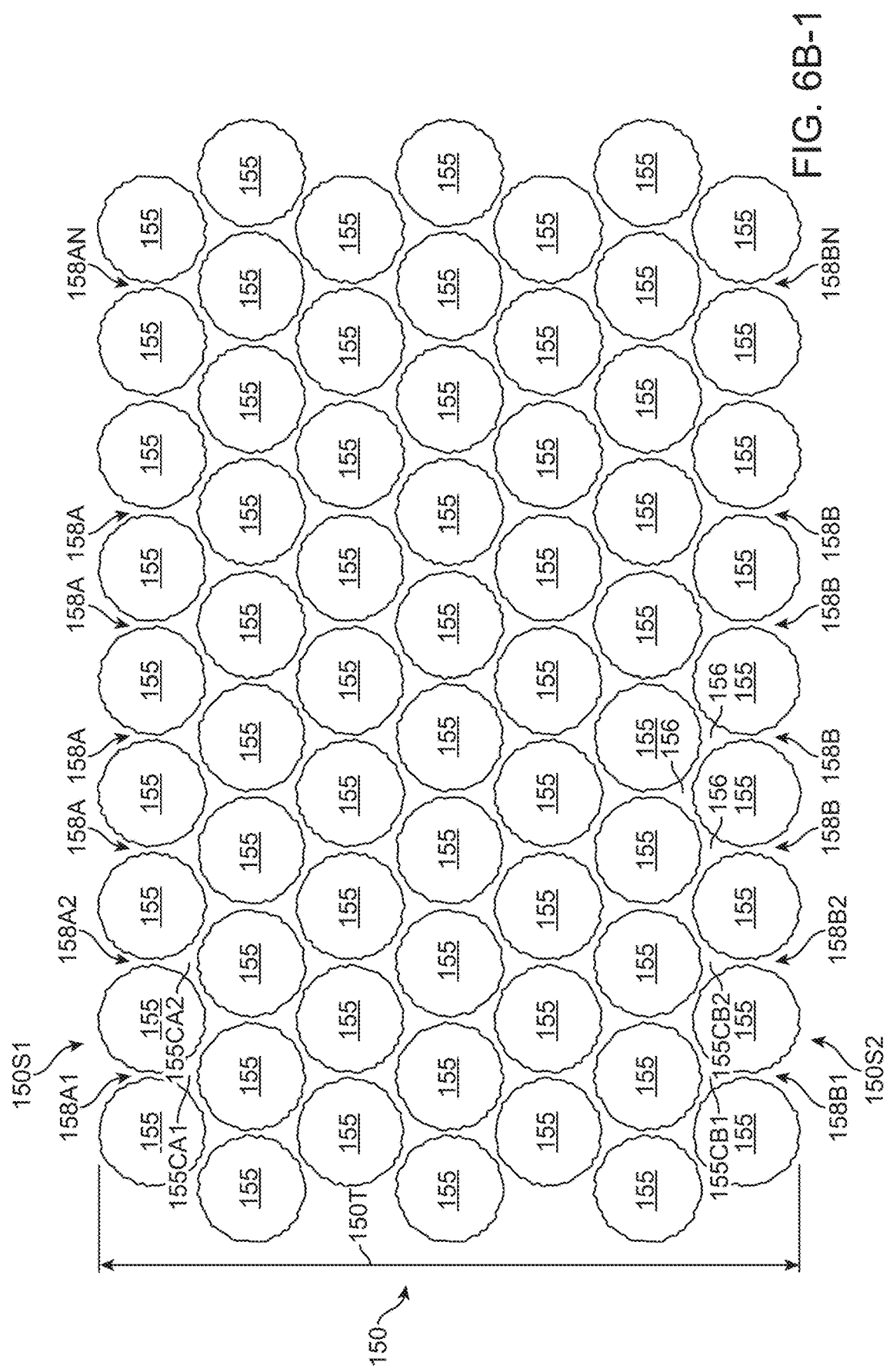

THERAPEUTIC AGENT FORMULATIONS FOR IMPLANTED DEVICES

CROSS-REFERENCES TO RELATED APPLICATIONS

This application is a continuation of co-pending U.S. patent application Ser. No. 13/988,298, entitled "Therapeutic Agent Formulations for Implanted Devices," which is a U.S. national stage application filed under 35 U.S.C. § 371 of International PCT Application No. PCT/US2011/061535, filed Nov. 18, 2011, which claims the benefit of priority under 35 U.S.C. 119(e) of U.S. Prov. Pat. App. Ser. No. 61/415,674, filed Nov. 19, 2010, entitled "THERAPEUTIC AGENT FORMULATIONS FOR IMPLANTED DEVICES", the subject matter of each of the above-noted applications is incorporated by reference thereto in their entireties.

STATEMENT AS TO RIGHTS TO INVENTIONS MADE UNDER FEDERALLY SPONSORED RESEARCH AND DEVELOPMENT

Not Applicable

BACKGROUND

Described herein are devices and methods of delivery of therapeutic agents to the posterior segment of the eye. Although specific reference is made to the delivery of macromolecules comprising antibodies or antibody fragments to the posterior segment of the eye, various related variations can be used to deliver many therapeutic agents to many tissues of the body. For example, some variations can be used to deliver therapeutic agent to one or more of the following tissues: intravascular, intra-articular, intrathecal, pericardial, intraluminal, and gut.

The eye is critical for vision. The eye has a cornea and a lens that form an image on the retina. The image formed on the retina is detected by rods and cones on the retina. The light detected by the rods and cones of the retina is transmitted to the occipital cortex brain via the optic nerve, such that the individual can see the image formed on the retina. Visual acuity is related to the density of rods and cones on the retina. The retina comprises a macula that has a high density of cones, such that the user can perceive color images with high visual acuity.

Unfortunately, diseases can affect vision. In some instances the disease affecting vision can cause damage to the retina, even blindness in at least some instances. One example of a disease that can affect vision is age-related macular degeneration (hereinafter "AMD"). Although therapeutic drugs are known that can be provided to minimize degradation of the retina, in at least some instances the delivery of these drugs can be less than ideal.

In some instances a drug is injected into the eye through the sclera. One promising class of drugs for the treatment of AMD is known as vascular endothelial growth factor (hereinafter "VEGF") inhibitors. Unfortunately, in at least some instances injection of drugs can be painful for the patient, involve at least some risk of infection and hemorrhage and retinal detachment, and can be time consuming for the physician and patient. Consequently, in at least some instances the drug may be delivered less often than would be ideal, such that at least some patients may receive less drug than would be ideal in at least some instances.

Although at least some of the prior proposed implanted devices may permit an injection of a formulation of therapeutic agent into the device, the performance of commercially available formulations of therapeutic agents can be less than ideal in at least some instances when injected into an implantable device. For example, the commercially available formulation may have one or more stabilizers having a molecular weight substantially less than the therapeutic agent, such that stabilizer may be released from the device at a rate faster than the therapeutic agent. Consequently, the therapeutic agent injected into the device may not receive the benefit of the stabilizer as long as would be ideal and may degrade more quickly than would be ideal in at least some instances. Also, the initial rate of release of the therapeutic agent can be somewhat greater than would be ideal and the rate at an extended time can be somewhat lower than would be ideal, such that profile of the rate of release can be less than ideal in at least some instances.

Work in relation to the various related variations suggests that the pH provided in situ after injection into a therapeutic device may be less than ideal for maintaining stability of the therapeutic agent for an extended time in at least some instances. The stability of the therapeutic agent can be related to a pH of the formulation within the device in at least some instances. For example, deamidation of a protein based therapeutic agent may be related to stability of the therapeutic agent, and the deamidation can be related to pH in at least some instances. Work in relation to variations suggests that prior formulations may provide less than ideal stability in one or more ways when injected into a therapeutic device in at least some instances. For example, a buffer of the injected formulation may be released from the device into the vitreous in at least some instances. Also, diffusion of hydrogen ions and hydroxide ions between the reservoir and the vitreous may affect the pH of the formulation within the device.

In at least some instances, one or more molecular components such as a buffer may enter the device when placed in the body, and at least some of the prior formulations may be less stable than would be ideal in at least some instances when exposed to physiological buffer. For example, a buffer of a fluid of the eye such as the vitreous humor having a physiological pH may enter the device and affect the pH of the formulation within the device, such that the stability of the therapeutic agent may be less than ideal in at least some instances.

Work in relation to the various related variations suggests that injection of prior formulations of therapeutic agents into a therapeutic device may result in at least some aggregation of the therapeutic agent in at least some instances, and the aggregation of therapeutic agent may decrease stability of the therapeutic agent, such that the stability of the therapeutic agent when injected into the therapeutic device with prior formulations can be less than ideal in at least some instances.

In light of the above, it would be desirable to provide improved formulations of therapeutic agents for therapeutic devices that overcome at least some of the above deficiencies of the known formulations, for example with improved drug release that can be maintained over an extended time when implanted.

SUMMARY

Described herein are improved formulations of therapeutic agents and improved methods and apparatus for placement into therapeutic devices for an extended time. A flowable, for example injectable, formulation of therapeutic agent may comprise the therapeutic agent and a stabilizer such that a substantial portion of the stabilizer remains in the therapeutic device so as to stabilize the therapeutic agent when the therapeutic agent is released from the therapeutic device. The formulation comprising the therapeutic agent can be placed in the therapeutic device in many ways, and can be injected into the therapeutic device, drawn into the therapeutic device with aspiration, or combinations thereof. The injectable formulation may comprise one or more of binding agent particles or erodible material particles, such that the formulation can be injected into the therapeutic device. The binding agent particles can bind reversibly to the therapeutic agent so as to modulate release of the therapeutic agent, and the erodible material particles can generate protons of an acid so as to increase stability of the therapeutic agent and may modulate release of the therapeutic agent. The therapeutic agent can be combined with one or more of the stabilizer, the binding agent particles or the erodible particles, so as to increase stability of the therapeutic agent and may modulate release of the therapeutic agent from the device.

The stabilizer can interact in many ways with the therapeutic agent so as to increase a stability of the therapeutic agent. The stabilizer may comprise one or more functional groups so as to form a complex with the therapeutic agent. The stabilizer may comprise a co-solute with excluded volume that favors the native state of the protein over the denatured state, so as to increase the stability of the protein. The co-solute with the excluded volume may comprise a stabilizer having a plurality of hydrophilic functional groups so as to provide the excluded volume to favor the native state of the protein. The stabilizer may comprise one or more of a substantially water soluble high molecular weight stabilizer having a molecular weight of at least about 2 k Daltons or micelles sized so as to correspond to a molecular weight of at least about 2 k Daltons. In many variations, the molecular weight of the stabilizer comprises at least about 25% of the molecular weight of the therapeutic agent, such that a substantial portion of the stabilizer injected into the chamber of the therapeutic device with the therapeutic agent remains in the chamber of the therapeutic device for an extended time when the therapeutic agent is released in therapeutic amounts through a porous structure.

The particles of the binding agent may comprise functional groups to bind reversibly to the therapeutic agent such that a substantial portion of the therapeutic agent injected into the chamber of the device may be reversibly bound to the binding agent. The binding agent may comprise porous particles having porous internal channels extending outer surfaces of the particles so as to bind reversibly to the therapeutic agent. The particles may comprise porous resin particles having derivatized functional groups on surfaces of the inner channels. The functional groups can be located on the outer surface and the surfaces of the inner channels so as to bind reversibly to the therapeutic agent, and the surfaces of the inner channels can be fluidically coupled to the outer surface of the particles such that the therapeutic agent can be released from the surfaces of the inner channels. The therapeutic agent released from the binding agent can form a complex with the stabilizer, or dissociate from the binding agent into solution, or combinations thereof. The therapeutic agent bound reversibly to the binding agent, the therapeutic agent complexed with the stabilizer and therapeutic agent in solution can be in substantial equilibrium within the chamber of the device so as to modulate release of the therapeutic agent when the therapeutic agent is stabilized.

The particles of erodible material to generate protons of an acid can maintain a pH of the formulation less than about 7, for example less than about 6.5, when injected into the therapeutic device. The pH less than about 7 can result in decreased amounts of degradation of the therapeutic agent that may occur with one or more degradation pathways. The degradation pathway affected with the pH less than 7 can be one or more of deamidation of the therapeutic agent, such as oxidation of the therapeutic agent, isomerization of the therapeutic agent, clipping of the therapeutic agent, hydrolysis of the therapeutic agent, fragmentation of the therapeutic agent, or aggregation of the therapeutic agent, or combinations thereof. The particles of erodible material may comprise a polymer, such as polylactic acid (hereinafter "PLA", polyglutamic acid (hereinafter "PGA"), or combinations thereof, and the particles may generate protons of an acid in response to degradation such as hydrolysis. In many variations, the particles of binding agent are pH sensitive so as to bind less with increased pH, such that therapeutic agent can be released from the particles in response to an increase in pH.

In a first aspect, variations provide a flowable formulation. The flowable formulation comprises a therapeutic agent, and a stabilizer having a molecular weight of at least about 2 k Daltons.

In many variations, the stabilizer increases an amount of time the therapeutic agent has a therapeutic effect when placed in a therapeutic device placed in a patient. The stabilizer may comprise one or more of, a buffer to maintain a pH of the formulation, hydrophilic functional groups, hydrophilic functional group to provide a co-solvent stabilization, a charged functional group to provide charge interaction, or a functional group to form a complex with the therapeutic agent, so as to increase one or more of physical stability or chemical stability of the therapeutic agent and maintain biological activity of the therapeutic agent. The stabilizer can be soluble and may comprise one or more of a sugar, an alcohol, a polyol, or a carbohydrate and wherein the functional group comprises a hydroxyl group.

In many variations, the therapeutic agent provides a therapeutic effect when placed in the body.

In many variations, the stabilizer comprises a molecular weight of at least about 3 k Daltons. The stabilizer may comprise a molecular weight of at least about 5 k Daltons, and may comprise a molecular weight of at least about 10 k Daltons, for example at least about 25 k Daltons.

In many variations, the stabilizer comprises a molecular weight of at least about 25% of a molecular weight of the therapeutic agent. The stabilizer and the therapeutic agent may each comprise a half-life when placed, for example injected, into a therapeutic device, and the half-life of the stabilizer may comprise at least about 25% of the half-life of the therapeutic agent. The half-life of the stabilizer may comprise of at least about 50% of the half-life of the therapeutic agent.

In many variations, the stabilizer is water-soluble and comprises a molecular weight of no more than about 500% of the molecular weight of the therapeutic agent.

In many variations, the stabilizer is substantially insoluble in water and comprises a molecular weight of no more than about 5000% of the molecular weight of the therapeutic agent.

In many variations, the stabilizer comprises a plurality of substantially water insoluble particles. The stabilizer may comprise a plurality of substantially water insoluble particles having hydrophilic functional groups and a molecular weight of no more than about 5000% of the molecular weight of the therapeutic agent.

In many variations, the therapeutic agent comprises a molecular weight of at least about 40 k. The therapeutic agent may comprise a Fab antibody fragment or a derivative thereof. The therapeutic agent comprises the Fab antibody fragment and deamidized derivatives of the Fab antibody fragment.

In many variations, the therapeutic agent may comprise ranibizumab. The therapeutic agent may comprise ranibizumab and degradation products of ranibizumab, and the degradation products may comprise one or more of deamidized ranibizumab or oxidized ranibizumab.

In many variations, the stabilizer comprising the molecular weight comprises one or more of: HA (hyaluronic acid) having the molecular weight of at least 2 k, histidine polymer buffer having the molecular weight of at least 2 k, sugar having the molecular weight of at least 2 k, polysaccharides having the molecular weight of at least 2 k, carbohydrate having the molecular weight of at least 2 k, starch having the molecular weight of at least 2 k, alcohol having the molecular weight of at least 2 k, polyol having the molecular weight of at least 2 k, or polyethylene oxide having the molecular weight of at least 2 k, so as to stabilize the therapeutic agent and decrease release of the therapeutic agent when placed in a therapeutic device.

In many variations, the stabilizer comprising the molecular weight comprises one or more of: a phenol, a protein, or a charged stabilizers such as a metal comprising one or more of zinc ion, calcium ion, or iron ion, so as to form a reversible complex with the therapeutic agent.

In many variations, the stabilizer comprises a plurality of micelles and wherein the molecular weight of the stabilizer corresponds to a weight of each micelle of the plurality such that diffusion of the plurality of micelles corresponds to the weight of said each micelle. The plurality of micelles may comprise a reservoir of the stabilizer. The stabilizer may comprise a surfactant, and a concentration of surfactant comprises at least about two times a critical micelle concentration of the surfactant. The concentration of surfactant may comprise at least about two times the critical micelle concentration, and may comprise at least about four times the critical micelle concentration.

In many variations, stabilizer comprises a polysorbate.

In many variations, an amount of the stabilizer corresponds to at least about 0.05% by weight of the formulation when injected into the eye.

In many variations, said each of the plurality of micelles forms a complex with the therapeutic agent so as to stabilize the therapeutic agent and decrease diffusion of the therapeutic agent.

In many variations, the container comprises a plurality of particles having a dimension across within a range from about 0.1 um across to about 200 um across, such that the plurality of particles is sized to pass through a lumen of a needle. The dimension across can be within a range from about 0.1 um across to about 50 um across, such that the plurality of particles is sized to pass through a lumen of a 33 Gauge needle.

In many variations, the container comprises a plurality of pellets having a dimension across within a range from about 0.1 um to about 500 um, such that the plurality of particles is sized to pass through a lumen of a 19 Gauge needle.

In many variations, the plurality of particles comprises one or more of a plurality of stabilizer particles, a plurality of erodible particles to generate protons of an acid, or a plurality of binding agent particles.

In many variations, the container comprises a plurality of binding agent particles having a dimension across within a range from about 0.1 um across to about 200 um across, the binding agent particles providing a plurality of reversible binding sites having the therapeutic agent reversibly bound thereon.

In many variations, the therapeutic agent comprises a first portion in solution comprising a first concentration and a second portion reversibly bound to the plurality of binding agent particles comprising a second concentration. An amount of the second portion of the therapeutic agent reversibly bound to the plurality of binding agent particles and a dimension across the plurality of binding agent particles corresponds to the second concentration of the therapeutic agent. The second concentration can be greater than the first concentration.

In many variations, each of the plurality of binding agent particles comprises internal channels extending therein and wherein the internal channels comprise the plurality of reversible binding sites. The plurality of binding agent particles may comprise resin particles having the internal channels and an external surface and wherein the internal surface and the external surface have been treated so as to bind reversibly with the therapeutic agent. The binding agent may comprise a surface derivatized with at least one functional group so as to bind reversibly with the therapeutic agent. The derivatized surface may comprise an anion exchange surface and wherein the at least one functional group comprises one or more of quaternary amines, diethylaminoehtly (hereinafter "DEAE"), quaternary aminoethyl (hereinafter "QAE"), or quaternatry ammonidum (hereinafter "Q"). The derivatized surface comprises a cation exchange surface and wherein the at least one functional group comprises one or more of carboxy methyl (hereinafter "CM"), Sulphoproply (hereinafter "SP"), or methyl sulphonate (hereinafter "SP").

In many variations, the binding agent comprises a negatively charged surface within a range of about pH 5.5 to about pH 7.5 so as to bind reversibly to positive charges of the therapeutic agent. The binding agent comprises a net negative surface charge within a range about pH 6 to about pH 7 and wherein the therapeutic agent comprises a net positive charge so as to bind reversibly to the therapeutic agent. The therapeutic agent comprises an isoelectric pH (pI) of at least about 8 and wherein binding of the therapeutic agent to the binding agent decreases substantially when the pH increases from about 6 to about 7. The therapeutic agent comprises at least about ten positive charges and at least about ten negative charges and wherein derivatized surface comprises positive and negative charges to bind reversibly to the therapeutic agent.

In many variations, the at least one functional group increases a stability of the therapeutic agent when reversibly bound to the therapeutic agent.

In many variations, the plurality of binding agent particles have the dimension within the range from about 0.1 um to about 200 um such that the plurality of binding agent particles comprises a suspension suitable for injection into a chamber of a therapeutic device. The range from about 0.1 um to about 50 um such that the plurality of binding agent particles comprises a suspension suitable for injection through a lumen of a 33 Gauge needle. The plurality of binding agent particles may have the dimension within the range from about 0.5 um to about 100 um such that diffusion of the suspension of binding agent particles through a porous structure is substantially inhibited.

In many variations, the plurality of binding agent particles have the dimension across each particle sized greater than a dimension across channels of a porous structure such that passage of the particles through the porous structure is inhibited substantially.

In many variations, the formulation further comprises a plurality of particles of an erodible material to release protons of an acid. The plurality of erodible particles may comprise one or more of a suspension or a slurry of the erodible particles for injection into or exchange from a therapeutic device.

In many variations, the formulation comprises a pH of at least about 5.5. The plurality of particles of formulation may be capable of releasing about 1E-10 (1×10-10) moles of protons per uL of device reservoir volume so as to maintain a pH of the formulation below about 7 for an extended time of at least about 1 month.

In many variations, the plurality of particles of the erodible material comprises an amount corresponding to about 0.01% to about 5% by weight of the formulation. The erodible material a polymer, the polymer comprising one or more of polylactic acid (PLA), polyglutamic acid (PGA) or PLA/PGA copolymer.

In many variations, the formulation further comprises an amount of the erodible material to maintain the pH of the chamber at no more than about 6.5 for an extended time of at least about 1 month when injected into a chamber of a therapeutic device coupled to the eye with a porous structure. In many variations, an amount of an erodible material to maintain the pH of the chamber at no more than about 6.0 for an extended time of at least about 1 month when exposed to physiological phosphate buffer diffused through the porous structure. The amount of an erodible material may be sufficient to maintain the pH of the chamber at no more than about 6.0 for an extended time of at least about 3 months when exposed to physiological phosphate buffer diffused through the porous structure.

In many variations, the plurality of erodible particles comprises a ratio of PLA to PGA to erode and release protons at a rate to maintain the pH.

In many variations, the plurality of erodible particles comprises a portion of the particles covered with a coating to delay erosion of the portion.

In many variations, the plurality of erodible particles comprises distribution of sizes so as to erode and release protons at a rate to maintain the pH.

In many variations, the plurality of particles comprises the stabilizer mixed with the erodible material to provide the stabilizer when the particle erodes.

In an interrelated aspect, variations provide an injectable formulation. The injectable formulation comprises therapeutic agent, and a stabilizer comprising a plurality of micelles.

In many variations, each of the plurality of micelles comprises a weight corresponding to molecular weight of at least about 2 k Daltons, and the plurality of micelles comprises a reservoir of the stabilizer. A first portion of the stabilizer comprises a solution of the stabilizer and a second portion of the stabilizer comprises the micelles and wherein the stabilizer is released from the micelles to the solution maintain a concentration of the first portion of the stabilizer in solution. The stabilizer may comprise a polymeric surfactant and wherein a concentration of polymeric surfactant is higher than a threshold concentration to form one or more of the plurality of micelles and wherein the concentration of the polymeric surfactant comprises the first portion and the second portion.

In another interrelated aspect, variations provide injectable formulation, the formulation comprises a therapeutic agent, and an erodible material to generate protons of an acid. The erodible material comprises an amount to erode and maintain a pH of no more than about 6.5 when the formulation is combined with physiological amounts of phosphate buffer.

In many variations, the injectable formulation further comprises a plurality of particles, wherein each of the plurality of particles comprises the erodible material and a hydrophilic stabilizer such that the hydrophilic stabilizer is released when said each particle of the plurality erodes.

In another interrelated aspect, variations provide method of preparing an injectable formulation, the method comprising: combining a therapeutic agent and a stabilizer.

In many variations, the stabilizer has a molecular weight of at least about 2 k Daltons.

In another interrelated aspect, variations provide device to treat an eye. The device comprises a reservoir chamber having a volume sized to receive an injection of an amount of a formulation of a therapeutic agent, and a porous structure to release therapeutic amounts of the therapeutic agent for an extended time. A stabilizer is configured to maintain stability of the therapeutic agent in the reservoir chamber, and the stabilizer comprises a molecular weight of at least about 5 k Daltons such that a portion of the stabilizer remains in the reservoir chamber for the extended time.

In many variations, the stabilizer comprises a molecular weight of at least about 10 k. The stabilizer may comprise a molecular weight of at least about 25% of a molecular weight of the therapeutic agent, and the molecular weight can be at least about 40 k. The therapeutic agent comprises a Fab antibody fragment or a derivative thereof. The therapeutic agent may comprise ranibizumab.

In many variations, the stabilizer further comprising an amount of an erodible material to maintain the pH of the chamber at no more than about 6.5 for an extended time of at least about 1 month.

In many variations, the stabilizer further comprising an amount of an erodible material to maintain the pH of the chamber at no more than about 6.0 for an extended time of at least about 1 month.

In many variations, the stabilizer comprises a plurality of particles to bind reversibly to the therapeutic agent, a majority of the plurality of particles having a size greater than channels of the porous structure such that the particles remain in the reservoir chamber for the extended time.

In another interrelated aspect, variations provide method of treating an eye. A therapeutic device comprising a reservoir chamber and a porous structure is provided, in which the reservoir chamber has a volume sized to receive an injection of an amount of a formulation of a therapeutic agent, and the porous structure is configured to release therapeutic amounts of the therapeutic agent for an extended time. A stabilizer and the therapeutic agent are injected into the reservoir chamber, and the stabilizer maintains stability of the therapeutic agent in the reservoir chamber, the stabilizer comprising a molecular weight of at least about 5 k Daltons, and a substantial portion of the stabilizer remains in the reservoir chamber for the extended time.

In another interrelated aspect, variations provide an apparatus to treat an eye. A first container comprises a formulation of a therapeutic agent, the formulation comprising a stabilizer and the therapeutic agent, and a second container comprises an erodible material to release protons of an acid.

In many variations, the second container comprises particles of the erodible material such that the particles form a suspension of the erodible material when mixed with the formulation.

In many variations, the erodible material releases an acid when wet so as to maintain substantially a pH of the formulation when mixed with the formulation and injected into a therapeutic device.

In many variations, the second container comprises a syringe having the erodible material stored therein, and the syringe comprises an exchange syringe.

In many variations, the second container comprises a cartridge having the erodible material stored therein, the cartridge configured to couple to a syringe having the formulation of the therapeutic agent contained therein, so as to mix the erodible material with the formulation upon injection into or exchange with a therapeutic device.

In many variations, the container stores the erodible material substantially without water.

In many variations, the stabilizer comprises a molecular weight of at least about 5 k Daltons and the therapeutic agent comprises a molecular weight of at least about 25 k Daltons.

In many variations, the container comprises a plurality of binding agent particles having a dimension across within a range from about 0.1 um across to about 200 um across, the binding agent particles providing a plurality of reversible binding sites to receive the therapeutic agent.

In many variations, the dimension across is within a range from about 0.5 um across to about 100 um across.

In many variations, each of the plurality of binding agent particles comprises internal channels extending therein and wherein the internal channels comprise the plurality of reversible binding sites. The plurality of binding agent particles may comprise resin particles having the internal channels and an external surface treated so as to bind reversibly with the therapeutic agent.

In many variations, the plurality of particles comprises a second stabilizer so as to release the second stabilizer when the erodible material erodes and generates the protons of the acid.

In many variations, the second stabilizer comprises one or more of a sugar, an alcohol, a polyol, a polysaccharide, or a carbohydrate.

In many variations, the second stabilizer comprises one or more of a buffer or pH modifier.

In many variations, the second stabilizer comprises hydroxyl groups.

In another interrelated aspect, variations provide a method of preparing a formulation. A formulation of a therapeutic agent can be provided, in which the formulation comprises a stabilizer and the therapeutic agent. An erodible material is provided to release protons of an acid, and the formulation is mixed with the erodible material.

In another interrelated aspect, variations provide an injectable and exchangeable formulation to treat an eye. The formulation comprises a therapeutic agent having a molecular weight of at least about 40 k Daltons, and a stabilizer having a molecular weight of at least about 10 k Daltons. The stabilizer is capable of forming a complex with the therapeutic agent to stabilize the therapeutic agent. A first plurality of binding agent particles has a plurality of sites to bind reversibly the therapeutic agent. A second plurality of erodible particles to generate an acid, wherein the first plurality of binding agent particles and the second plurality of erodible particles comprise a suspension such that the formulation is capable of injection into a therapeutic device and exchange from the therapeutic device.

In another interrelated aspect, variations provide method of treating an eye. A formulation is provided, and the formulation comprises a therapeutic agent, a stabilizer, a first plurality of binding agent particles and a second plurality of erodible particles, the therapeutic agent having a molecular weight of at least about 40 k Daltons. The formulation is placed in a chamber of a therapeutic device.

In many variations, the stabilizer has a molecular weight of at least about 10 k Daltons, and the stabilizer is capable of forming a complex with the therapeutic agent to stabilize the therapeutic agent. The first plurality of binding agent particles has a plurality of sites to bind reversibly the therapeutic agent. The second plurality of erodible particles generates an acid, and the first plurality of binding agent particles and the second plurality of erodible particles comprise a suspension such that the formulation is capable of injection into a therapeutic device and exchange from the therapeutic device.

In many variations, placing comprises exchanging the formulation with a portion of a previously placed formulation, in which the portion of the previously placed formulation comprises, water, deamidated therapeutic agent, and binding agent particles.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

FIG. 1A-1 shows a therapeutic device implanted at least partially within the sclera of the eye as in FIG. 1;

FIGS. 1A-1-1 and 1A-1-2 show a therapeutic device implanted under the conjunctiva and extending through the sclera to release a therapeutic agent into vitreous humor of the eye so as to treat the retina, in accordance with variations described herein;

FIG. 1A-2 shows structures of a therapeutic device configured for placement in an eye as in FIGS. 1A-1 and 1A-1-1, in accordance with variations described herein;

FIG. 1A-2-1 shows a therapeutic device loaded into an insertion cannula, in which the device comprises an elongate narrow shape for insertion into the sclera, and in which the device is configured to expand to a second elongate wide shape for retention at least partially in the sclera, in accordance with variations described herein;

FIG. 1A-2-2 shows a therapeutic device comprising a reservoir suitable for loading in a cannula, in accordance with variations described herein;

FIG. 1B shows a therapeutic device configured for placement in an eye as in FIGS. 1A-1 and 1A-1-1, in accordance with variations described herein;

FIG. 1C shows a therapeutic device configured for placement in an eye as in FIGS. 1A-1 and 1A-1-1, in accordance with variations described herein;

FIG. 1C-A shows at least one exit port, according to variations described herein;

FIG. 1C-B shows a syringe being filled with a formulation 190 comprising therapeutic agent 110 and one or more of stabilizer 192, binding agent 194 or particles 196, for injection into the therapeutic device, in accordance with variations described herein;

FIG. 2 shows an access port suitable for incorporation with the therapeutic device, in accordance with variations described herein;

FIG. 3B1 shows a stabilizer as in FIG. 3A, in accordance with variations described herein;

FIG. 3B2 shows a micelle of a stabilizer as in FIG. 3A, in accordance with variations described herein;

FIG. 4A shows released fragments of antibodies, and FIG. 4B shows antibody fragments reversibly bound to a substrate, in accordance with variations described herein;

FIG. 5A shows a therapeutic device coupled to an injector to insert therapeutic agent into the device, in accordance with variations described herein;

FIG. 5A-1 shows a therapeutic device coupled to an injector to simultaneously inject and remove material from the device, in accordance with variations described herein;

FIG. 5B shows a therapeutic device comprising a micro loop channel, in accordance with variations described herein;

FIG. 5C-1 shows a therapeutic device comprising a tortuous channel, in accordance with variations described herein;

FIG. 5C-2 shows a therapeutic device comprising a coiled channel, in accordance with variations described herein;

FIG. 6A-1 shows a therapeutic device comprising a container having a penetrable barrier disposed on a first end, a porous structure disposed on a second end to release therapeutic agent for an extended period, and a retention structure comprising an extension protruding outward from the container to couple to the sclera and the conjunctiva, in accordance with variations described herein;

FIG. 6A-2 shows a therapeutic device as in FIG. 6A-1 comprising a rounded distal end, in accordance with variations described herein;

FIG. 6B-1 shows interconnecting channels extending from a first side to a second side of the porous structure as in FIG. 6B, in accordance with variations described herein;

DETAILED DESCRIPTION

Figure 1:
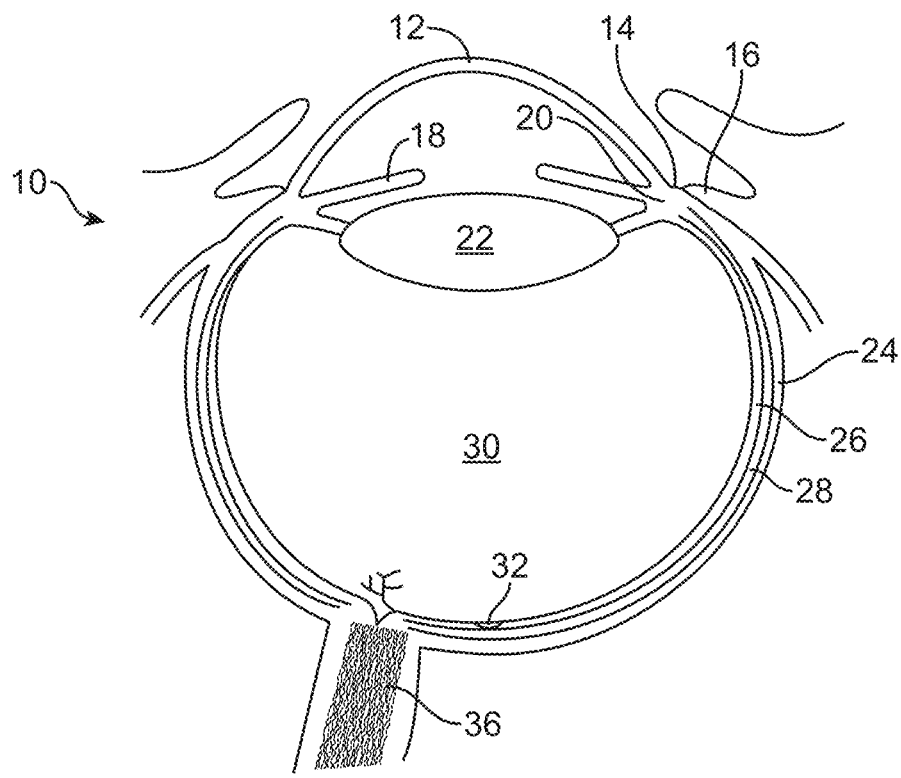
FIG. 1 shows an eye suitable for incorporation of variations of the therapeutic device.

Although specific reference is made to the delivery of macromolecules comprising antibodies or antibody fragments to the posterior segment of the eye, a variety of implementations described herein can be used to deliver many therapeutic agents to many tissues of the body. For example, variations described herein can be used to deliver therapeutic agent for an extended period to one or more of the following tissues: intravascular, intra articular, intrathecal, pericardial, intraluminal, and gut.

Various implementations as described herein are suitable for combination in accordance with U.S. patent application Ser. No. 12/696,678 filed on Jan. 29, 2010, entitled "POSTERIOR SEGMENT DRUG DELIVERY," published on Oct. 7, 2010 as U.S. Pub. No. 2010/0255061, the full disclosure of which is incorporated herein by reference.

Variations described herein provide sustained release of a therapeutic agent to the posterior segment of the eye or the anterior segment of the eye, or combinations thereof. Therapeutic amounts of a therapeutic agent can be released into the vitreous humor of the eye, such that the therapeutic agent can be transported by at least one of diffusion or convection to the retina or other ocular tissue, such as the choroid or ciliary body, for therapeutic effect.

The formulations as described herein can be combined with many therapeutic agents, and may comprise one or more components of commercially available formulations. The stabilizers and erodible particles as described herein can be combined with commercially available formulations, for example, so as to decrease degradation of the therapeutic agent injected into the device.

The formulations as described herein can be combined in many ways and can be used with one or more of many therapeutic devices so as to provide therapeutic amounts for an extended time. The formulation can be provided within a therapeutic device prior to implantation, and can be placed in the therapeutic device when the device has been implanted, for example.

The formulation can be placed in a therapeutic device placed in the eye in many ways. Many variations as described herein are particularly well suited for injection into a therapeutic device implanted in the body. Alternatively or in combination, the formulation can be placed in a container and the container placed in the therapeutic device implanted in the eye, for example.

As used herein, the release rate index encompasses (PA/FL) where P comprises the porosity, A comprises an effective area, F comprises a curve fit parameter corresponding to an effective length and L comprises a length or thickness of the porous structure. The units of the release rate index (RRI) comprise units of mm unless indicated otherwise and can be determined in accordance with the teachings described hereon.

As used herein, sustained release encompasses release of therapeutic amounts of an active ingredient of a therapeutic agent for an extended period of time. The sustained release may encompass first order release of the active ingredient, zero order release of the active ingredient, or other kinetics of release such as intermediate to zero order and first order, or combinations thereof.

As used herein, a therapeutic agent referred to with a trademark encompasses the active ingredient available under the trademark and derivatives thereof.

As used herein, similar numerals indicate similar structures and/or similar steps.

As used herein, Trehalose encompasses an alpha-linked disaccharide formed by an α,α-1,1-glucoside bond between two α-glucose units. Trehalose can be referred to as mycose or tremalose.

As used herein, the critical micelle concentration (CMC) encompasses the concentration of surfactants above which micelles are spontaneously formed.

As used herein, a surfactant encompasses a wetting agent capable of lowering the surface tension of water.

As used herein, scientific notation of the form $a \times 10^{-b}$ can be expressed as aE-b (or ae-b) with E notation known to persons of ordinary skill in the art familiar with the use of computer programs, calculators and spreadsheets.

The therapeutic agent may be contained within a chamber of a container, for example within a reservoir comprising the container and chamber. The therapeutic agent may comprise a formulation such as solution of therapeutic agent, a suspension of a therapeutic agent or a dispersion of a therapeutic agent, for example. Examples of therapeutic agents suitable for use in accordance with variations of the therapeutic device are described herein, for example with reference to Table 1A below and elsewhere.

Examples of known surfactants suitable for combination with therapeutic agents in accordance with variations as described herein can be found in Table 1B and at one or more locations on the world wide web, such as at the known website Wikipedia (en.wikipedia.org/wiki/Surfactant). The surfactant may comprise an amount sufficient so as to form micelles comprising a reservoir of stabilizer.

The surfactant may comprise a head and a tail. The surfactant may be categorized according to a head of the surfactant and a tail of the surfactant. The tail may comprise one or more of a hydrocarbon chain, an alkyl ether chain, a fluorocarbon chain or a siloxane chain. The hydrocarbon chain may comprise one or more of aromatic hydrocarbons (arenes), alkanes (alkyl), alkenes, cycloalkanes, or alkyne-based chains. The alkyl ether chain may comprise one or more of: ethoxylated surfactants, such as polyethylene oxides inserted so to increase the hydrophilic character of a surfactant; or propoxylated surfactants: polypropylene oxides inserted to increase the lipophilic character of a surfactant. The fluorocarbon chain may comprise fluorosurfactants. The siloxane chain may comprise siloxane surfactants. Surfactant can have one or two tails (double chained surfactants).

A surfactant may be categorized by the presence of formally charged groups in its head. A non-ionic surfactant may have no charge groups in the head. The head of an ionic surfactant can carry a net charge. When the charge is negative, the surfactant can be more specifically called anionic. When the charge is positive, the surfactant can be called cationic. When a surfactant contains a head with two oppositely charged groups, the surfactant can be referred to as zwitterionic.

Examples of known polyscahharides that may be combined with the therapeutic agent in accordance with variations described herein are as listed in Table 1C, and can be found on the World Wide Web (en.wikipedia.org/wiki/Polysaccharide).

The therapeutic agent may comprise a macromolecule, for example an antibody or antibody fragment. The therapeutic macromolecule may comprise a VEGF inhibitor, for example the active ingredient ranibizumab of Lucentis™ and derivatives thereof. The VEGF (Vascular Endothelial Growth Factor) inhibitor can cause regression of the abnormal blood vessels and improvement of vision when released into the vitreous humor of the eye. Examples of VEGF inhibitors include Lucentis™, Avastin™, Macugen™, and VEGF Trap that can be provided with formulations in accordance with variations described herein.

The therapeutic agent may comprise small molecules such as of a corticosteroid and analogues thereof. For example, the therapeutic corticosteroid may comprise one or more of trimacinalone, trimacinalone acetonide, dexamethasone, dexamethasone acetate, fluocinolone, fluocinolone acetate, or analogues thereof. Alternatively or in combination, the small molecules of therapeutic agent may comprise a tyrosine kinase inhibitor comprising one or more of axitinib, bosutinib, cediranib, dasatinib, erlotinib, gefitinib, imatinib, lapatinib, lestaurtinib, nilotinib, semaxanib, sunitinib, toceranib, vandetanib, or vatalanib, for example.

The therapeutic agent may comprise an anti-VEGF therapeutic agent. Anti-VEGF therapies and agents can be used in the treatment of certain cancers and in age-related macular degeneration. Examples of anti-VEGF therapeutic agents suitable for use in accordance with the variations described herein include one or more of monoclonal antibodies such as bevacizumab (Avastin™) or antibody derivatives such as ranibizumab (Lucentis™), or small molecules that inhibit the tyrosine kinases stimulated by VEGF such as lapatinib (Tykerb™), sunitinib (Sutent™), sorafenib (Nexavar™), axitinib, or pazopanib.

The therapeutic agent may comprise a therapeutic agent suitable for treatment of dry AMD such as one or more of Sirolimus™ (Rapamycin), Copaxone™ (Glatiramer Acetate), Othera™, Complement C5aR blocker, Ciliary Neurotrophic Factor, Fenretinide or Rheopheresis.

The therapeutic agent may comprise a therapeutic agent suitable for treatment of wet AMD such as one or more of REDD14NP (Quark), Sirolimus™ (Rapamycin), ATG003; Regeneron™ (VEGF Trap) or complement inhibitor (POT-4).

The therapeutic agent may comprise a kinase inhibitor such as one or more of bevacizumab (monoclonal antibody), BIBW 2992 (small molecule targeting EGFR/Erb2), cetuximab (monoclonal antibody), imatinib (small molecule), trastuzumab (monoclonal antibody), gefitinib (small molecule), ranibizumab (monoclonal antibody), pegaptanib (small molecule), sorafenib (small molecule), dasatinib (small molecule), sunitinib (small molecule), erlotinib (small molecule), nilotinib (small molecule), lapatinib (small molecule), panitumumab (monoclonal antibody), vandetanib (small molecule) or E7080 (targeting VEGFR2/ VEGFR2, small molecule commercially available from Esai, Co.)

The amount of therapeutic agent within the therapeutic device may comprise from about 0.01 mg to about 100 mg, for example Lucentis™, so as to provide therapeutic amounts of the therapeutic agent for the extended time, for example at least 30 days. The extended time may comprise at least 90 days or more, for example at least 180 days or for example at least 1 year, at least 2 years or at least 3 years or more. The target threshold therapeutic concentration of a therapeutic agent such as Lucentis™ in the vitreous may comprise at least a therapeutic concentration of 0.1 ug/mL. For example the target threshold concentration may comprise from about 0.1 ug/mL to about 5 ug/mL for the extended time, where the upper value is based upon calculations shown in Example 9 of U.S. patent application Ser. No. 12/696,678 filed on Jan. 29, 2010, entitled "POSTERIOR SEGMENT DRUG DELIVERY," published on Oct. 7, 2010 as U.S. Pub. No. 2010/0255061, the full disclosure of which has been previously incorporated by reference. The target threshold concentration is drug dependent and thus may vary for other therapeutic agents.

The delivery profile may be configured in many ways to obtain a therapeutic benefit from the sustained release device. For example, an amount of the therapeutic agent may be inserted into the container at monthly intervals so as to ensure that the concentration of therapeutic device is above a safety protocol or an efficacy protocol for the therapeutic agent, for example with monthly or less frequent injections into the container. The sustained release can result in an improved delivery profile and may result in improved results. For example, the concentration of therapeutic agent may remain consistently above a threshold amount, for example 0.1 ug/mL, for the extended time.

The insertion method may comprise inserting a dose into the container of the therapeutic device. For example, a single injection of Lucentis™ may be injected into the therapeutic device.

The duration of sustained delivery of the therapeutic agent may extend for twelve weeks or more, for example four to six months from a single insertion of therapeutic agent into the device when the device is inserted into the eye of the patient.

The therapeutic agent may be delivered in many ways so as to provide a sustained release for the extended time. For example, the therapeutic device may comprise a therapeutic agent and a binding agent. The binding agent may comprise small particles configured to couple releasably or reversibly to the therapeutic agent, such that the therapeutic agent is released for the extended time after injection into the vitreous humor. The particles can be sized such that the particles remain in the vitreous humor of the eye for the extended time.

The therapeutic agent may be delivered with a device implanted in the eye. For example, the drug delivery device can be implanted at least partially within the sclera of the eye, so as to couple the drug delivery device to the sclera of the eye for the extended period of time. The therapeutic device may comprise a drug and a binding agent. The drug and binding agent can be configured to provide the sustained release for the extended time. A membrane or other diffusion barrier or mechanism may be a component of the therapeutic device to release the drug for the extended time.

The lifetime of the therapeutic device and number of injections can be optimized for patient treatment. For example, the device may remain in place for a lifetime of 30 years, for example with AMD patients from about 10 to 15 years. For example, the device may be configured for an implantation duration of at least two years, with 8 injections (once every three months) for sustained release of the therapeutic agent over the two year duration. The device may be configured for implantation of at least 10 years with 40 injections (once every three months) for sustained release of the therapeutic agent.

The therapeutic device can be refilled in many ways. For example, the therapeutic agent can be refilled into the device in the physician's office.

The therapeutic device may comprise many configurations and physical attributes, for example the physical characteristics of the therapeutic device may comprise at least one of a drug delivery device with a suture, positioning and sizing such that vision is not impaired, and biocompatible material. The device may comprise a reservoir capacity from about 0.005 cc to about 0.2 cc, for example from about 0.01 cc to about 0.1 cc, and a device volume of no more than about 2 cc. A vitrectomy may be performed for device volumes larger than 0.1 cc. The length of the device may not interfere with the patient's vision and can be dependent on the shape of the device, as well as the location of the implanted device with respect to the eye. The length of the device may also depend on the angle in which the device is inserted. For example, a length of the device may comprise from about 4 to 6 mm. Since the diameter of the eye is about 24 mm, a device extending no more than about 6 mm from the sclera into the vitreous may have a minimal effect on patient vision.

Variations may comprise many combinations of implanted drug delivery devices. The therapeutic device may comprise a drug and binding agent. The device may also comprise at least one of a membrane, an opening, a diffusion barrier, a diffusion mechanism so as to release therapeutic amounts of therapeutic agent for the extended time.

FIG. 1 shows an eye 10 suitable for incorporation of the therapeutic device. The eye has a cornea 12 and a lens 22 configured to form an image on the retina 26. The cornea can extend to a limbus 14 of the eye, and the limbus can connect to a sclera 24 of the eye. A conjunctiva 16 of the eye can be disposed over the sclera. The lens can accommodate to focus on an object seen by the patient. The eye has an iris 18 that may expand and contract in response to light. The eye also comprises a choroid 28 disposed between the sclera 24 and the retina 26. The retina comprises the macula 32. The eye comprises a pars plana 25, which comprises an example of a region of the eye suitable for placement and retention, for example anchoring, of the therapeutic device 100 as described herein. The pars plana region may comprise sclera and conjunctiva disposed between the retina and cornea. The therapeutic device can be positioned so as to extend from the pars plana region into the vitreous humor 30 to release the therapeutic agent. The therapeutic agent can be released into the vitreous humor 30, such that the therapeutic agent arrives at the retina and choroids for therapeutic effect on the macula. The vitreous humor of the eye comprises a liquid disposed between the lens and the retina. The vitreous humor may comprise convection currents to deliver the therapeutic agent to the macula.

Figures 1, 1A:
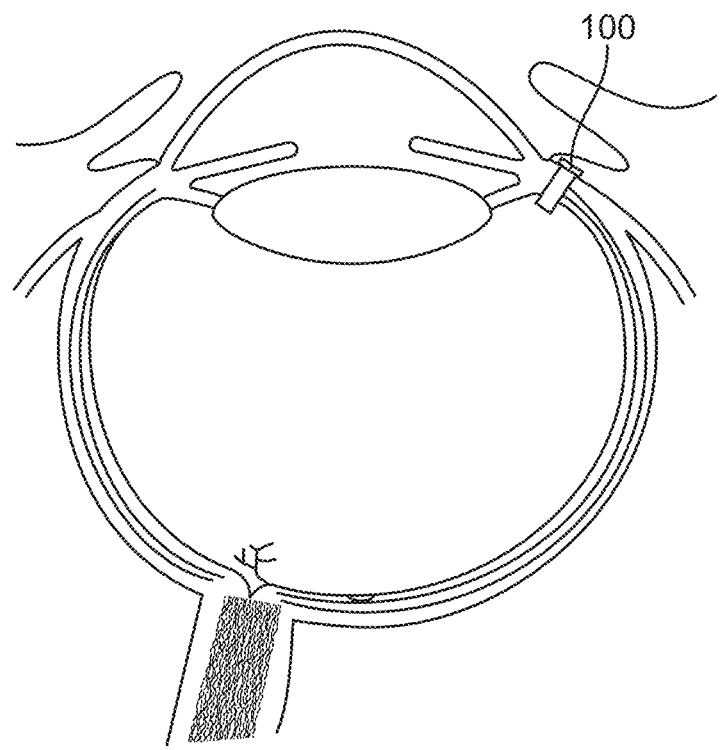
Figures 1, 1A:
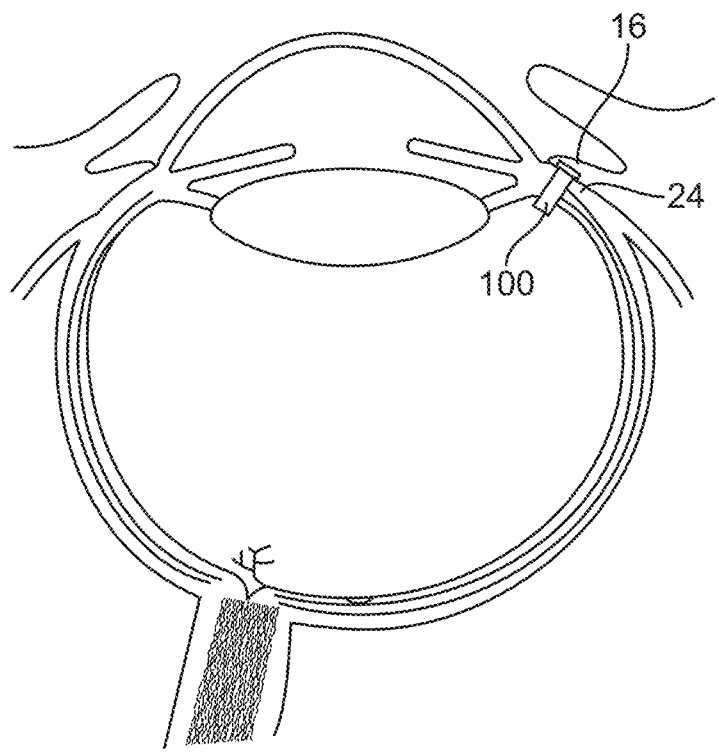

FIG. 1A-1 shows a therapeutic device 100 implanted at least partially within the sclera 24 of the eye 10 as in FIG. 1. The therapeutic device may comprise a retention structure, for example a protrusion, to couple the device to the sclera. The therapeutic device may extend through the sclera into vitreous humor 30, such that the therapeutic device can release the therapeutic agent into the vitreous humor.

Figures 1, 1A, 2:
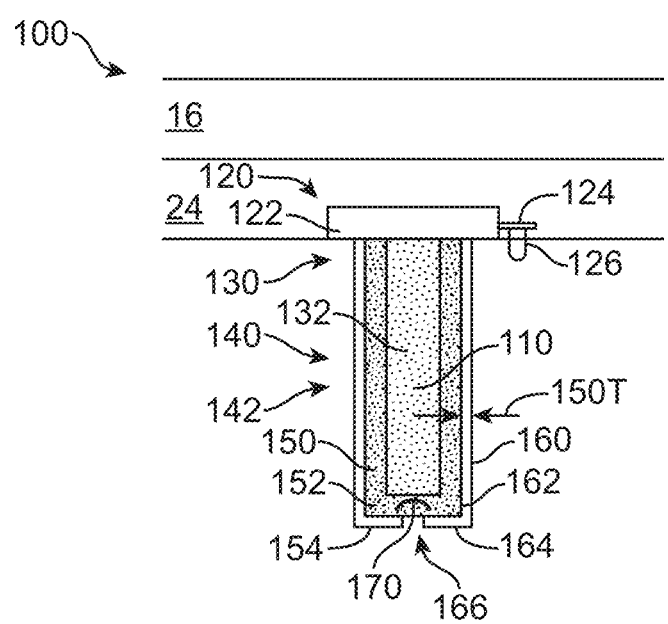
Figures 1, 1A, 2:
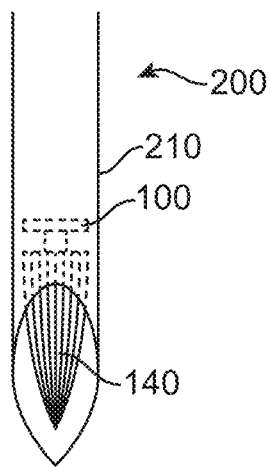
Figures 1, 1A, 2:
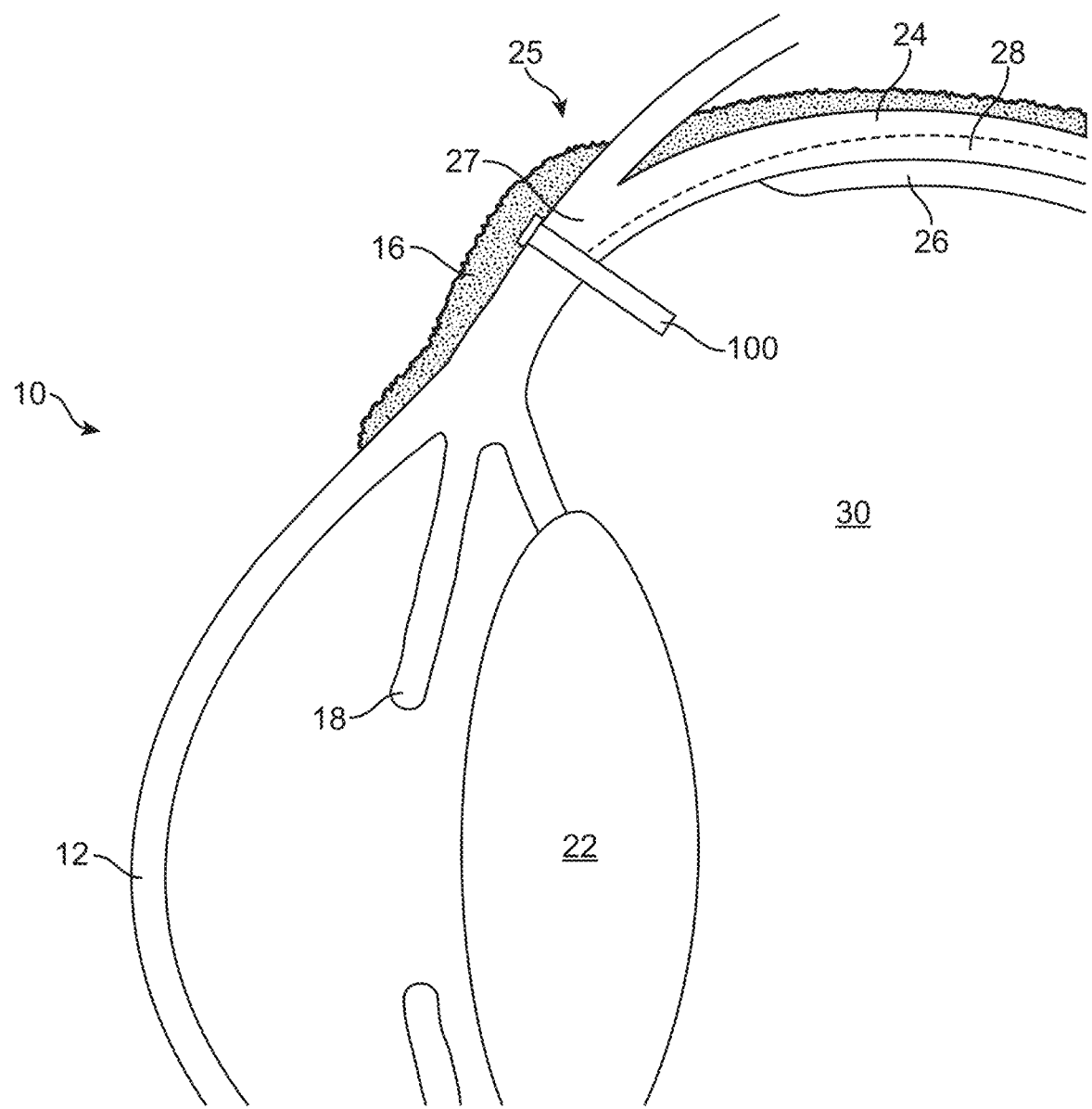
Figure 2:
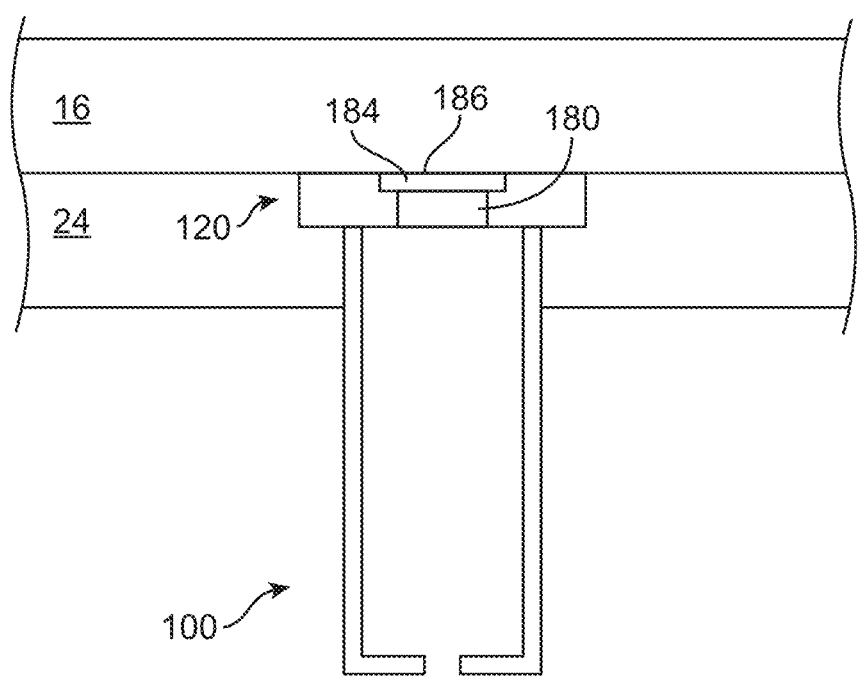

FIGS. 1A-1-1 and 1A-1-2 shows a therapeutic device 100 implanted under the conjunctiva 16 and extending through the sclera 24 to release a therapeutic agent 110 into vitreous humor 30 of the eye 10 so as to treat the retina of the eye. The therapeutic device 100 may comprise a retention structure 120 such as a smooth protrusion configured for placement along the sclera and under the conjunctiva, such that the conjunctiva can cover the therapeutic device and protect the therapeutic device 100. When the therapeutic agent 110 is inserted into the device 100, the conjunctiva may be lifted away, incised, or punctured with a needle to access the therapeutic device. The eye may comprise an insertion of the tendon 27 of the superior rectus muscle to couple the sclera of the eye to the superior rectus muscle. The device 100 may be positioned in many locations of the pars plana region, for example away from tendon 27 and one or more of posterior to the tendon, under the tendon, or with nasal or temporal placement of the therapeutic device.

While the implant can be positioned in the eye in many ways, work in relation to variations suggests that placement in the pars plana region can release therapeutic agent into the vitreous to treat the retina, for example therapeutic agent comprising an active ingredient composed of large molecules.

Therapeutic agents 110 suitable for use with device 100 includes many therapeutic agents, for example as listed in Table 1A, herein below. The therapeutic agent 110 of device 100 may comprise one or more of an active ingredient of the therapeutic agent, a formulation of the therapeutic agent, components of a formulation of the therapeutic agent, a physician prepared formulation of therapeutic agent, or a pharmacist prepared formulation of the therapeutic agent. The therapeutic agent may be referred to with generic name or a trademark, for example as shown in Table 1A.

The therapeutic device 100 can be implanted in the eye to treat the eye for as long as is helpful and beneficial to the patient. For example, the device can be implanted for at least about 5 years, such as permanently for the life of the patient. Alternatively or in combination, the device can be removed when no longer helpful or beneficial for treatment of the patient.

FIG. 1A-2 shows structures of therapeutic device 100 configured for placement in an eye as in FIGS. 1A-1, 1A-1-1 and 1A-1-2. The device may comprise retention structure 120 to couple the device 100 to the sclera, for example a protrusion disposed on a proximal end of the device. The device 100 may comprise a container 130 affixed to the retention structure 120. An active ingredient, for example therapeutic agent 110, can be contained within a reservoir 140, for example a chamber 132 defined by a container 130 of the device. The container 130 may comprise a porous structure 150 comprising a porous material 152, for example a porous glass frit 154, and a barrier 160 to inhibit release of the therapeutic agent, for example non-permeable membrane 162. The non-permeable membrane 162 may comprise a substantially non-permeable material 164. The non-permeable membrane 162 may comprise an opening 166 sized to release therapeutic amounts of the therapeutic agent 110 for the extended time. The porous structure 150 may comprise a thickness 150T and pore sizes configured in conjunction with the opening 166 so as to release therapeutic amounts of the therapeutic agent for the extended time. The container 130 may comprise reservoir 140 having a chamber with a volume 142 sized to contain a therapeutic quantity of the therapeutic agent 110 for release over the extended time. The device may comprise a needle stop 170. Proteins in the vitreous humor may enter the device and compete for adsorption sites on the porous structure and thereby may contribute to the release of therapeutic agent. The therapeutic agent 110 contained in the reservoir 140 can equilibrate with proteins in the vitreous humor, such that the system is driven towards equilibrium and the therapeutic agent 110 is released in therapeutic amounts.

The non-permeable material such as the non-permeable membrane 162, the porous material 152, the reservoir 140, and the retention structure 120, may comprise many configurations to deliver the therapeutic agent 110. The non-permeable membrane 162 may comprise an annular tube joined by a disc having at least one opening formed thereon to release the therapeutic agent. The porous material 152 may comprise an annular porous glass frit 154 and a circular end disposed thereon. The reservoir 140 may be shape-changing for ease of insertion; i.e., it may assume a thin elongated shape during insertion through the sclera and then assume an extended, ballooned shape, once it is filled with therapeutic agent.

The porous structure 150 can be configured in many ways to release the therapeutic agent in accordance with an intended release profile. The porous structure may comprise a single hole or a plurality of holes extending through a barrier material such as a rigid plastic or a metal. Alternatively or in combination, the porous structure may comprise a porous structure having a plurality of openings on a first side facing the reservoir and a plurality of openings on a second side facing the vitreous humor, with a plurality of interconnecting channels disposed therebetween so as to couple the openings of the first side with the openings of the second side, for example a sintered rigid material. The porous structure 150 may comprise one or more of a permeable membrane, a semi-permeable membrane, a material having at least one hole disposed therein, nano-channels, nano-channels etched in a rigid material, laser etched nano-channels, a capillary channel, a plurality of capillary channels, one or more tortuous channels, tortuous microchannels, sintered nano-particles, an open cell foam or a hydrogel such as an open cell hydrogel.

FIG. 1A-2-1 shows therapeutic device 100 loaded into an insertion cannula 210 of an insertion apparatus 200, in which the device 100 comprises an elongate narrow shape for insertion into the sclera, and in which the device is configured to expand to a second elongate wide shape for retention at least partially in the sclera.

FIG. 1A-2-2 shows a therapeutic device 100 comprising reservoir 140 suitable for loading in a cannula, in which the reservoir 140 comprises an expanded configuration when placed in the eye.

FIG. 1B shows therapeutic device 100 placed in an eye as in FIGS. 1A-1 and 1A-1-1. The device comprises retention structure 120 to couple to the sclera, for example flush with the sclera, and the barrier 160 comprises a tube 168. An active ingredient 112 comprising the therapeutic agent 110 is contained within tube 168 comprising non-permeable material 164. A porous structure 150 comprising a porous material 152 is disposed at the distal end of the tube 168 to provide a sustained release of the therapeutic agent at therapeutic concentrations for the extended period. The non-permeable material 164 may extend distally around the porous material 152 so as to define an opening to couple the porous material 152 to the vitreous humor when the device is inserted into the eye.

FIG. 1C shows a therapeutic device configured for placement in an eye as in FIGS. 1A-1 and 1A-1-1. An injectable formulation 190 of therapeutic agent 110 can be placed in therapeutic device 100 prior to placement in the eye. The formulation 190 can be injectable and may comprise therapeutic agent 110, a stabilizer 192, a binding agent 194 and erodible particles 196. The formulation 190 comprising stabilizer 192 and therapeutic agent 110 may be loaded into device 100 by injection into the device through an access port 180. The device 100 may comprise binding, leak, and barrier functions to deliver the therapeutic agent for the extended time. The stabilizer 192 and therapeutic agent 110 can be aspirated to replace the stabilizer and therapeutic agent. The stabilizer can be at least one of flushed or replaced when at least majority of the therapeutic agent has been released, such that additional therapeutic agent can be delivered from a second, injected formulation comprising the stabilizer and the therapeutic agent. A membrane 195 can be disposed over the periphery of the therapeutic device 100. The membrane 195 may comprise methylcellulose, regenerated cellulose, cellulose acetate, nylon, polycarbonate, poly(tetrafluoroethylene) (PTFE), polyethersulfone, and polyvinylidene difluoride (PVDF). The therapeutic device may comprise barrier 160 shaped such that opening 166 comprises an exit port. The therapeutic agent may be released through at least one of a diffusion mechanism or convection mechanism. The number, size, and configuration of exit ports may determine the release rate of the therapeutic agent. The exit port may comprise a convection port, for example at least one of an osmotically driven convection port or a spring driven convection port. The exit port may also comprise a tubular path to which the therapeutic agent may temporarily attach, and then be released under certain physical or chemical conditions.

FIG. 1C-A shows at least one exit port 167, the exit port can be disposed on the device 100 to allow liquid to flow from inside the device outward, for example when fluid is injected into an injection port 182 of the device or when an insert such as a glass frit is inserted into the device. The therapeutic device may comprise an access port 180 for injection and/or removal, for example a septum. Additionally or in the alternative, when the therapeutic device is refilled, the contents of the device may be flushed into the vitreous of the eye.

The access port 180 may be sized to receive an insert comprising a container having the therapeutic agent therein. For example, the porous structure 150 may comprise a container to contain a formulation 190 of the therapeutic agent as described herein, in which the container comprising porous structure 150 can be removed from the device 100 and replaced.

FIG. 1C-B shows a syringe being filled with a formulation 190 comprising therapeutic agent 110 and one or more of stabilizer 192, binding agent 194 or particles 196, for injection into the therapeutic device. The needle 189 coupled to syringe 188 of injector 187 can be used to draw formulation 190 comprising therapeutic agent 110, stabilizer 192, binding agent 194 and particles 196 from a container 110C. The container 110C may comprise a commercially available container, such as a bottle with a septum, a single dose container, or a container suitable for mixing formulations. A quantity 110V of therapeutic agent 110 can be drawn into injector 187 for injection into the therapeutic device 100 positioned within the eye. The quantity 110V may comprise a predetermined quantity, for example based on the volume of the container of the therapeutic device 110 and an intended injection into the vitreous humor. For example, the quantity 110V may exceed the volume of the reservoir container so as to inject a first portion of quantity 110V into the vitreous humor through the therapeutic device and to contain a second portion of quantity 110V within the reservoir container of the therapeutic device 110. Container 110C may comprise a formulation 190 of the therapeutic agent 110.

The formulation 190 may comprise formulations of therapeutic agent as described herein comprising therapeutic agent 110 and one or more of stabilizer 192, binding agent 194 or particles 196, for example therapeutic agents as described herein and with reference to Table 1A. The formulation 190 may comprise components of a concentrated or diluted formulation of a commercially available therapeutic agent, for example Avastin™. The osmolarity and tonicity of the vitreous humor can be within a range from about 290 to about 320 mOsm, for example, and the formulation can be substantially isotonic with one or more fluids of the body and within a range from about 250 to about 250 mOsm. For example, a formulation of Avastin™ may be diluted so as to comprise a formulation having an osmolarity and tonicity substantially similar to the osmolarity and tonicity of the vitreous humor, for example within a range from about 280 to about 340, for example about 300 mOsm. While the injectable formulation 190 comprising therapeutic agent 110, stabilizer 192, binding agent 194 and particles 196 may comprise an osmolarity and tonicity substantially similar to the vitreous humor, the formulation 190 may comprise a hyper osmotic solution relative to the vitreous humor or a hypo osmotic solution relative to the vitreous humor. The formulation and osmolarity of the therapeutic agent can be determined empirically to provide release of therapeutic agent for an extended time.

The formulation 190 may comprise components of a commercially available formulation such as Avastin™ or Lucentis™ combined with one or more of the stabilizer, the erodible particles, the surfactant, or the micelles as described herein, for example.

For example, in the United States, Avastin™ (bevacizumab) is approved as an anticancer drug and in clinical trials are ongoing for AMD. For cancer, the commercial solution is a pH 6.2 solution for intravenous infusion. Avastin™ is supplied in 100 mg and 400 mg preservative-free, single-use vials to deliver 4 mL or 16 mL of Avastin™ (25 mg/mL). The 100 mg product is formulated in 240 mg α,α-trehalose dihydrate, 23.2 mg sodium phosphate (monobasic, monohydrate), 4.8 mg sodium phosphate (dibasic, anhydrous), 1.6 mg polysorbate 20, and Water for Injection, USP. The 400 mg product is formulated in 960 mg α,α-trehalose dihydrate, 92.8 mg sodium phosphate (monobasic, monohydrate), 19.2 mg sodium phosphate (dibasic, anhydrous), 6.4 mg polysorbate 20, and Water for Injection, USP. The commercial formulations are diluted in 100 mL of 0.9% sodium chloride before administration and the amount of the commercial formulation used varies by patient and indication. Based on the teachings described herein, formulations of Avastin™ can be determined to inject into therapeutic device 100. In Europe, the Avastin™ formulation can be substantially similar to the formulation of the United States.

For example, in the United States, there are two forms of Triamcinolone used in injectable solutions, the acetonide and the hexacetonide. The acetamide is approved for intravitreal injections in the U.S. The acetamide is the active ingredient in TRIVARIS (Allergan), 8 mg triamcinolone acetonide in 0.1 mL (8% suspension) in a vehicle containing w/w percents of 2.3% sodium hyaluronate; 0.63% sodium chloride; 0.3% sodium phosphate, dibasic; 0.04% sodium phosphate, monobasic; and water, pH 7.0 to 7.4 for injection. The acetamide is also the active ingredient in Triesence™ (Alcon), a 40 mg/ml suspension.

Osmolarity for these formulations can be determined. The degree of dissociation of the active ingredient in solution can be determined and used to determine differences of osmolarity from the molarity in these formulations. For example, considering at least some of the formulations may be concentrated (or suspensions), the molarity can differ from the osmolarity.

The formulation of therapeutic agent injected into therapeutic device 100 may comprise many known formulations of therapeutic agents modified in accordance with variations described herein, and the formulation therapeutic agent may comprise an osmolarity suitable for release for an extended time from device 100. Table 2 shows examples of osmolarity (Osm) of saline and some of the commercially formulations of Table 1A can be modified in accordance with the variations described herein.

TABLE 2

Summary of Calculations

| Description | Osm (M) |
| --- | --- |
| Saline (0.9%) | 0.308 |
| Phosphate Buffered Saline (PBS) | 0.313 |
| Lucentis ™ | 0.289 |
| Avastin ™ | 0.182 |
| Triamcinolone Acetonide (Trivaris-Allergan) | 0.342 |
| Triamcinolone Acetonide (Triessence-Alcon) | Isotonic* |
| Triamcinolone Acetonide (Kenalog-Apothecon) | Isotonic* |

*As described in package insert

The vitreous humor of the eye comprises an osmolarity of about 290 mOsm to about 320 mOsm. Formulations of therapeutic agent having an osmolarity from about 280 mOsm to about 340 mOsm are substantially isotonic and substantially iso-osmotic with respect to the vitreous humor of the eye. Although the formulations listed in Table 2 are substantially iso-osmotic and isotonic with respect to the vitreous of the eye and suitable for injection into the therapeutic device, the formulation of the therapeutic agent injected into the therapeutic device can be hypertonic (hyper-osmotic) or hypotonic (hypo-osmotic) with respect to the tonicity and osmolarity of the vitreous. Work in relation to variations suggests that a hyper-osmotic formulation may release the active ingredient of the therapeutic agent into the vitreous somewhat faster initially when the solutes of the injected formulation equilibrate with the osmolatiry of the vitreous, and that a hypo-osmotic formulation such as Avastin™ may release the active ingredient of the therapeutic agent into the vitreous somewhat slower initially when the solutes of the injected formulation equilibrate with the eye. The appropriate reservoir chamber volume and porous structure for a formulation of therapeutic agent disposed in the reservoir chamber can be determined so as to release therapeutic amounts of the therapeutic agent for an extended time and to provide therapeutic concentrations of therapeutic agent in the vitreous within a range of therapeutic concentrations that is above the minimum inhibitory concentration for the extended time.

FIG. 2 shows an access port 180 suitable for incorporation with the therapeutic device 100. The access port 180 may be combined with the therapeutic devices described herein. The access port may be disposed on a proximal end of the device. The access port 180 may comprise an opening formed in the retention structure 120 with a penetrable barrier 184 comprising a septum 186 disposed thereon. The penetrable barrier can receive the needle 189 sized to pass the formulation 190 as described herein. The access port may 180 be configured for placement under the conjunctiva 16 of the patient and above the sclera 24.

Figure 3A:
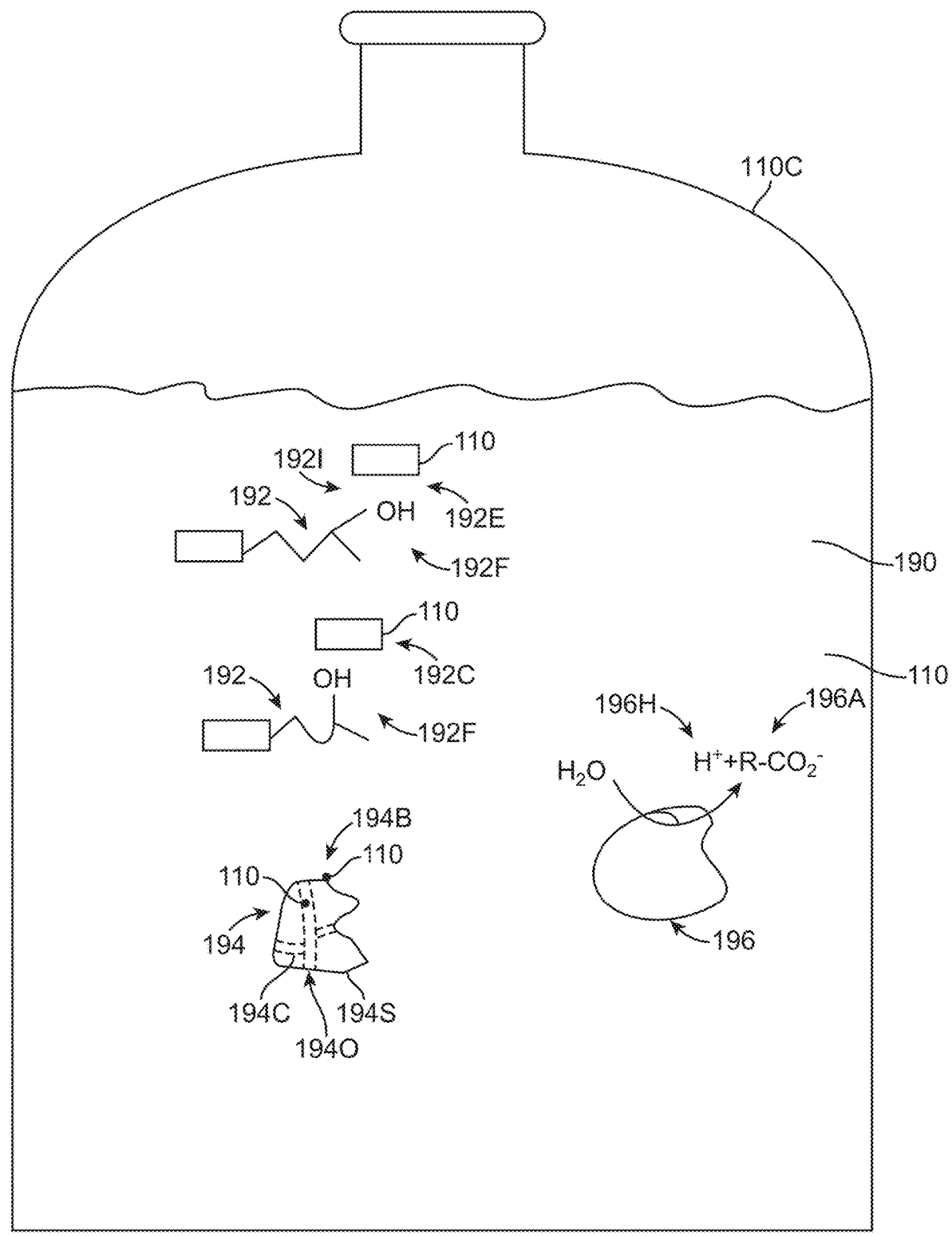
FIG. 3A shows components of a formulation comprising therapeutic agent, stabilizer corresponding to the therapeutic agent, binding agent and erodible particles, in accordance with variations described herein.

FIG. 3A shows components of formulation 190 comprising therapeutic agent, stabilizer 192 corresponding to the therapeutic agent, reversible binding agent 194 and erodible material 196. The stabilizer 192 may comprise at least about 20% of the weight of the therapeutic agent, such that diffusion of the stabilizer corresponds at least partially to diffusion of the therapeutic agent. The reversible binding agent 194 may comprise a plurality of particles of binding agent. The erodible material 196 may comprise a plurality of particles.

The stabilizer 192 can interact with the therapeutic agent 110 in one or more of many ways so as to decrease degradation of the therapeutic agent. For example, the therapeutic agent 110 may comprise protein such as a Fab antibody fragment or a derivative thereof, and the stabilizer 192 may comprise one or more hydrophilic functional groups 192F that promote protein stabilization by a co-solvent effect. Alternatively or in combination, the stabilizer 192 may form a complex 192C with the therapeutic agent 110.

The stabilizers having the molecular weights as described herein can be particularly well suited to provide stabilization of the therapeutic agent comprising protein with the co-solvent effect, for example co-solvent stabilization of ranibizumab protein. A protein solvent effect as described by Arakawa et al., *Adv Drug Delivery Reviews*, 10(1993) 1-28, can be modified and/or combined in accordance with variations as described herein. In many variations, there can be a decreased amount of the stabilizing co-solute in the immediate vicinity of the therapeutic agent comprising protein relative to bulk solution such that the therapeutic agent comprising protein is preferentially hydrated. For example, the co-solutes can be preferentially excluded from contact with the surface of the therapeutic agent comprising protein so as to preferentially hydrate the therapeutic agent comprising protein. Although the exclusion can be entropically unfavorable, the thermodynamic penalty for exclusion can be even higher for protein in the denatured state due to the larger exposed surface area of the denatured protein. The lower penalty for the native versus denatured therapeutic agent comprising protein can result in stabilization of the therapeutic agent comprising protein, for example with the high molecular weight stabilizers of at least 2 k Daltons as described herein. Similar stabilization may be provided with micelles comprising stabilizer having hydrophilic functional groups as described herein, for example.

The stabilizer 192 may comprise one or more functional groups 192F, for example one or more hydroxyl groups, so as to form a complex 192C with the therapeutic agent 110. The dynamics of complex formation and dissociation may be slowed down when the stabilizer has more than one functional group interacting with the therapeutic agent at the same time. Hence, larger molecular weight stabilizers may have multiple interactions, which may slow the diffusion and depletion of stabilizer present in the device reservoir, so as to provide a formulation having improved stability.

The binding agent 194 may comprise a plurality of binding sites to bind reversibly the therapeutic agent 110.

The reversible binding 194B can be pH sensitive. The binding agent 194 may comprise a plurality of channels 194C and an outer surface 194S. The plurality of channels 194C can extend from an opening 194O of the surface 194S substantially through the particle of the binding agent 194. The therapeutic agent 110 can be bound reversibly to an inner surface of channel 194C or outer surface 194S. The particle of binding agent 194 may comprise a resin having derivatized inner and outer surfaces so as to bind reversibly to therapeutic agent 110. The formulation 190 may comprise a plurality of the particles of binding agent and may comprise one or more of a suspension or a slurry.

The erodible material 196 may comprise a plurality of particles of the erodible material. The erodible material 196 may comprise an erodible polymer such as one or more of PLA, PGA or PLA/PGA copolymer (hereinafter "PLGA"). The polymer can erode with hydrolysis so as to provide a proton 196H of an acid 196A. The hydrolysis may comprise hydrolysis of ester linkages so as to provide one proton per linkage hydrolyzed.

FIG. 3B1 shows a stabilizer as in FIG. 3A. The stabilizer may comprise one or more of an alcohol, a polyol, a phenol, a carbohydrate, a sugar (sucrose, lactose, and glucose), amino acids (glycine, alanine, and proline), or amines (betaine and trimethylamine N-oxide), for example. The stabilizer may comprise a molecular weight corresponding to the therapeutic agent, for example at least about 20% of the molecular weight of the therapeutic agent. The molecular weight can be sufficient such that a portion of the stabilizer remains in the device 100 when a portion of the therapeutic agent is released so as to stabilize a remaining portion of the therapeutic agent. The stabilizer 192 may comprise a high molecular weight polymer 192P, for example at least about 2 k Daltons. The stabilizer may comprise one or more forms of cellulose (e.g., carboxymethylcellulose, hydroxyethyl cellulose, hydroxypropyl cellulose, hydroxypropyl methylcellulose, methylcellulose), chitin (e.g., chitosan), other oligosaccharides and polysaccharides, or polymeric forms of amino acids.

The diffusion constant of the stabilizer can be determined, for example based on an estimate of hydrodynamic radius corresponding to the cube root of the molecular weight as described herein.

Table ZZZ shows diffusion co-efficients and estimates of device half-life relative to Ranibizumab.

| Diffusion relative to Ranibizumab | | | | | | | | |
|---|---|---|---|---|---|---|---|---|
| Compound | MW | Temp C. | Diff Coeff (cm^2/s) | Equiv diameter assumes unit density and is the diameter per molecule | | | | |
| Ranibizumab | 48,000 | 37 | 1.0E−06 | | | | | |

| Example Compound | MW | mW/ (Ran MW) | D/ (Ran D) | Diff Coeff (cm^2/s) | Device Half-life relative to Ranibiz. | Equiv volume (nm^3) | Equiv diameter (nm) | % In device at TA Half-life |
|---|---|---|---|---|---|---|---|---|
| Histidine | 156 | 0.003 | 6.75 | 6.8E−06 | 0.15 | 0.3 | 0.8 | 0.9 |
| Trehalose | 378 | 0.008 | 5.03 | 5.0E−06 | 0.20 | 0.6 | 1.1 | 3.1 |
|  | 500 | 0.010 | 4.58 | 4.6E−06 | 0.22 | 0.8 | 1.2 | 4.2 |
|  | 1000 | 0.021 | 3.63 | 3.6E−06 | 0.28 | 1.7 | 1.5 | 8.1 |
| Polysorbate 20 | 1227 | 0.026 | 3.39 | 3.4E−06 | 0.29 | 2.0 | 1.6 | 9.5 |
|  | 2000 | 0.042 | 2.88 | 2.9E−06 | 0.35 | 3.3 | 1.9 | 13.5 |
|  | 5000 | 0.104 | 2.13 | 2.1E−06 | 0.47 | 8.3 | 2.5 | 22.9 |
|  | 10000 | 0.208 | 1.69 | 1.7E−06 | 0.59 | 16.6 | 3.2 | 31.1 |
|  | 20000 | 0.417 | 1.34 | 1.3E−06 | 0.75 | 33.2 | 4.0 | 39.5 |
|  | 30,000 | 0.625 | 1.17 | 1.2E−06 | 0.85 | 49.8 | 4.6 | 44.5 |
| Ranibizumab | 48,000 | 1.000 | 1.00 | 1.0E−06 | 1.00 | 79.7 | 5.3 | 50.0 |
|  | 50,000 | 1.042 | 0.99 | 9.9E−07 | 1.01 | 83.0 | 5.4 | 50.5 |
| BSA | 66,000 | 1.375 | 0.90 | 9.0E−07 | 1.11 | 109.6 | 5.9 | 53.6 |
|  | 100,000 | 2.083 | 0.78 | 7.8E−07 | 1.28 | 166.1 | 6.8 | 58.1 |
| Bevacizumab | 149,000 | 3.104 | 0.69 | 6.9E−07 | 1.46 | 247.4 | 7.8 | 62.2 |
|  | 200,000 | 4.167 | 0.62 | 6.2E−07 | 1.61 | 332.1 | 8.6 | 65.0 |
|  | 500,000 | 10.417 | 0.46 | 4.6E−07 | 2.18 | 830.3 | 11.7 | 72.8 |
|  | 1,000,000 | 20.833 | 0.36 | 3.6E−07 | 2.75 | 1660.6 | 14.7 | 77.7 |
|  | 2,500,000 | 52.083 | 0.27 | 2.7E−07 | 3.73 | 4151.4 | 19.9 | 83.1 |
|  | 3.94E+07 | 8.E+02 | 1.1E−01 | 1.1E−07 | 9.4 | 6.5E+04 | 50.0 | 92.9 |
|  | 3.15E+08 | 7.E+03 | 5.3E−02 | 5.3E−08 | 18.7 | 5.2E+05 | 100 | 96.4 |
|  | 2.52E+09 | 5.E+04 | 2.7E−02 | 2.7E−08 | 37.5 | 4.2E+06 | 200 | 98.2 |
|  | 3.94E+10 | 8.E+05 | 1.1E−02 | 1.1E−08 | 93.6 | 6.5E+07 | 500.0 | 99.3 |
|  | 3.15E+11 | 7.E+06 | 5.3E−03 | 5.3E−09 | 187.3 | 5.2E+08 | 1000.0 | 99.6 |
|  | 2.52E+12 | 5.E+07 | 2.7E−03 | 2.7E−09 | 374.6 | 4.2E+09 | 2000.0 | 99.8 |
|  | 3.94E+13 | 8.E+08 | 1.1E−03 | 1.1E−09 | 936.4 | 6.5E+10 | 5000.0 | 99.9 |

Table ZZZ shows that the molecular weight, diffusion co-efficient, equivalent diameter of ranibizumab is about 48 k Daltons, 1.0E-6, and 5.3 nm, respectively.

The molecular weight of the stabilizer can be provided in 1 k Dalton increments from about 1 k Dalton to about 200 k Daltons and provide in a Table having about 200 rows similar to Table ZZZ. The parameters of Table ZZZ determined such as the half-life in the device, the equivalent volume, the equivalent diameter, and % in the device at the half-life of the therapeutic agent 110. The table may comprise a row for each molecular weight in 1 k Dalton increments, and the % of stabilizer in the device compared with the therapeutic agent 110. The table may include columns for two half-lives of the therapeutic agent, three half-lives of the therapeutic agent, four half-lives of the therapeutic agent, and the corresponding percentage of stabilizer remaining in the device.

The Percentage at 1, 2, 3, 4 5, and 6 Half-Lives can be Determined.

The molecular weight, diffusion coefficient and equivalent diameter of trehalose is about 0.4 k Daltons, 5.0E-6, and 1.1 nm, respectively. The relative molecular weight of trehalose to ranibizumab is about 0.8%, and the relative half-life of trehalose in device 100 is about 20% of ranibizumab. The relative amount of trehalose remaining in therapeutic device 100 at the half-life of ranibizumab is about 3.1%. This decreased half-life of trehalose and amount in the device 100 relative to ranibizumab is related to the decreased molecular weight of trehalose relative to ranibizumab.

A disaccharide such as trehalose can be combined with one or more of micelles or polymeric proteins as described herein, so as to associate with the one or more of the micelles or the polymeric proteins so as to decrease a rate of release of the disaccharide from the reservoir chamber.

The molecular weight, diffusion coefficient and equivalent diameter of polysorbate 20 is about 1.2 k Daltons, 3.4E-6, and 1.6 nm, respectively. The relative molecular weight of polysorbate to ranibizumab is about 2.6%, and the relative half-life of polysorbate 20 in device 100 is about 29% of ranibizumab. The relative amount of polysorbate 20 remaining in therapeutic device 100 at the half-life of ranibizumab is about 9.5%. This decreased half-life of polysorbate and amount in the device 100 relative to ranibizumab is related to the decreased molecular weight of polysorbate relative to ranibizumab.

The diffusion coefficients of Table ZZZ can be determined based on weight for molecular weights up to about 2.5 M Daltons, and based on size above about 2.5 M Daltons.

The stabilizer may comprise a molecular weight that is at least about 10% of the molecular weight of the therapeutic agent; such that the half-life of the stabilizer corresponds to at least about 50% of the half-life of the therapeutic agent. For example, a stabilizer 192 with a molecular weight of about 5 k Daltons corresponding to about 10% of the molecular weight of ranibizumab, the relative half life of the stabilizer is about half (0.47) of the half life of ranibizumab. When the half-life of the stabilizer is about half that of the therapeutic agent, about ¼ of the stabilizer may remain in the therapeutic device for an extended time corresponding to the half-life of the therapeutic agent. For example, when the half-life of the therapeutic agent ranibizumab in the device is about 100 days, about ¼ of a 5 k Dalton molecular weight stabilizer will remain in the therapeutic device.

The stabilizer may comprise a molecular weight that is at least about 20% of the molecular weight of the therapeutic agent, such that the half life of the stabilizer corresponds to at least about 50% of the half life of the therapeutic agent. At a time of two half lives post-placement in the therapeutic device, the relative proportion of stabilizer to therapeutic agent is about 1 to 4. This amount of stabilizer is sufficient to stabilize the therapeutic agent in many variations.

FIG. 3B2 shows a micelle 192M of a stabilizer as in FIG. 3A. The stabilizer 192 may comprise a micelle 192M of the stabilizer 192. The micelle 192M may comprise a weight corresponding to a molecular weight of the therapeutic agent, such that a substantial portion of the micelles of the injected formulation remain in the reservoir chamber of the therapeutic device when the therapeutic agent is released. The weight of each micelle may correspond to a molecular weight of at least about 10% of the therapeutic agent, for example at least about 20%, such that the micelle comprises a size so as to inhibit diffusion of the micelle from the reservoir chamber through the porous structure 150.

The micelle 192M may comprise a reservoir of the stabilizer. For example, the stabilizer may comprise a first micelle portion and a second solution portion. The second solution portion may comprise a portion of the surfactant molecule dissolved as a solute in solution. The second solution portion may correspond to a critical micelle concentration (hereinafter "CMC"). Above this critical threshold concentration, additional surfactant added to the solution may be present in the form of micelles. The micelle portion can remain substantially within the reservoir chamber based on the size and weight of the micelle as described herein. In many variations, each of the micelles may comprise 50 or more surfactant molecules, in which each surfactant molecule comprises a molecular chain. The diffusion coefficient of a micelle of this size may have a weight and corresponding diffusion coefficient equal or larger than the therapeutic agent, for example. As individual molecules of the stabilizer in solution diffuse through the porous structure 150, the micelle can release stabilizer into solution such that the concentration of stabilizer in solution remains substantially constant. The micelles may comprise polymeric surfactants that may comprise a first micelle portion and a second solution portion in equilibrium, such that as the second portion comprising molecules dissolved in solution diffuses through the porous structure the polymeric surfactant on the micelles is released into solution so as to maintain the concentration of polymeric surfactant in solution.

The surfactant may comprise one or more of polysorbates (for example, polysorbate 20 and polysorbate 80, also known as Tween 20 and Tween 80), block copolymers of ethylene oxide or propylene oxide of various sizes marketed by BASF as Pluronic®, or ethoxylated emulsifiers marketed by BASF as Cremophor®, and combinations thereof.

The surfactant may increase the stability of the therapeutic agent by occupying interfaces so as to displace therapeutic agent comprising protein from the interfaces. The interface may comprise an inner surface of the reservoir chamber exposed to the formulation such that the inner surface may interact with the protein, for example an inner surface housing or a surface of the porous structure 150. Proteins may undergo conformational changes at interfaces that may then lead to degradation via any of a number of pathways such as aggregation, deamidation, oxidation, etc. The surfactant may compete with and displace protein at air-liquid interfaces such as at the surface of a bubble or liquid-solid interfaces such as with displacement of the protein at the exposed surface inside a porous structure within the device. High concentrations of surfactant, near or beyond the CMC may be helpful so as to substantially displace protein from interfaces and inhibit interaction of the protein with the inner surfaces of device 100. In many variations, the surfactant concentration within the reservoir chamber of the device can be maintained near or above the CMC for an extended time as described herein.

The CMC can be determined from a variety of techniques such as measurements of surface tension using a Wilhelmy plate. The CMC for a particular surfactant may be dependent on a variety of parameters such as the concentrations of other components in the formulation and the temperature. Values ranging from 1E-5 to 8E-5 are reported in the literature for polysorbate 20.

Table K1 shows amounts of polysorbate 20 sufficient to maintain the presence of micelles in representative devices for an extended time of at least about 6 months, such that the concentration of surfactant stabilizer in device 100 is at least about the CMC of the surfactant stabilizer comprising Polysorbate 20. The diffusion coefficients of 3.4E-6 and 8.8E-7 cm2/s for the single molecule (corresponding to the second portion) and the micelle (corresponding to the micelle portion), respectively, are obtained based upon molecular weight of 1227 for polysorbate 20 and assuming a plurality of approximately 50 molecules of polysorbate 20 per micelle, in which each of the 50 molecules comprises a molecular chain such as a polymeric chain. The corresponding particle weight of the micelle comprising the plurality of 50 polysorbate 20 molecules can be about 61,350, so as to correspond to a diffusion coefficient about 3.86 lower than Polysorbate 20, based on the cube root of the weight of the micelle particle relative to the weight of the individual Polysorbate 20 molecule (cube root of 50 is about 3.86). The examples show polysorbate 20 concentrations 6 or more times larger than the CMC can be sufficient so as to maintain micelles in the device at least about 6 months after placement of the therapeutic agent and micelles in device 100. In many variations, concentrations of at least about 0.04% may be sufficient so as to maintain concentration of micelles above the CMC.

TABLE K1

Minimum concentration of polysorbate 20 sufficient to maintain micelles in device 100, as a function of CMC and device parameters.

| | CMC (M) | | | |
|---|---|---|---|---|
| | 1e-5 | 8e-5 | 1e-5 | 8e-5 |
| CMC (wt %) | 0.001% | 0.01% | 0.001% | 0.01% |
| Device RRI (mm) | 0.02 | 0.02 | 0.06 | 0.02 |
| Device Volume (uL) | 25 | 25 | 25 | 100 |
| Minimal Conc. to replenish single chain diffusion (wt %) | 0.005% | 0.042% | 0.016% | 0.042% |
| Half-life of Therapeutic Agent Ranibizumab (days) | 100 | 100 | 30 | 400 |
| Minimal Conc. corresponding to micelle diffusion (wt %) | 0.004% | 0.029% | 0.033% | 0.013% |
| Total Minimal Conc. (wt %) | 0.009% | 0.071% | 0.048% | 0.054% |
| Ratio of Total Minimal Conc. to CMC | 7 | 7 | 40 | 6 |

Table K1 shows that substantial amounts of surfactant can be provided for an extended time of at least about 6 months so as to stabilize the therapeutic agent within device 100. In many variations, ranibizumab can be delivered in therapeutic amounts for an extended time of at least about 6 months when therapeutic device 100 comprises a half-life of at least about 90 days or more, for example.

The amount of surfactant in device 100 can be combined with an amount of one or more of many therapeutic agents 110 as described herein. The half life of the therapeutic agent may correspond to the amount of surfactant sufficient to maintain the concentration of surfactant above the CMC.

The amount of surfactant to provide for an intended extended time can be determined empirically. For example, the above table shows amounts of surfactant sufficient to provide surfactant above the CMC for 6 months. Similar tables for a target intended time of 12 months, for example, can be determined.

Alternatively or in combination, amounts of surfactant can be determined to provide concentrations above the CMC for an intended extended time. For example, to achieve a surfactant concentration above the CMC for an extended time of about one year, the minimal concentration corresponding to micelle diffusion can be increased by about 4× when the intended time is increased by about 2×, so as to provide micelles within device 100 for at least about 1 year, for example. With device 100 having a reservoir chamber volume of 100 uL and an RRI of about 0.02, to achieve micelles for at least about one year with a CMC of 0.01%, the concentration of Polysorbate 20 corresponding to micelle diffusion can be increased from about 0.013% to about 0.017%, and the concentration of Polysorbate 20 corresponding to individual surfactant molecule diffusion can be increased from about 0.04% to about 0.08%, such that the total concentration of Polysorbate 20 comprises about 0.1%.

The micelle 192M may form a complex 192C with the therapeutic agent 110. Alternatively or in combination, the chains of individual molecules may associate with the therapeutic agent, for example form a complex with the therapeutic agent.

Figure 3C:
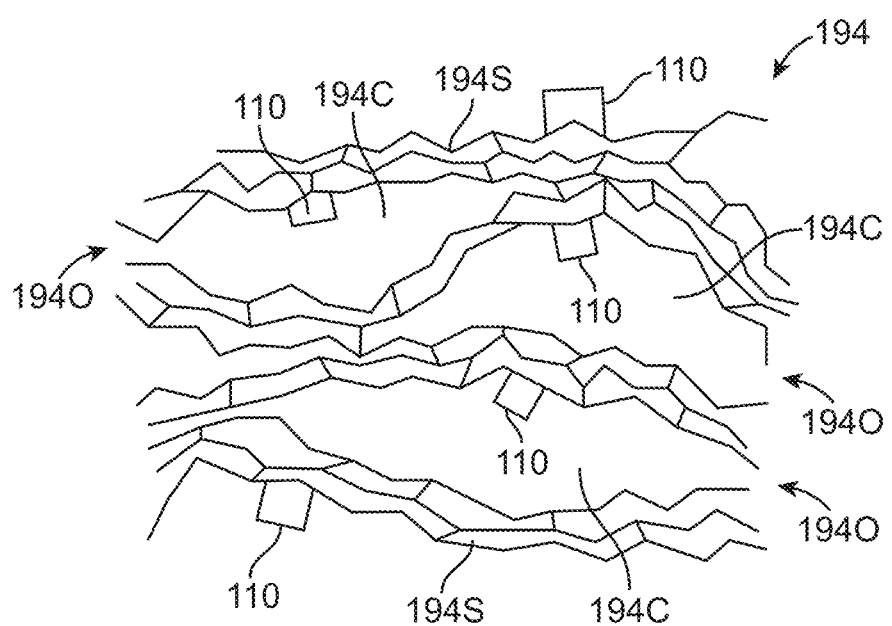
FIG. 3C shows a binding agent having porous channels as in FIG. 3A, in accordance with variations described herein.

FIG. 3C shows a particle of a binding agent having porous channels as in FIG. 3A. The particle may comprise a plurality of channels and a plurality of openings sized to allow the therapeutic agent 110 to diffuse along the channel 194C and out opening 194O. The porous channels may comprise the derivatized surface as described herein.

Figure 3D:
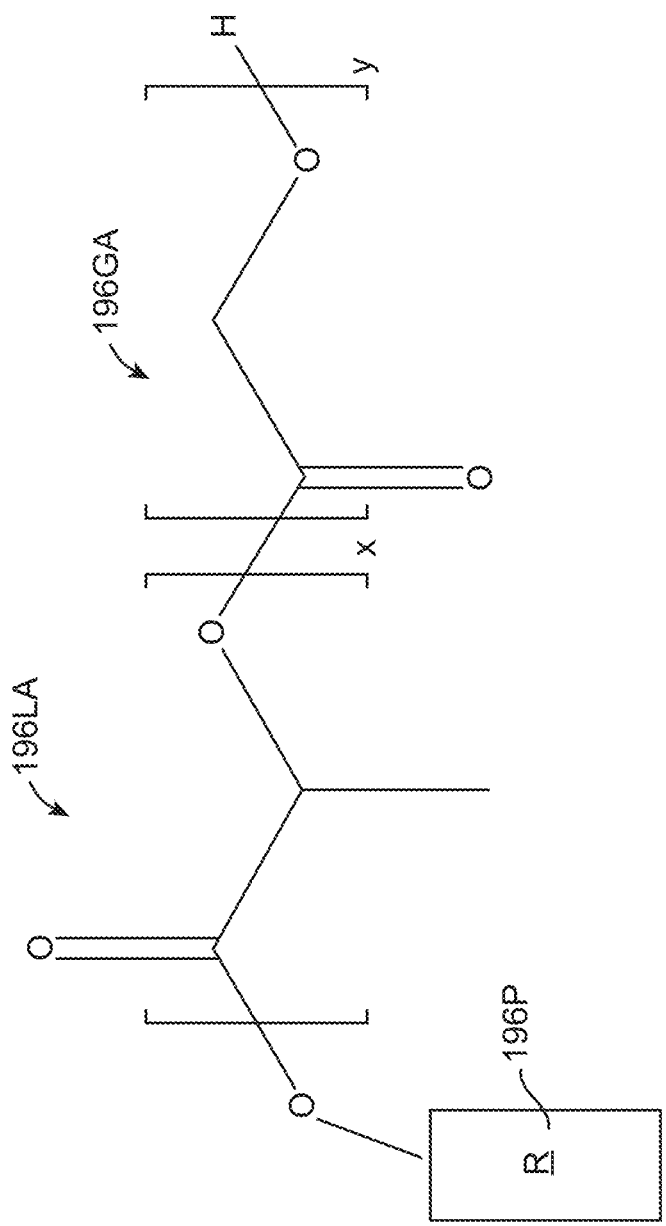
FIG. 3D shows an erodible material comprising an erodible polymer to generate a proton of an acid as in FIG. 3A, in accordance with variations described herein.

FIG. 3D shows an erodible material comprising an erodible polymer to generate a proton of an acid as in FIG. 3A. The polymer may comprise one or more of polylactic acid 196LA or polyglyoclic acid 196GA, or combinations thereof, for example. The polymer may comprise many biodegradable erodible materials, such as polycaprolactone, for example. The particle may comprise a substantial polymer chain 196P, such that the particle is sized so as to inhibit diffusion of the particle through the porous structure to release the proton of the acid within the reservoir chamber of the therapeutic device 100.

The proton generation based on erodible material such as biodegradable polymers comprising PLGA can be provided in many ways. In many variations, therapeutic agent is located in the fluid surrounding the erodible particles, and may not be encapsulated inside of the particles such that the protons released from the particle can be diluted with the fluid surrounding the erodible particle.

The rate of proton generation can be determined by the composition of the particles. Variables capable of modulating the degradation of PLGA can include one or more of a ratio of PLA to PGA, molecular weight, crystallinity, particle size, porosity, and pore size distributions, shape, and processing conditions. For example, increasing the ratio of PLA to PGA can decrease the rate of degradation, and decreasing the ratio of PLA to PGA can increase the rate of degradation. Providing particles with lower porosity may reduce the fraction of water filled pores and can result in a lower erosion rate. Increasing molecular weight, crystallinity, and particle size may decrease degradation rates and the rate of proton production.

PLGA particles prepared for encapsulation and delivery of drugs may achieve drug release for extended periods on the order of weeks or months. However, water-soluble drug can be substantially depleted from PLGA particles before the polymer is completely degraded. Hence, protons may be supplied from erosion of PLGA for several months beyond the time sustained drug delivery is achieved. Furthermore, PLGA intended as proton generators can have lower porosity during the erosion process if they do not have additional pores forming from depletion of encapsulated drug. Hence, biodegradable particles for proton generation may be prepared where protons are generated for periods of a year or longer.

The erodible particles may be coated with an excipient that dissolves slowly in water, so as to delay the time when the biodegradable material is hydrated and so as to delay the corresponding erosion process. The erodible particles may comprise enteric coatings. The enteric coatings can remain intact at slightly acidic conditions and dissolve when pH is increased toward physiological pH, such that proton generation can be started at a time post injection when pH has risen above a targeted threshold. The time profile of the release of the protons of the acid can be determined based on a mixture of the particles. For example, the time profile of proton generation may be modulated by using a mixture of particles with varying properties, for example, varying particle size or thickness of the enteric coating.

Coatings with slow dissolution may comprise polymers with limited solubility in water, such as ethylcellulose, and may be mixed with polymers (e.g., hydroxyethylcellulose, sodium carboxymethylcellulose, methyl hydroxyethylcellulose) that are soluble in water to achieve the desired dissolution profile. The coatings may also comprise polymers with lower critical solution temperatures, such as methylcellulose, hydroxypropyl cellulose, and hydroxypropyl methylcellulose, that are insoluble at high temperature and have dramatically increased solubility in cold water. The desired dissolution profile may be achieved by selection of molecular weights (e.g., increase in molecular weight decreases solubility and dissolution rate) and by mixing with other soluble and insoluble polymers and excipients.

Commonly used enteric coating polymers are shown in Table XX. These may be combined with the coatings above.

TABLE XX

Enteric Coating Polymers

| Polymer | Solubility Profile |
|---|---|
| Shellac | Above pH 7 |
| Cellulose acetate phthalate (CAP) | Above pH 6 |
| Polyvinylacetate phthalate (PVAP) | Above pH 5 |
| Hydroxypropyl methylcellulose phthalate (HPMCP) | Above pH 4.5 |
| Polymers of methacrylic acid and its esters | Above pH 6 |

The above polymers used as coatings may also serve as a protein stabilizer once dissolved into the solution inside the device. These coatings may stabilize the therapeutic agent by forming a complex with the therapeutic agent or may stabilize by acting as a co-solute.

Stabilizers larger than 2 kDa may have sufficiently limited solubility to be present as a suspension in the formulation (e.g., ethylcellulose, methylcellulose, hydroxypropyl cellulose, and hydroxypropyl methyl cellulose). For example, small particles of these polymers could be prepared by micronization and milling, or by emulsion or spray drying techniques.

Coatings that delay dissolution, whether pH triggered or not, may also be used with other solid reservoirs of stabilizers that replenish stabilizer as it is depleted and delivered to the vitreous. For example, micronized trehalose could be coated for delayed dissolution.

The erodible material to generate the proton of the acid and stabilizers to decrease degradation of the therapeutic agent can be combined in many ways. For example, formulation stabilizers, such as buffers and sugars, may be encapsulated in biodegradable particles so as to release a second portion of stabilizer that replenishes a first portion stabilizer that has been released into the vitreous. For example, as trehalose is stable at acidic conditions, the erodible particles may comprise trehalose stabilizer and the erodible material. Alternatively or in combination, the erodible particles may comprise buffer so as to release the buffer with erosion of the particles. The buffer may comprise one or more buffers including, for example, acetate, succinate, gluconate, histidine, citrate, and organic acid buffers. The stabilizer may also comprise pH modulators such as chloride salts.

Table Z1 to Table Z5 shows amounts of PLGA polymer to provide a pH of about 5.5 for an extended time of at least about 1 year. These tables include calculations for the flux of protons out of the device 100, and also calculations of physiological phosphate into the device, so as to determine amounts of erodible polymer based on diffusion of vitreous buffer into device 100.

TABLE Z1

Molecular weights of PGA, PLA and PLGA

| MW of repeat unit | |
|---|---|
| PGA | 58 |
| PLA | 76 |
| Ave. | 67 |

As shown in Table Z1, PGA and PLA have molecular weights of 58 and 76 respectively, with an average of about 67 k Daltons. These molecular weights correspond to about 67 mg per mmole of PLGA.

TABLE Z2

Phosphate pKa's and concentrations in the vitreous humor.

| Phosphate | |
|---|---|
| pKa2 | 7.21 |
| Ka2 | 6.17E−08 |
| Phosphate (M) | 0.01 |

Table Z2 shows the pKa2 of phosphate to be about 7.21, and the Ka2 to be about 6.17E08. The molarity of the phosphate buffer is about 0.1, which corresponds to the vitreous humor and many bodily fluids, for example blood. After an amount of time within a range from about two weeks to about three months, a formulation with a small molecular weight buffer (e.g., histidine) may be depleted in the reservoir of the device. At that time, the reservoir may be in substantial equilibrium with the buffers in the vitreous (e.g., phosphate) and comprise physiological concentrations of the vitreous buffers.

TABLE Z3

The change of H2PO4 concentration and corresponding pH's

| pH | [H+] | pOH | [OH−] | HPO4/H2PO4 | H2PO4 (M) | HPO4 (M) | Extra H+ (M) |
|---|---|---|---|---|---|---|---|
| 5.5 | 3.16E−06 | 8.5 | 3.16E−09 | 0.02 | 0.00981 | 0.00019 | 0.0059 |
| 7.4 | 3.98E−08 | 6.6 | 2.51E−07 | 1.55 | 0.00392 | 0.00608 | |

The pH within the device can be about 5.5, and the pH of the vitreous humor can be about 7.4. Addition of phosphate into a device at pH 5.5 may change the pH of the device unless additional protons are provided. Table Z3 shows information on the concentrations of phosphate species at the vitreous and device pH values, to enable calculation of the amount of protons required to maintain pH in the device in the presence of 0.1 M phosphate. The corresponding [H+], pOH, and [OH—] values are shown. The ratio of $[HPO_4^{2-}]$ to $[H_2PO_4^-]$ is shown to be 0.02 and 1.55 for pH 5.5 and 7.5, respectively. The corresponding molarities (M) of $H_2PO_4^-$, $HPO_4^{2-}$, and extra proton to decrease the pH are shown.

TABLE Z3

RRI, reservoir volume and density

| | |
|---|---|
| RRI (mm) | 0.02 |
| Reservoir vol (uL) | 25 |
| Density of PLGA (mg/uL) | 1 |

Table Z3 shows an example of a device having an RRI of 0.02 and reservoir volume of 25 uL. The density of PLGA is about 1 mg/ul.

The half-life of Lucentis™ in device 100 having the RRI of 0.02 and reservoir volume of 25 uL is about 100 days, as described in U.S. Pub. No. 2010/0255061, the full disclosure of which has been previously incorporated by reference and suitable for combination in accordance with variations described herein.

TABLE Z4

PLGA to preplace H+ that diffuses across the porous structure 150, also referred to as rate control element (hereinafter "RCE").

PLGA to replace H+ that diffuses out across RCE

| | H+ | OH− | |
|---|---|---|---|
| Diffusion Coeff (cm^2/s) | 9.31E−05 | 5.28E−05 | Source: Cussler, E. L., "Diffusion", *Cambridge University Press*, first edition, 1984, pg 147 |
| Conc in Reservoir (M) | 3.16E−06 | 3.16E−09 | |
| Conc in Receiver (M) | 3.98E−08 | 2.51E−07 | |
| Conc Change across RCE (M) | 3.12E−06 | −2.48E−07 | |
| Rate (mmole/day) | 5.02E−08 | −2.26E−09 | Assume amount of OH− transported is negligible compared to H+ |
| Rate (mmole/month) | 1.51E−06 | | |
| Rate (mmole/year) | 1.83E−05 | −8.26E−07 | |
| Rate (ug PLGA/year) | 1.23 | | |
| Rate (uL PLGA/year) | 1.23E−03 | | |
| Volume fraction | 0.005% | | |

Table Z4 shows that erosion of about 1.23E−03 ug of PLGA per year corresponds to the diffusion of H+ ions across porous structure 150. The corresponding volume fraction is about 0.005% of the 25 uL volume. The diffusion coefficient of H+ proton ions in solution is about 9.31E−05.

Table Z5 shows PLGA to protonate phosphate that diffuses into device 100 across porous structure 150 from a bodily fluid such as the vitreous humor.

PLGA required to protonate phosphate (change of pH from 7.4 to 5.5 or value set above). Assumes all histidine buffer has diffused out of the device and device now contains phosphate at concentrations in equilibrium with the vitreous (0.01M)

| | H+ | |
|---|---|---|
| Extra H+ (M) | 0.0059 | |
| Extra H+ (mmole) | 1.47E−04 | Concentration converted to amount based upon reservoir volume |
| PLGA (ug) | 9.86 | |
| PLGA (uL) | 9.86E−03 | |
| Volume fraction | 0.039% | |

Table Z5 shows that the extra H+ to be protonated corresponds to about 0.0059 M based on Table Z3 above. The amount of PLGA per year corresponds to about 9.86 ug having a volume of about 9.86 uL. For the 25 uL device, this corresponds to about 0.039% of the device.

Tables Z1 to Z5 show amounts of erodible material in accordance with many variations. One or more of the following may be adjusted in accordance with the variations described herein: target pH within device 100, volume of device 100, release rate of porous structure 150, half-life of therapeutic agent in device 100, rate of erosion of the erodible material comprising PLGA.

Figure 3E:
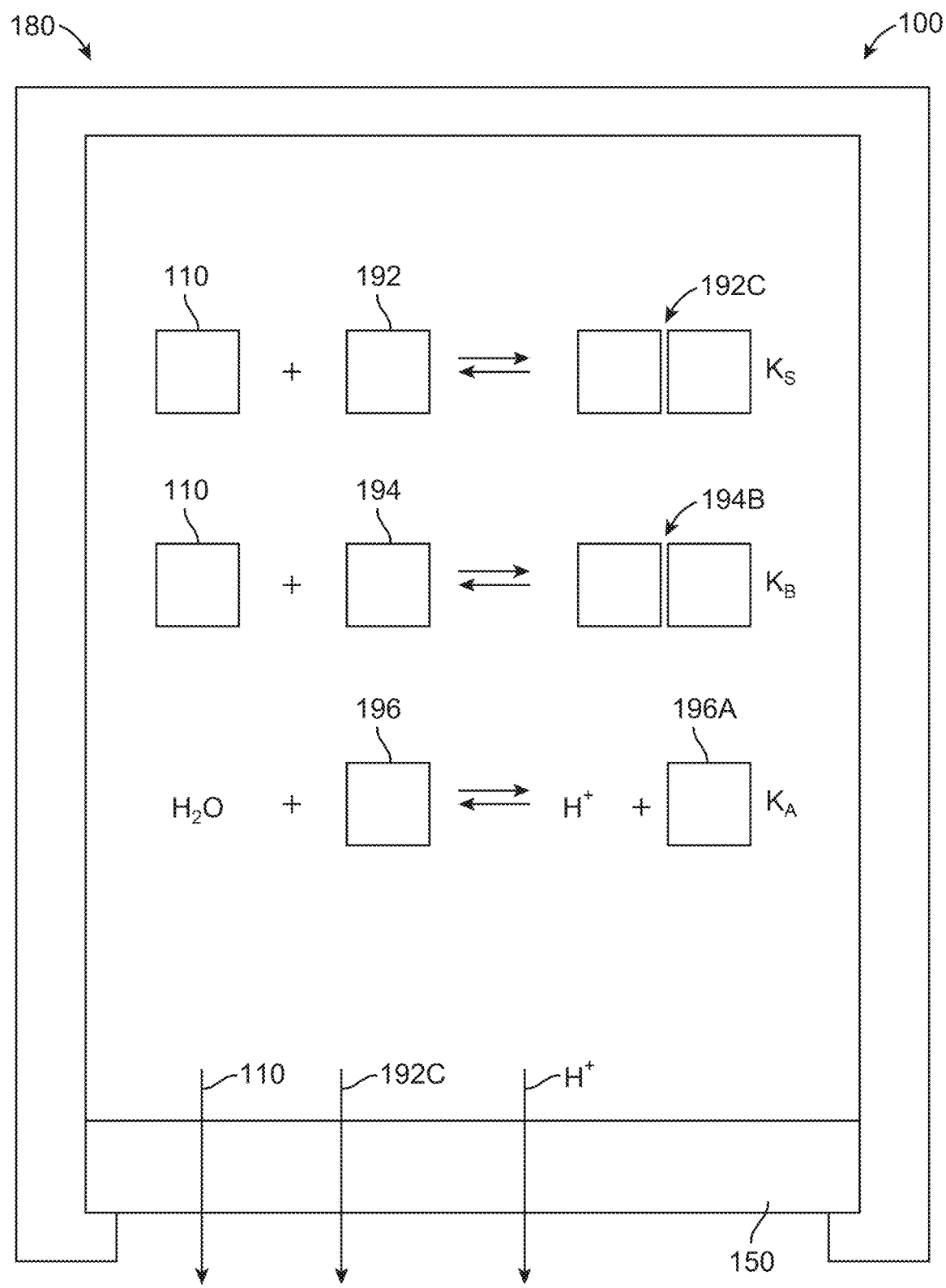
FIG. 3E shows reactions and equilibrium corresponding to components to determine release rates of the formulation as in FIG. 3A when injected into a therapeutic device, in accordance with variations described herein.

FIG. 3E shows reactions and equilibrium corresponding to components to determine release rates of the formulation as in FIG. 3A when injected into a therapeutic device. The stabilizer 192 and therapeutic agent 110 can be in equilibrium with complex 192C having a corresponding equilibrium constant Ks. The binding agent 194 and therapeutic agent 110 can be in pH dependent equilibrium with reversible binding 194B of therapeutic agent and binding agent corresponding to pH dependent equilibrium constant Kb. The erodible polymer can generate protons of an acid 196A with hydrolysis corresponding to equilibrium constant. The corresponding concentrations of therapeutic agent 110, complex 192C of stabilizer 192 and therapeutic agent 110 and protons H+ can be used to determine the diffusive flux of each of these components through porous structure 150 so as to determine the profile of the rate of release of therapeutic agent 110.

The release of therapeutic agent 110 may be modulated by one or more of the pH or the concentration of stabilizer 192 within the reservoir chamber. The increase in pH from about 6.5 to about 7 can shift the equilibrium of the binding agent and therapeutic agent toward dissociated therapeutic agent so as to increase the rate of release of the therapeutic agent. The decreased amount of stabilizer can shift the equilibrium of stabilizer and therapeutic agent away from complexed therapeutic agent and toward dissociated therapeutic agent in solution, so as to increase the rate of release of the therapeutic agent.

FIG. 4A shows released antibodies comprising antibody fragments 410 and a substrate 420 comprising binding agent 194, and FIG. 4B shows antibody fragments 410 reversibly bound to a substrate 420 with binding agent 194, in accordance with variations described herein. The anti-body fragments can be reversibly bound to the substrate comprising the binding agent, such that the bound antibody fragments are in equilibrium with the unbound antibody fragments. Many substrates comprising binding agent can reversibly bind at least a portion of an antibody. Examples of binding media may include particulates used in chromatography, such as: Macro-Prep t-Butyl HIC Support, Macro-Prep DEAE Support, CHT Ceramic, Hydroxyapatite Type I, Macro-Prep CM Support, Macro-Prep Methyl HIC Support, Macro-Prep Ceramic Hydroxyapatite Type II, UNOsphere S Cation Exchange Support, UNOsphere Q Strong Anion Exchange Support, Macro-Prep High-S Support, and Macro-Prep High-Q Support. Additional media to test for binding include ion exchange and bioaffinity chromatography media based on a hydrophilic polymeric support (GE Healthcare) that bind proteins with high capacity, and a hydrophilic packing material from Harvard Apparatus made from poly(vinyl alcohol) that binds more protein than silica. It should be appreciated that other candidates are considered herein.

The resin of the plurality of binding particles may comprise one or more of polystyrene or divinyl benzene. The particles may comprise spherical particles and may comprise a plurality of channels. When the reservoir chamber of the therapeutic device corresponds to a net negative charge of the therapeutic agent, the derivatized surface may comprise an anion exchange surface such as one or more of diethylaminoehtly (DEAE), Quaternary aminoethyl (QAE), or quaternatry ammonidum (Q), for example. When the reservoir chamber of the therapeutic device corresponds to a net positive charge of the therapeutic agent, the derivitized surface may comprise a cation exchange surface such as one or more of carboxy methyl (CM), Sulphoproply (SP), or methyl sulphonate (SP), for example.

Figure 4C:
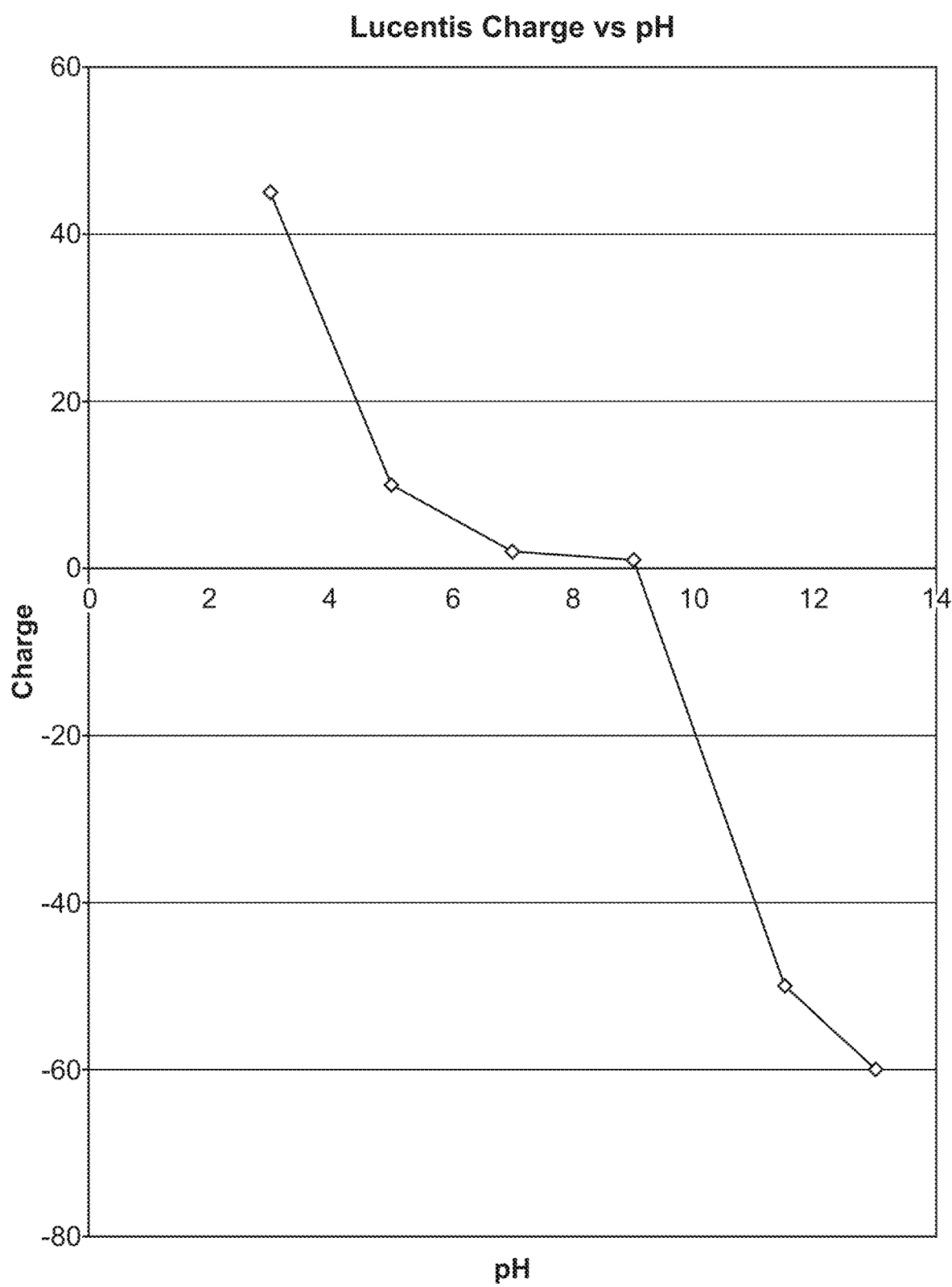
FIG. 4C shows net charge of ranibizumab from pH 3 to about pH 13, in accordance with variations described herein.

FIG. 4C shows net charge of ranibizumab from pH 3 to about pH 13. Similar plots can be determined for many proteins based therapeutic agents such as Fab antibody fragments and derivatives thereof, such as ranibizumab and derivatives thereof. The charge of the therapeutic agent can be used to determine reversible binding of the therapeutic agent to the binding agent. In many variations, the therapeutic agent comprising a protein such as ranibizumab may comprise an improved stability when the pH in the reservoir chamber of device is at least about 2 pH units from the isoelectric point.

TABLE YYY

| Charge of ranibizumab as a function of pH. | | | | | |
|---|---|---|---|---|---|
| Charge | 45 | 10 | 2 | 1 | −50 | −60 |
| pH | 3 | 5 | 7 | 9 | 11.5 | 13 |

Table YYY shows the charge of the ranibizumab molecule as a function of pH. The isoelectric point is around pH 9. The charge at pH 5 can be about +10, and the charge at pH 7 can be about +2, such that the amount of ranibizumab reversibly bound to the binding agent may change substantially from about pH 5 to about pH 7. Based on interpolation, the charge at about pH 6 is about 6. The change in charge from pH 6 to pH 7 is about 4, which can provide substantial change in binding so as to modulate the release of the therapeutic with pH.

Near the isoelectric the total number of negative and positive charges can be substantial, for example about 36 positive and 35 negative charges, such that there can be many charges to couple to the binding agent reversibly. The reversible binding agent may comprise a plurality of functional groups having both positive and negative charges to bind reversibly with the therapeutic agent. The composition of the buffer may be modulated, for example with salt so as to shield at least some of the charge interactions, so as to modulate the ratio of the portion of therapeutic agent bound to the binding agent to the unbound portion of the therapeutic agent, for example.

FIG. 5A shows therapeutic device 100 coupled to injector 187 to insert therapeutic agent 110 into container 130 of the device. The injector 187 may comprise needle 189 coupled to a syringe 188.

FIG. 5A-1 shows a therapeutic device 100 coupled to an injector 187 to inject and remove material from the device. The injector may comprise needle 189 having a first lumen 189A and a second lumen 189B configured to insert into a container of the device. The injector may simultaneously inject 510 therapeutic agent into and withdraw 520 liquid from the device. The injector may comprise a first one way valve and a second one way valve coupled to the first lumen and the second lumen, respectively.

FIG. 5B shows a therapeutic device comprising a microloop channel 530. The microloop channel may extend to a first port 530A and a second port 530B, such that the therapeutic agent can be injected into the first port, for example with a binding agent, and flowable material, for example liquid comprising binding agent, can be drawn from the microloop channel 530.

Figures 1, 5C:
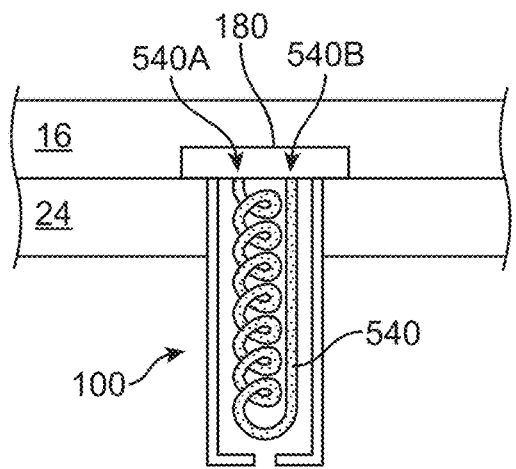
Figures 2, 5C:
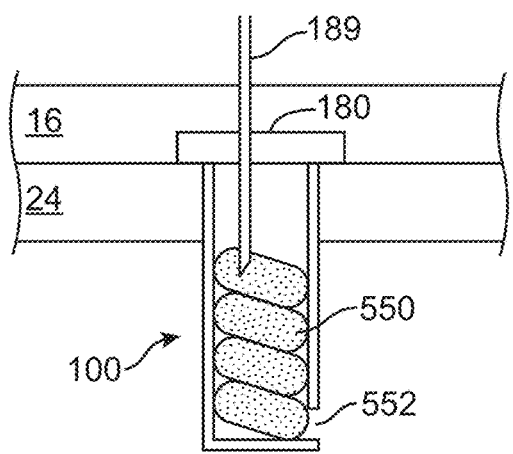

FIG. 5C-1 shows therapeutic device 100 comprising a tortuous channel 540. The tortuous channel may comprise extend from a first port 540A to a second port 540B, such that the therapeutic agent can be injected into the first port and flowable material, for example liquid comprising the binding agent, can be drawn from the second channel.

FIG. 5C-2 shows a therapeutic device comprising a tortuous coiled channel 550. The coiled channel 550 can extend to an exit port 552. A needle 189 can be inserted into the access port 180 to inject therapeutic agent into device 100.

Figure 5D:
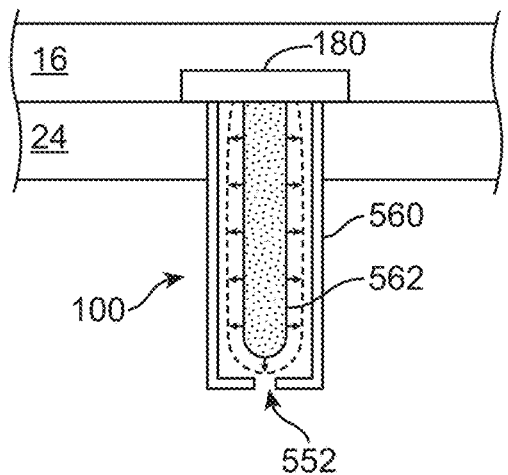
FIG. 5D shows an expandable and contractible structure to retain the therapeutic agent and an outer rigid casing to couple to the sclera, in accordance with variations described herein.

FIG. 5D shows an expandable and contactable structure 562 to retain the therapeutic agent and an outer rigid casing 560 to couple to the sclera. The expandable structure 562 may comprise a membrane, such as at least one of a bag, a balloon, a flexible reservoir, a diaphragm, or a bag. The outer rigid casing may extend substantially around the structure 562 and may comprise an opening to release liquid into the vitreous humor when the structure is expanded.

Figure 5E:
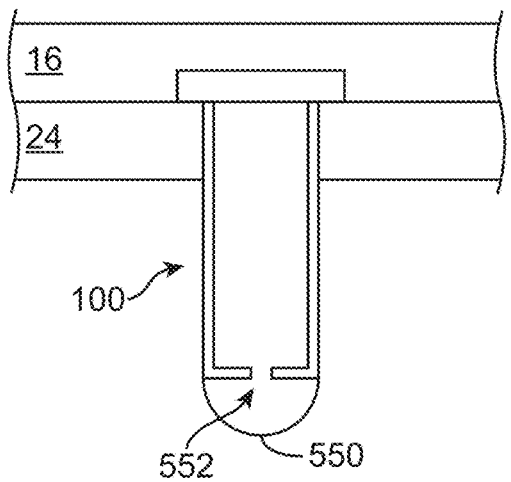
FIG. 5E shows a membrane disposed over an exit port of a therapeutic device, in accordance with variations described herein.

FIG. 5E shows a membrane 565 disposed over an exit port 552 of therapeutic device 100.

Figure 5F:
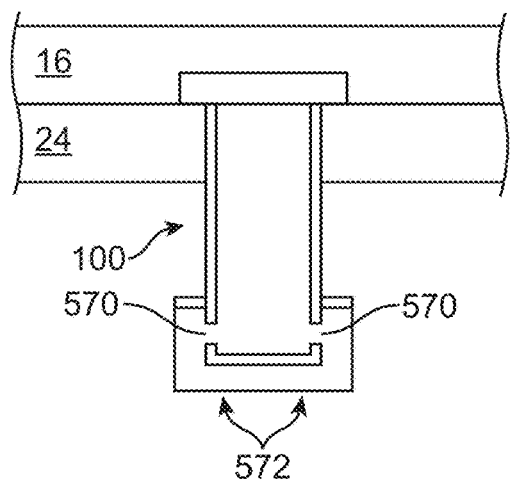
FIG. 5F shows a therapeutic device comprising a tubular membrane clamped onto the therapeutic device, in accordance with variations described herein.

FIG. 5F shows therapeutic device 100 comprising a tubular membrane 572 clamped onto the therapeutic device over side ports 570 of device 100.

When the protective membranes have pores of 0.2 um diameter, they are 20 or more times larger than the proteins of interest, which may comprise a model for delivery of the therapeutic agent. For example, molecular weights and diameters of models of proteins of therapeutic interest are:

| (a) | IgG | 150 kDa | 10.5 nm |
|---|---|---|---|
| (b) | BSA | 69 kDa | 7.2 nm |
| (c) | Fab fragment of IgG | 49 kDa | hydrodynamic diameter not reported |

Therefore, solutions of therapeutic compounds in the size range of IgG and BSA should flow relatively easily through 0.2 um pore size protective membranes used to stop passage of bacterial and other cells.

Binding Materials/Agents may comprise at least one of a chemical binding agent/material, a structural binding agent or material, or an electrostatic binding agent or material. The types of binding agent may comprise a classification composed of non-biodegradable material, for example glass beads, glass wool or a glass rod. A surface can be derivatized with at least one functional group so as to impart the binding agent or material with the potential for at least one of ionic, hydrophobic, or bioaffinity binding to at least one therapeutic compound.

The binding agent may comprise a biodegradable material. For example, the biodegradation, binding, or a combination of the previous processes may control the diffusion rate.

The binding agent may comprise ion exchange, and the ion exchange may comprise at least one of a functional group, a pH sensitive binding or a positive or negative charge. For example, ion exchange can be performed with at least one of diethylaminoethyl or carboxymethyl functional groups.

The binding agent may comprise a pH sensitive binding agent. For example, the binding agent can be configured to elute therapeutic agent at a pH of 7, and to bind the therapeutic agent at a pH from about 4 to about 6.5. A cation exchange binding agent can be configured, for example, such that at a pH of 7, the net negative charge of the binding agent decreases causing a decrease in binding of the positively charged drug and release of the therapeutic agent. A target buffer can be provided with the binding agent to reversibly couple the binding agent to the therapeutic agent. The rate of release can be controlled, for example slowed down, by using insolubility of the buffer in the vitreous. Alternatively or in combination, the elution can be limited by using a porous membrane or a physical property such as a size of an opening.

The ion exchange may comprise positive or negative ion exchange.

The binding agent may comprise hydrophobic interaction. For example, the binding agent may comprise at least one binding to hydrophobic pockets, for example at least one of methyl, ethyl, propyl, butyl, t-butyl or phenyl functional groups.

The binding agent may comprise affinity, for example at least one of a macromolecular affinity or a metal chelation affinity. Examples can include a hydroxyapatite, or chelated metal, for example zinc. Iminodiacetic acid can be chelated with zinc.

The binding agent may comprise at least one of the following functions: charging, recharging or elution. The charging may comprise a porous material injected therein so as to release the active ingredient. The porous matter may have an extremely large inert surface area, which surface area is available for binding. The recharging may comprise removing carrier+therapeutic agent; and adding freshly "charged" carrier+therapeutic agent.

The elution may comprise a byproduct, for example unbound binding agent that can be removed. For example, a mechanism such as diffusion or plug flow of vitreous may change a condition such as pH so as to reduce interaction of therapeutic agent and carriers.

Additionally or in the alternative, a sustained drug delivery system of the therapeutic agent may comprise drug delivery packets; e.g., microspheres that are activated. The packets can be activated with at least one of photochemical activation, thermal activation or biodegradation.

The therapeutic device may comprise at least one structure configured to provide safety precautions. The device may comprise at least one structure to prevent at least one of macrophage or other immune cell within the reservoir body; bacterial penetration; or retinal detachment.

The therapeutic device may be configured for other applications in the body. Other routes of administration of drugs may include at least one of intraocular, oral, subcutaneous, intramuscular, intraperitoneal, intranasal, dermal, intrathecal, intravascular, intra articular, pericardial, intraluminal in organs and gut or the like.

Conditions that may be treated and/or prevented using the drug delivery device and method described herein may include at least one of the following: hemophilia and other blood disorders, growth disorders, diabetes, leukemia, hepatitis, renal failure, HIV infection, hereditary diseases such as cerebrosidase deficiency and adenosine deaminase deficiency, hypertension, septic shock, autoimmune diseases such as multiple sclerosis, Graves disease, systemic lupus erythematosus and rheumatoid arthritis, shock and wasting disorders, cystic fibrosis, lactose intolerance, Crohn's disease, inflammatory bowel disease, gastrointestinal or other cancers, degenerative diseases, trauma, multiple systemic conditions such as anemia, and ocular diseases such as, for example, retinal detachment, proliferative retinopathy, proliferative diabetic retinopathy, degenerative disease, vascular diseases, occlusions, infection caused by penetrating traumatic injury, endophthalmitis such as endogenous/systemic infection, post-operative infections, inflammations such as posterior uveitis, retinitis or choroiditis and tumors, such as neoplasms and retinoblastoma.

Examples of therapeutic agents 110 that may be delivered by the therapeutic device 100 are described in Table 1A and may include Triamcinolone acetonide, Bimatoprost (Lumigan), Ranibizumab (Lucentis™), Travoprost (Travatan, Alcon), Timolol (Timoptic, Merck), Levobunalol (Betagan, Allergan), Brimonidine (Alphagan, Allergan), Dorzolamide (Trusopt, Merck), Brinzolamide (Azopt, Alcon). Additional examples of therapeutic agents that may be delivered by the therapeutic device include antibiotics such as tetracycline, chlortetracycline, bacitracin, neomycin, polymyxin, gramicidin, cephalexin, oxytetracycline, chloramphenicol kanamycin, rifampicin, ciprofloxacin, tobramycin, gentamycin, erythromycin and penicillin; antifungals such as amphotericin B and miconazole; anti-bacterials such as sulfonamides, sulfadiazine, sulfacetamide, sulfamethizole and sulfisoxazole, nitrofurazone and sodium propionate; antivirals such as idoxuridine, trifluorotymidine, acyclovir, ganciclovir and interferon; antiallergenics such as sodium cromoglycate, antazoline, methapyriline, chlorpheniramine, pyrilamine, cetirizine and prophenpyridamine; anti-inflammatories such as hydrocortisone, hydrocortisone acetate, dexamethasone, dexamethasone 21-phosphate, fluocinolone, medrysone, prednisolone, prednisolone 21-phosphate, prednisolone acetate, fluorometholone, betamethasone, and triamcinolone; non-steroidal anti-inflammatories such as salicylate, indomethacin, ibuprofen, diclofenac, flurbiprofen and piroxicam; decongestants such as phenylephrine, naphazoline and tetrahydrozoline; miotics and anticholinesterases such as pilocarpine, salicylate, acetylcholine chloride, physostigmine, eserine, carbachol, diisopropyl fluorophosphate, phospholine iodide and demecarium bromide; mydriatics such as atropine sulfate, cyclopentolate, homatropine, scopolamine, tropicamide, eucatropine and hydroxyamphetamine; sypathomimetics such as epinephrine; antineoplastics such as carmustine, cisplatin and fluorouracil; immunological drugs such as vaccines and immune stimulants; hormonal agents such as estrogens, estradiol, progestational, progesterone, insulin, calcitonin, parathyroid hormone and peptide and vasopressin hypothalamus releasing factor; beta adrenergic blockers such as timolol maleate, levobunolol Hcl and betaxolol Hcl; growth factors such as epidermal growth factor, fibroblast growth factor, platelet derived growth factor, transforming growth factor beta, somatotropin and fibronectin; carbonic anhydrase inhibitors such as dichlorophenamide, acetazolamide and methazolamide and other drugs such as prostaglandins, antiprostaglandins and prostaglandin precursors. Other therapeutic agents known to those skilled in the art which are capable of controlled, sustained release into the eye in the manner described herein are also suitable for use in accordance with variations described herein.

The therapeutic agent 110 may comprise one or more of the following: Abarelix, Abatacept, Abciximab, Adalimumab, Aldesleukin, Alefacept, Alemtuzumab, Alpha-1-proteinase inhibitor, Alteplase, Anakinra, Anistreplase, Antihemophilic Factor, Antithymocyte globulin, Aprotinin, Arcitumomab, Asparaginase, Basiliximab, Becaplermin, Bevacizumab, Bivalirudin, Botulinum Toxin Type A, Botulinum Toxin Type B, Capromab, Cetrorelix, Cetuximab, Choriogonadotropin alfa, Coagulation Factor IX, Coagulation factor VIIa, Collagenase, Corticotropin, Cosyntropin, Cyclosporine, Daclizumab, Darbepoetin alfa, Defibrotide, Denileukin diftitox, Desmopressin, Dornase Alfa,Drotrecogin alfa, Eculizumab, Efalizumab, Enfuvirtide, Epoetin alfa, Eptifibatide, Etanercept, Exenatide, Felypressin, Filgrastim, Follitropin beta, Galsulfase, Gemtuzumab ozogamicin, Glatiramer Acetate, Glucagon recombinant, Goserelin, Human Serum Albumin, Hyaluronidase, Ibritumomab, Idursulfase, Immune globulin, Infliximab, Insulin Glargine recombinant, Insulin Lyspro recombinant, Insulin recombinant, Insulin, porcine, Interferon Alfa-2a, Recombinant, Interferon Alfa-2b, Recombinant, Interferon alfacon-1, Interferonalfa-n1, Interferon alfa-n3, Interferon beta-1b, Interferon gamma-1b, Lepirudin, Leuprolide, Lutropin alfa, Mecasermin, Menotropins, Muromonab, Natalizumab, Nesiritide, Octreotide, Omalizumab, Oprelvekin, OspA lipoprotein, Oxytocin, Palifermin, Palivizumab, Panitumumab, Pegademase bovine, Pegaptanib, Pegaspargase, Pegfilgrastim, Peginterferon alfa-2a, Peginterferon alfa-2b, Pegvisomant, Pramlintide, Ranibizumab, Rasburicase, Reteplase, Rituximab, Salmon Calcitonin, Sargramostim, Secretin, Sermorelin, Serum albumin iodonated, Somatropin recombinant, Streptokinase, Tenecteplase, Teriparatide, Thyrotropin Alfa, Tositumomab, Trastuzumab, Urofollitropin, Urokinase, or Vasopressin. The molecular weights of the molecules and indications of these therapeutic agents are set for below in Table 1A, below.

The therapeutic agent 110 may comprise one or more of compounds that act by binding members of the immunophilin family of cellular proteins. Such compounds are known as "immunophilin binding compounds." Immunophilin binding compounds include but are not limited to the "limus" family of compounds. Examples of limus compounds that may be used include but are not limited to cyclophilins and FK506-binding proteins (FKBPs), including sirolimus (rapamycin) and its water soluble analog SDZ-RAD, tacrolimus, everolimus, pimecrolimus, CCI-779 (Wyeth), AP23841 (Ariad), and ABT-578 (Abbott Laboratories).

The limus family of compounds may be used in the compositions, devices and methods for the treatment, prevention, inhibition, delaying the onset of, or causing the regression of angiogenesis-mediated diseases and conditions of the eye, including choroidal neovascularization. The limus family of compounds may be used to prevent, treat, inhibit, delay the onset of, or cause regression of AMD, including wet AMD. Rapamycin may be used to prevent, treat, inhibit, delay the onset of, or cause regression of angiogenesis-mediated diseases and conditions of the eye, including choroidal neovascularization. Rapamycin may be used to prevent, treat, inhibit, delay the onset of, or cause regression of AMD, including wet AMD.

The therapeutic agent 110 may comprise one or more of: pyrrolidine, dithiocarbamate (NF.kappa.B inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™ (bortezomib, for injection; ranibuzumab (Lucentis™) and other antibodies directed to the same target; pegaptanib (Macugen™); vitronectin receptor antagonists, such as cyclic peptide antagonists of vitronectin receptor-type integrins; .alpha.-v/.beta.-3 integrin antagonists; .alpha.-v/.beta.-1 integrin antagonists; thiazolidinediones such as rosiglitazone or troglitazone; interferon, including .gamma.-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; apoptosis inhibiting agents; Visudyne™, snET2 and other photo sensitizers, which may be used with photodynamic therapy (PDT); inhibitors of hepatocyte growth factor (antibodies to the growth factor or its receptors, small molecular inhibitors of the c-met tyrosine kinase, truncated versions of HGF e.g. NK4).

The therapeutic agent 110 may comprise a combination with other therapeutic agents and therapies, including but not limited to agents and therapies useful for the treatment of angiogenesis or neovascularization, particularly CNV. Non-limiting examples of such additional agents and therapies include pyrrolidine, dithiocarbamate (NF.kappa.B inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™; bortezomib, for injection; ranibuzumab (Lucentis™) and other antibodies directed to the same target; pegaptanib (Macugen™); vitronectin receptor antagonists, such as cyclic peptide antagonists of vitronectin receptor-type integrins; alpha-v/beta-3 integrin antagonists; alpha-v/beta-1 integrin antagonists; thiazolidinediones such as rosiglitazone or troglitazone; interferon, including .gamma.-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; inhibitors of hepatocyte growth factor (antibodies to the growth factor or its receptors, small molecular inhibitors of the c-met tyrosine kinase, truncated versions of HGF e.g. NK4); apoptosis inhibiting agents; Visudyne™, snET2 and other photo sensitizers with photodynamic therapy (PDT); and laser photocoagulation.

The therapeutic agents may be used in conjunction with a pharmaceutically acceptable carrier such as, for example, solids such as starch, gelatin, sugars, natural gums such as acacia, sodium alginate and carboxymethyl cellulose; polymers such as silicone rubber; liquids such as sterile water, saline, dextrose, dextrose in water or saline; condensation products of castor oil and ethylene oxide, liquid glyceryl triester of a lower molecular weight fatty acid; lower alkanols; oils such as corn oil, peanut oil, sesame oil, castor oil, and the like, with emulsifiers such as mono- or diglyceride of a fatty acid, or a phosphatide such as lecithin, polysorbate 80, and the like; glycols and polyalkylene glycols; aqueous media in the presence of a suspending agent, for example, sodium carboxymethylcellulose, sodium hyaluronate, sodium alginate, poly(vinyl pyrrolidone) and similar compounds, either alone, or with suitable dispensing agents such as lecithin, polyoxyethylene stearate and the like. The carrier may also contain adjuvants such as preserving, stabilizing, wetting, emulsifying agents or other related materials.

The therapeutic device may comprise a container configured to hold at least one therapeutic agent, the container comprising a chamber to hold the at least one therapeutic agent with at least one opening to release the at least one therapeutic agent to the vitreous humor and porous structure 150 placed within the at least one opening. The porous structure 150 may comprise a fixed tortuous, porous material such as a sintered metal, a sintered glass or a sintered polymer with a defined porosity and tortuosity that controls the rate of delivery of the at least one therapeutic agent to the vitreous humor. The rigid porous structures provide certain advantages over capillary tubes, erodible polymers and membranes as a mechanism for controlling the release of a therapeutic agent or agents from the therapeutic device. These advantages include the ability of the rigid porous structure to comprise a needle stop, simpler and more cost effective manufacture, flushability for cleaning or declogging either prior to or after implantation, high efficiency depth filtration of microorganisms provided by the labyrinths of irregular paths within the structure and greater robustness due to greater hardness and thickness of the structure compared to a membrane or erodible polymer matrix. Additionally, when the rigid porous structure is manufactured from a sintered metal, ceramic, glass or certain plastics, it can be subjected to sterilization and cleaning procedures, such as heat or radiation based sterilization and depyrogenation that might damage polymer and other membranes. In certain variations, as illustrated in example 9, the rigid porous structure may be configured to provide a therapeutically effective, concentration of the therapeutic agent in the vitreous for at least 6 months. This release profile provided by certain configurations of the rigid porous structures enables a smaller device, which is preferred in a small organ such as the eye where larger devices may alter or impair vision.

Figures 1, 6A:
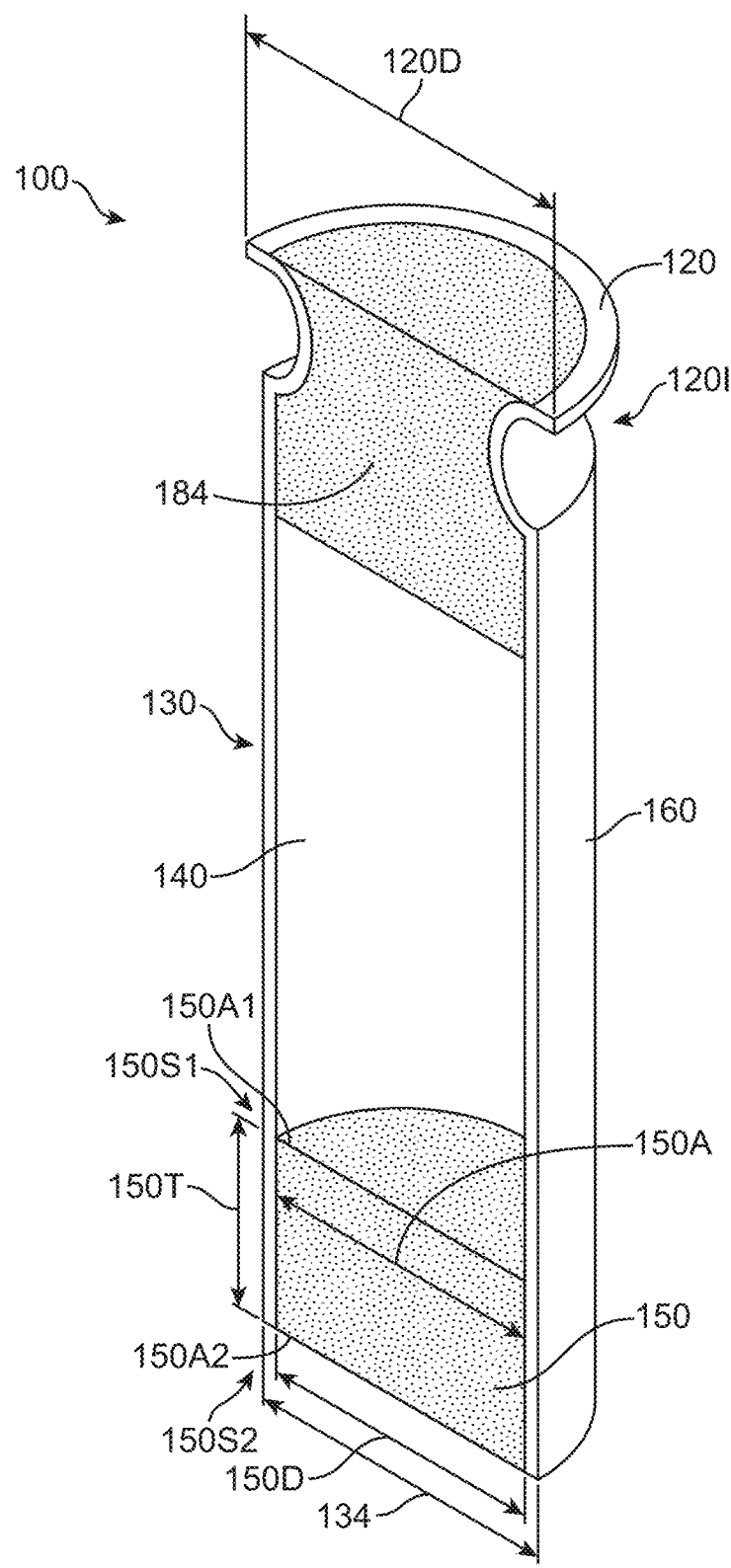
Figures 2, 6A:
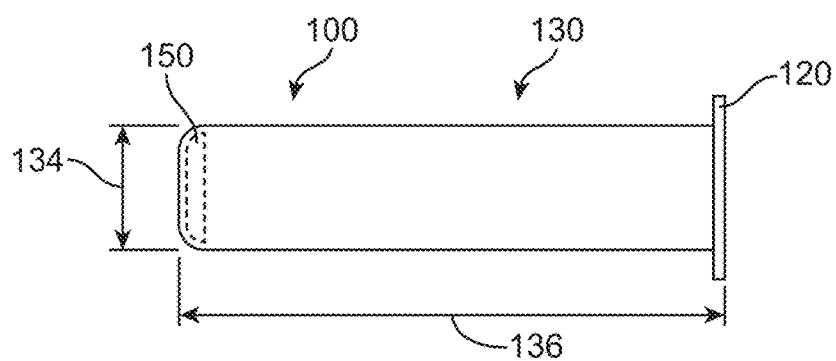

FIG. 6A-1 shows a therapeutic device 100 comprising a container 130 having a penetrable barrier 184 disposed on a first end, a porous structure 150 disposed on a second end to release therapeutic agent for an extended period, and a retention structure 120 comprising an extension protruding outward from the container to couple to the sclera and the conjunctiva. The extending protrusion of the retention structure may comprise a diameter 120D. The retention structure may comprise an indentation 120I sized to receive the sclera. The container may comprise a tubular barrier 160 that defines at least a portion of the reservoir, and the container may comprise a width, for example a diameter 134. The diameter 134 can be sized within a range, for example within a range from about 0.5 to about 4 mm, for example within a range from about 1 to 3 mm and can be about 2 mm, for example. The container may comprise a length 136, sized so as to extend from the conjunctiva to the vitreous to release the therapeutic agent into the vitreous. The length 136 can be sized within a range, for example within a range from about 2 to about 14 mm, for example within a range from about 4 to 10 mm and can be about 7 mm, for example. The volume of the reservoir may be substantially determined by an inner cross-sectional area of the tubular structure and distance from the porous structure to the penetrable barrier. The retention structure may comprise an annular extension having a retention structure diameter greater than a diameter of the container. The retention structure may comprise an indentation configured to receive the sclera when the extension extends between the sclera and the conjunctive. The penetrable barrier may comprise a septum disposed on a proximal end of the container, in which the septum comprises a barrier that can be penetrated with a sharp object such as a needle for injection of the therapeutic agent. The porous structure may comprise a cross sectional area 150A sized to release the therapeutic agent for the extended period.

The porous structure 150 may comprise a first side coupled to the reservoir 150S1 and a second side to couple to the vitreous 150S2. The first side may comprise a first area 150A1 and the second side may comprise a second area 150A2. The porous structure may comprise a thickness 105T. The porous structure many comprise a diameter 150D.

The volume of the reservoir 140 may comprise from about 5 uL to about 2000 uL of therapeutic agent, or for example from about 10 uL to about 200 uL of therapeutic agent.

The therapeutic agent stored in the reservoir of the container comprises at least one of a solid comprising the therapeutic agent, a solution comprising the therapeutic agent, a suspension comprising the therapeutic agent, particles comprising the therapeutic agent adsorbed thereon, or particles reversibly bound to the therapeutic agent. For example, reservoir may comprise a suspension of a corticosteroid such as triamcinolone acetonide to treat inflammation of the retina. The reservoir may comprise a buffer and a suspension of a therapeutic agent comprising solubility within a range from about 1 ug/mL to about 100 ug/mL, such as from about 1 ug/mL to about 40 ug/mL. For example, the therapeutic agent may comprise a suspension of triamcinolone acetonide having a solubility of approximately 19 ug/mL in the buffer at 37 C when implanted.

The release rate index may comprise many values, and the release rate index with the suspension may be somewhat higher than for a solution in many variations, for example. The release rate index may be no more than about 5, and can be no more than about 2.0, for example no more than about 1.5, and in many variations may be no more than about 1.2, so as to release the therapeutic agent with therapeutic amounts for the extended time.

The therapeutic device, including for example, the retention structure and the porous structure, may be sized to pass through a lumen of a catheter.

The porous structure may comprise a needle stop that limits penetration of the needle. The porous structure may comprise a plurality of channels configured for the extended release of the therapeutic agent. The porous structure may comprise a rigid sintered material having characteristics suitable for the sustained release of the material.

FIG. 6A-2 shows a therapeutic device as in FIG. 6A-1 comprising a rounded distal end.

Figure 6B:
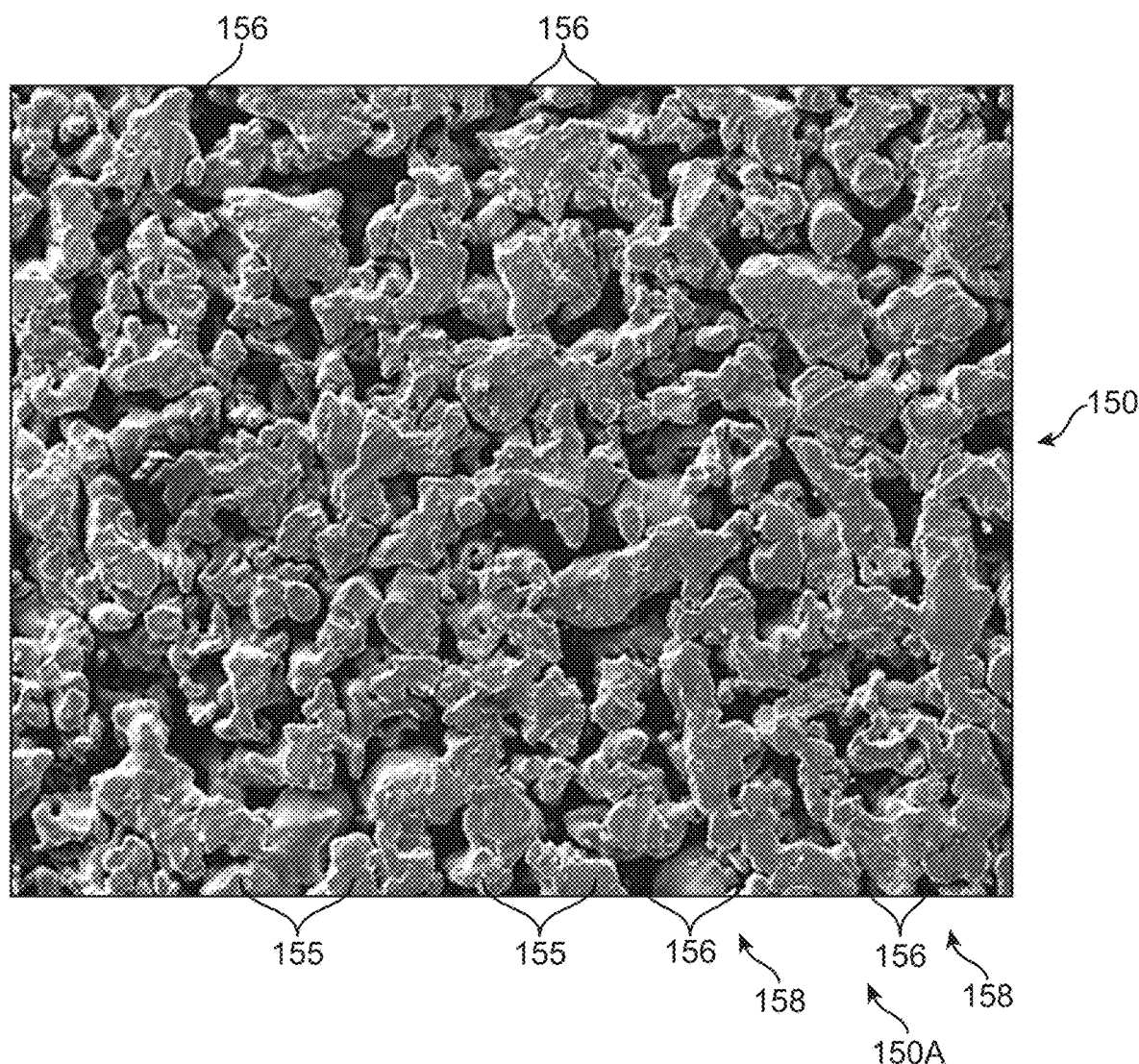
FIG. 6B shows a rigid porous structure configured for sustained release with a device as in FIG. 6A-1, in accordance with variations described herein.

FIG. 6B shows a rigid porous structure as in FIG. 6A-1. The rigid porous structure 158 comprises a plurality of interconnecting channels 156. The porous structure comprises a sintered material composed of interconnected grains 155 of material. The interconnected grains of material define channels that extend through the porous material to release the therapeutic agent. The channels may extend around the sintered grains of material, such that the channels comprise interconnecting channels extending through the porous material.

The rigid porous structure can be configured for injection of the therapeutic agent into the container in many ways. The channels of the rigid porous structure may comprise substantially fixed channels when the therapeutic agent is injected into the reservoir with pressure. The rigid porous structure comprises a hardness parameter within a range from about 160 Vickers to about 500 Vickers. In some variations the rigid porous structure is formed from sintered stainless steel and comprises a hardness parameter within a range from about 200 Vickers to about 240 Vickers. In some variations it is preferred to inhibit ejection of the therapeutic agent through the porous structure during filling or refilling the reservoir of the therapeutic device with a fluid. In these variations the channels of the rigid porous structure comprise a resistance to flow of an injected solution or suspension through a thirty gauge needle such that ejection of said solution or suspension through the rigid porous structure is substantially inhibited when said solution or suspension is injected into the reservoir of the therapeutic device. Additionally, these variations may optionally comprise an evacuation vent or an evacuation reservoir under vacuum or both to facilitate filling or refilling of the reservoir.

The reservoir and the porous structure can be configured to release therapeutic amounts of the therapeutic agent in many ways. The reservoir and the porous structure can be configured to release therapeutic amounts of the therapeutic agent corresponding to a concentration of at least about 0.1 ug per ml of vitreous humor for an extended period of at least about three months. The reservoir and the porous structure can be configured to release therapeutic amounts of the therapeutic agent corresponding to a concentration of at least about 0.1 ug per ml of vitreous humor and no more than about 10 ug per ml for an extended period of at least about three months. The therapeutic agent may comprise at least a fragment of an antibody and a molecular weight of at least about 10 k Daltons. For example, the therapeutic agent may comprise one or more of ranibizumab or bevacizumab. Alternatively or in combination, the therapeutic agent may comprise a small molecule drug suitable for sustained release. The reservoir and the porous structure may be configured to release therapeutic amounts of the therapeutic agent corresponding to a concentration of at least about 0.1 ug per ml of vitreous humor and no more than about 10 ug per ml for an extended period of at least about three months or at least about six months. The reservoir and the porous structure can be configured to release therapeutic amounts of the therapeutic agent corresponding to a concentration of at least about 0.1 ug per ml of vitreous humor and no more than about 10 ug per ml for an extended period of at least about twelve months or at least about two years or at least about three years. The reservoir and the porous structure may also be configured to release therapeutic amounts of the therapeutic agent corresponding to a concentration of at least about 0.01 ug per ml of vitreous humor and no more than about 300 ug per ml for an extended period of at least about 3 months or 6 months or 12 months or 24 months.

The channels of the rigid porous structure comprise a hydrogel configured to limit a size of molecules passed through the channels of the rigid porous structure. For example, the hydrogel can be formed within the channels and may comprise an acrylamide gel. The hydrogel comprises a water content of at least about 70%. For example, the hydrogel may comprise a water content of no more than about 90% to limit molecular weight of the therapeutic agent to about 30 k Daltons. The hydrogel comprises a water content of no more than about 95% to limit molecular weight of the therapeutic agent to about 100 k Daltons. The hydrogel may comprise a water content within a range from about 90% to about 95% such that the channels of the porous material are configured to pass Lucentis™ and substantially not pass Avastin™.

The rigid porous structure may comprise a composite porous material that can readily be formed in or into a wide range of different shapes and configurations. For example, the porous material can be a composite of a metal, aerogel or ceramic foam (i.e., a reticulated intercellular structure in which the interior cells are interconnected to provide a multiplicity of pores passing through the volume of the structure, the walls of the cells themselves being substantially continuous and non-porous, and the volume of the cells relative to that of the material forming the cell walls being such that the overall density of the intercellular structure is less than about 30 percent theoretical density) through pores of which are impregnated with a sintered powder or aerogel. The thickness, density, porosity and porous characteristics of the final composite porous material can be varied to conform with the desired release of the therapeutic agent.

Variations comprise a method of making an integral (i.e., single-component) porous structure. The method may comprise introducing particles into a mold having a desired shape for the porous structure. The shape includes a proximal end defining a plurality of proximal porous channel openings to couple to the reservoir, a distal end defining a plurality of outlet channel openings to couple to the vitreous humor of the eye, a plurality of blind inlet cavities extending into the filter from the proximal openings, and a plurality of blind outlet cavities extending into the porous structure from the outlet channel openings. The method further includes applying pressure to the mold, thereby causing the particles to cohere and form a single component, and sintering the component to form the porous structure. The particles can be pressed and cohere to form the component without the use of a polymeric binder, and the porous structure can be formed substantially without machining.

The mold can be oriented vertically with the open other end disposed upwardly, and metal powder having a particle size of less than 20 micrometers can be introduced into the cavity through the open end of the mold while vibrating the mold to achieve substantially uniform packing of the metal powder in the cavity. A cap can be placed on the open other end of the mold, and pressure is applied to the mold and thereby to the metal powder in the cavity to cause the metal powder to cohere and form a cup-shaped powdered metal structure having a shape corresponding to the mold. The shaped powdered metal structure can be removed from the mold, and sintered to obtain a porous sintered metal porous structure.

The metal porous structure can be incorporated into the device by a press fit into an impermeable structure with an opening configured to provide a tight fit with the porous structure. Other means, such as welding, can be used to incorporate the porous structure into the device. Alternatively, or in combination, the powdered metal structure can be formed in a mold where a portion of the mold remains with the shaped powdered metal structure and becomes part of the device. This may be advantageous in achieving a good seal between the porous structure and the device.

The release rate of therapeutic agent through a porous body, such as a sintered porous metal structure or a porous glass structure, may be described by diffusion of the therapeutic agent within the porous structure with the channel parameter, and with an effective diffusion coefficient equal to the diffusion coefficient of the therapeutic agent in the liquid that fills the reservoir multiplied by the Porosity and a Channel Parameter of the porous body:

$$\text{Release Rate}=(D\,P/F)A(c_R-c_V)/L,$$

where:

$c_R$=Concentration in reservoir $c_V$=Concentration outside of the reservoir or in the vitreous D=Diffusion coefficient of the therapeutic agent in the reservoir solution P=Porosity of porous structure F=Channel parameter that may correspond to a tortuosity parameter of channels of porous structure A=Area of porous structure L=Thickness (length) of porous structure $$\text{Cumulative Release}=1-cR/cR0=1-\exp((-D\,PA/FL\,V_R)t),$$

where t=time, Vr=reservoir volume

The release rate index can (hereinafter "RRI") be used to determine release of the therapeutic agent. The RRI may be defined as (PA/FL), and the RRI values herein will have units of mm unless otherwise indicated. Many of the porous structures used in the therapeutic delivery devices described herein have an RRI of no more than about 5.0, often no more than about 2.0, and can be no more than about 1.2 mm.

The channel parameter can correspond to an elongation of the path of the therapeutic agent released through the porous structure. The porous structure may comprise many interconnecting channels, and the channel parameter can correspond to an effective length that the therapeutic agent travels along the interconnecting channels of the porous structure from the reservoir side to the vitreous side when released. The channel parameter multiplied by the thickness (length) of the porous structure can determine the effective length that the therapeutic agent travels along the interconnecting channels from the reservoir side to the vitreous side. For example, the channel parameter (F) of about 1.5 corresponds to interconnecting channels that provide an effective increase in length traveled by the therapeutic agent of about 50%, and for a 1 mm thick porous structure the effective length that the therapeutic agent travels along the interconnecting channels from the reservoir side to the vitreous side corresponds to about 1.5 mm. The channel parameter (F) of at least about 2 corresponds to interconnecting channels that provide an effective increase in length traveled by the therapeutic agent of about 100%, and for a 1 mm thick porous structure the effective length that the therapeutic agent travels along the interconnecting channels from the reservoir side to the vitreous side corresponds to at least about 2.0 mm. As the porous structure comprises many interconnecting channels that provide many alternative paths for release of the therapeutic agent, blockage of some of the channels provides no substantial change in the effective path length through the porous structure as the alternative interconnecting channels are available, such that the rate of diffusion through the porous structure and the release of the therapeutic agent are substantially maintained when some of the channels are blocked.

If the reservoir solution is aqueous or has a viscosity similar to water, the value for the diffusion coefficient of the therapeutic agent (TA) in water at the temperature of interest may be used. The following equation can be used to estimate the diffusion coefficient at 37° C. from the measured value of $D_{BSA,20C}$=6.1 e-7 cm2/s for bovine serum albumin in water at 20° C. (Molokhia et al, *Exp Eye Res* 2008):

$$D_{TA,37C}=D_{BSA,20C}(\eta_{20C}/\eta_{37C})(MW_{BSA}MW_{TA})^{1/3}$$

where

MW refers to the molecular weight of either BSA or the test compound and η is the viscosity of water. The following lists diffusion coefficients of proteins of interest.

| Compound | MW | Temp C. | Diff Coeff (cm^2/s) |
| --- | --- | --- | --- |
| BSA | 69,000 | 20 | 6.1E−07 |
| BSA | 69,000 | 37 | 9.1E−07 |
| Ranibizumab | 48,000 | 20 | 6.9E−07 |
| Ranibizumab | 48,000 | 37 | 1.0E−06 |
| Bevacizumab | 149,000 | 20 | 4.7E−07 |
| Bevacizumab | 149,000 | 37 | 7.1E−07 |

Small molecules have a diffusion coefficient similar to fluorescein (MW=330, D=4.8 to 6 e-6 cm²/s from Stay, M S et al. *Pharm Res* 2003, 20(1), pp. 96-102). For example, the small molecule may comprise a glucocorticoid such as triamcinolone acetonide having a molecular weight of about 435.

The porous structure comprises a porosity, a thickness, a channel parameter and a surface area configured to release therapeutic amounts for the extended period. The porous material may comprise a porosity corresponding to the fraction of void space of the channels extending within the material. The porosity comprises a value within a range from about 3% to about 70%. In other variations, the porosity comprises a value with a range from about 5% to about 10% or from about 10% to about 25%, or for example from about 15% to about 20%. Porosity can be determined from the weight and macroscopic volume or can be measured via nitrogen gas adsorption The porous structure may comprise a plurality of porous structures, and the area used in the above equation may comprise the combined area of the plurality of porous structures.

The channel parameter may comprise a fit parameter corresponding to the tortuosity of the channels. For a known porosity, surface area and thickness of the surface parameter, the curve fit parameter F, which may correspond to tortuosity of the channels can be determined based on experimental measurements. The parameter PA/FL can be used to determine the desired sustained release profile, and the values of P, A, F and L determined. The rate of release of the therapeutic agent corresponds to a ratio of the porosity to the channel parameter, and the ratio of the porosity to the channel parameter can be less than about 0.5 such that the porous structure releases the therapeutic agent for the extended period. For example, the ratio of the porosity to the channel parameter is less than about 0.1 or, for example, less than about 0.2 such that the porous structure releases the therapeutic agent for the extended period. The channel parameter may comprise a value of at least about 1, such as at least about 1.2. For example, the value of the channel parameter may comprise at least about 1.5, for example at least about 2, and may comprise at least about 5. The channel parameter can be within a range from about 1.1 to about 10, for example within a range from about 1.2 to about 5. The channel parameter to release the therapeutic agent for an intended release rate profile can be determined empirically.

The area in the model originates from the description of mass transported in units of flux; i.e., rate of mass transfer per unit area. For simple geometries, such as a porous disc mounted in an impermeable sleeve of equal thickness, the area corresponds to one face of the disc and the thickness, L, is the thickness of the disc. For more complex geometries, such as a porous body in the shape of a truncated cone, the effective area is a value in between the area where therapeutic agent enters the porous body and the area where therapeutic agent exits the porous body.

A model can be derived to describe the release rate as a function of time by relating the change of concentration in the reservoir to the release rate described above. This model assumes a solution of therapeutic agent where the concentration in the reservoir is uniform. In addition, the concentration in the receiving fluid or vitreous is considered negligible ($c_V=0$). Solving the differential equation and rearrangement yields the following equations describing the concentration in the reservoir as a function of time, t, and volume of the reservoir, $V_R$, for release of a therapeutic agent from a solution in a reservoir through a porous structure.

$$c_R = c_{R0} \exp((-D\,PA/FL\,V_R)t)$$

and Cumulative Release=$1-c_R/c_{R0}$

When the reservoir contains a suspension, the concentration in reservoir, $c_R$, is the dissolved concentration in equilibrium with the solid (i.e., the solubility of the therapeutic agent). In this case, the concentration in the reservoir is constant with time, the release rate is zero order, and the cumulative release increases linearly with time until the time when the solid is exhausted.

Therapeutic concentrations for many ophthalmic therapeutic agents may be determined experimentally by measuring concentrations in the vitreous humor that elicit a therapeutic effect. Therefore, there is value in extending predictions of release rates to predictions of concentrations in the vitreous. A one-compartment model may be used to describe elimination of therapeutic agent from eye tissue.

Current intravitreal administration of therapeutic agents such as Lucentis™ involves a bolus injection. A bolus injection into the vitreous may be modeled as a single exponential with rate constant, k=0.693/half-life and a cmax=dose/$V_v$, where $V_v$ is the vitreous volume. As an example, the half-life for ranibizumab is approximately 3 days in the rabbit and the monkey (Gaudreault et al.) and 9 days in humans (Lucentis' package insert). The vitreous volume is approximately 1.5 mL for the rabbit and monkey and 4.5 mL for the human eye. The model predicts an initial concentration of 333 ug/mL for a bolus injection of 0.5 mg Lucentis™ into the eye of a monkey. This concentration decays to a vitreous concentration of 0.1 ug/mL after about a month.

For devices with extended release, the concentration in the vitreous changes slowly with time. In this situation, a model can be derived from a mass balance equating the release rate from the device (described by equations above) with the elimination rate from the eye, k $c_v$ $V_v$. Rearrangement yields the following equation for the concentration in the vitreous:

$c_v$=Release rate from device/k $V_v$.

Since the release rate from a device with a solution of therapeutic agent decreases exponentially with time, the concentration in the vitreous decreases exponentially with the same rate constant. In other words, vitreous concentration decreases with a rate constant equal to D PA/FL $V_R$ and, hence, is dependent on the properties of the porous structure and the volume of the reservoir.

Since the release rate is zero order from a device with a suspension of therapeutic agent, the vitreous concentration will also be time-independent. The release rate will depend on the properties of the porous structure via the ratio, PA/FL, but will be independent of the volume of the reservoir until the time at which the drug is exhausted.

The channels of the rigid porous structure can be sized in many ways to release the intended therapeutic agent. For example, the channels of the rigid porous structure can be sized to pass therapeutic agent comprising molecules having a molecular weight of at least about 100 Daltons or for example, at least about 50 k Daltons. The channels of the rigid porous structure can be sized to pass therapeutic agent comprising molecules comprising a cross-sectional size of no more than about 10 nm. The channels of the rigid porous structure comprise interconnecting channels configured to pass the therapeutic agent among the interconnecting channels. The rigid porous structure comprises grains of rigid material and wherein the interconnecting channels extend at least partially around the grains of rigid material to pass the therapeutic agent through the porous material. The grains of rigid material can be coupled together at loci of attachment and wherein the interconnecting channels extend at least partially around the loci of attachment.

The porous structure and reservoir may be configured to release the glucocorticoid for an extended time of at least about six months with a therapeutic amount of glucocorticoid of corresponding to an in situ concentration within a range from about 0.05 ug/mL to about 4 ug/mL, for example from 0.1 ug/mL to about 4 ug/mL, so as to suppress inflammation in the retina-choroid.

The porous structure comprises a sintered material. The sintered material may comprise grains of material in which the grains comprise an average size of no more than about 20 um. For example, the sintered material may comprise grains of material in which the grains comprise an average size of no more than about 10 um, an average size of no more than about 5 um, or an average size of no more than about 1 um. The channels are sized to pass therapeutic quantities of the therapeutic agent through the sintered material for the extended time based on the grain size of the sintered material and processing parameters such as compaction force and time and temperature in the furnace. The channels can be sized to inhibit penetration of microbes including bacteria and fungal spores through the sintered material.

The sintered material comprises a wettable material to inhibit bubbles within the channels of the material.

The sintered material comprises at least one of a metal, a ceramic, a glass or a plastic. The sintered material may comprise a sintered composite material, and the composite material comprises two or more of the metal, the ceramic, the glass or the plastic. The metal comprises at least one of Ni, Ti, nitinol, stainless steel including alloys such as 304, 304L, 316 or 316L, cobalt chrome, elgiloy, hastealloy, c-276 alloy or Nickel 200 alloy. The sintered material may comprise a ceramic. The sintered material may comprise a glass. The plastic may comprise a wettable coating to inhibit bubble formation in the channels, and the plastic may comprise at least one of polyether ether ketone (PEEK), polyethylene, polypropylene, polyimide, polystyrene, polycarbonate, polyacrylate, polymethacrylate, or polyamide.

The rigid porous structure may comprise a plurality of rigid porous structures coupled to the reservoir and configured to release the therapeutic agent for the extended period. For example, additional rigid porous structure can be disposed along the container, for example the end of the container may comprise the porous structure, and an additional porous structure can be disposed along a distal portion of the container, for example along a tubular sidewall of the container.

The therapeutic device can be tuned to release therapeutic amounts of the therapeutic agent above the minimum inhibitory concentration for an extended time based on bolus injections of the therapeutic agent. For example, the volume of the chamber of the reservoir can be sized with the release rate of the porous structure based on the volume of the bolus injection. A formulation of a therapeutic agent can be provided, for example a known intravitreal injection formulation. The therapeutic agent can be capable of treating the eye with bolus injections, such that the formulation has a corresponding period between each of the bolus injections to treat the eye. For example the bolus injections may comprise monthly injections. Each of the bolus injections comprises a volume of the formulation, for example 50 uL. Each of the bolus injections of the therapeutic agent may correspond to a range of therapeutic concentrations of the therapeutic agent within the vitreous humor over the time course between injections, and the device can be tuned so as to release therapeutic amounts of the therapeutic agent such that the vitreous concentrations of the released therapeutic agent from the device are within the range of therapeutic concentrations of the corresponding bolus injections. For example, the therapeutic agent may comprise a minimum inhibitory concentration to treat the eye, for example at least about 3 ug/mL, and the values of the range of therapeutic concentrations can be at least about 3 ug/mL. The therapeutic device can be configured to treat the eye with an injection of the monthly volume of the formulation into the device, for example through the penetrable barrier. The reservoir of the container has a chamber to contain a volume of the therapeutic agent, for example 35 uL, and a mechanism to release the therapeutic agent from the chamber to the vitreous humor.

The volume of the container and the release mechanism can be tuned to treat the eye with the therapeutic agent with vitreous concentrations within the therapeutic range for an extended time with each injection of the quantity corresponding to the bolus injection, such that the concentration of the therapeutic agent within the vitreous humor remains within the range of therapeutic concentrations and comprises at least the minimum inhibitory concentration. The extended time may comprise at least about twice the corresponding period of the bolus injections. The release mechanism comprises one or more of a porous frit, a sintered porous frit, a permeable membrane, a semi-permeable membrane, a capillary tube or a tortuous channel, nano-structures, nano-channels or sintered nano-particles. For example, the porous frit may comprise a porosity, cross-sectional area, and a thickness to release the therapeutic agent for the extended time. The volume of the container reservoir can be sized in many ways in relation to the volume of the injected formulation and can be larger than the volume of injected formulation, smaller than the volume of injected formulation, or substantially the same as the volume of injected formulation. For example, the volume of the container may comprise no more than the volume of the formulation, such that at least a portion of the formulation injected into the reservoir passes through the reservoir and comprises a bolus injection to treat the patient immediately. As the volume of the reservoir is increased, the amount of formulation released to the eye through the porous structure upon injection can decrease along with the concentration of active ingredient of the therapeutic agent within the reservoir, and the release rate index can be increased appropriately so as to provide therapeutic amounts of therapeutic agent for the extended time. For example, the volume of the reservoir of the container can be greater than the volume corresponding to the bolus injection, so as to provide therapeutic amounts for at least about five months, for example six months, with an injection volume corresponding to a monthly injection of Lucentis™. For example, the formulation may comprise Lucentis™ modified in accordance with variations, 50 uL, and the reservoir may comprise a volume of about 100 uL and provide therapeutic vitreous concentrations of at least about 3 ug/mL for six months with 50 uL of Lucentis™ injected into the reservoir.

The chamber may comprise a substantially fixed volume and the release rate mechanism comprises a substantially rigid structure to maintain release of the therapeutic agent above the minimum inhibitory concentration for the extended time with each injection of a plurality of injections.

A first portion of the injection may pass through the release mechanism and treat the patient when the formulation is injected, and a second portion of the formulation can be contained in the chamber when the formulation is injected.

FIG. 6B-1 shows interconnecting channels 156 extending from first side 150S1 to second side 150S2 of the porous structure as in FIG. 6B. The interconnecting channels 156 extend to a first opening 158A1, a second opening 158A2 and an Nth opening 158AN on the first side 150S1. The interconnecting channels 156 extend to a first opening 158B1, a second opening 158B2 and an Nth opening 158BN on the second side 150S2. Each of the openings of the plurality of channels on the first side is connected to each of the openings of plurality of channels on the second side, such that effective length traveled along the channels is greater than thickness 150T. The channel parameter can be within a range from about 1.1 to about 10, such that the effective length is within a range from about 1.1 to 10 times the thickness 150T. For example, the channel parameter can be about 1 and the porosity about 0.2, such that the effective length corresponds to at least about 5 times the thickness 150T.

The rigid porous structure can be shaped and molded in many ways for example with tubular shapes, conical shapes, discs and hemispherical shapes. The rigid porous structure may comprise a molded rigid porous structure. The molded rigid porous structure may comprise at least one of a disk, a helix or a tube coupled to the reservoir and configured to release the therapeutic agent for the extended period.

The formulation can be injected into many therapeutic devices, for example as described in U.S. Pat. Nos. 5,466,233; 5,972,369; 6,719,750; and U.S. Patent Publication No. 2003/0014036 A1.

The porous structure 150 may comprise a plurality of elongate nano-channels extending from a first side of the porous structure to a second side of the porous structure. The porous structure 150 may comprise a rigid material having the holes formed thereon, and the holes may comprise a maximum dimension across such as a diameter. The diameter of the nano-channels may comprise a dimension across, for example from about 10 nm across, to about 1000 nm across, or larger. The channels may be formed with etching of the material, for example lithographic etching of the material. The channels may comprise substantially straight channels such that the channel parameter F comprises about 1, and the parameters area A, and thickness or length L correspond to the combined cross-sectional area of the channels and the thickness or length of the porous structure.

The porous structure 150 may comprise interconnecting nano-channels, for example formed with a sintered nano-material.

The injection of therapeutic agent into the device 100 as described herein can be performed before implantation into the eye or alternatively when the therapeutic device is implanted into the eye.

Figure 7:
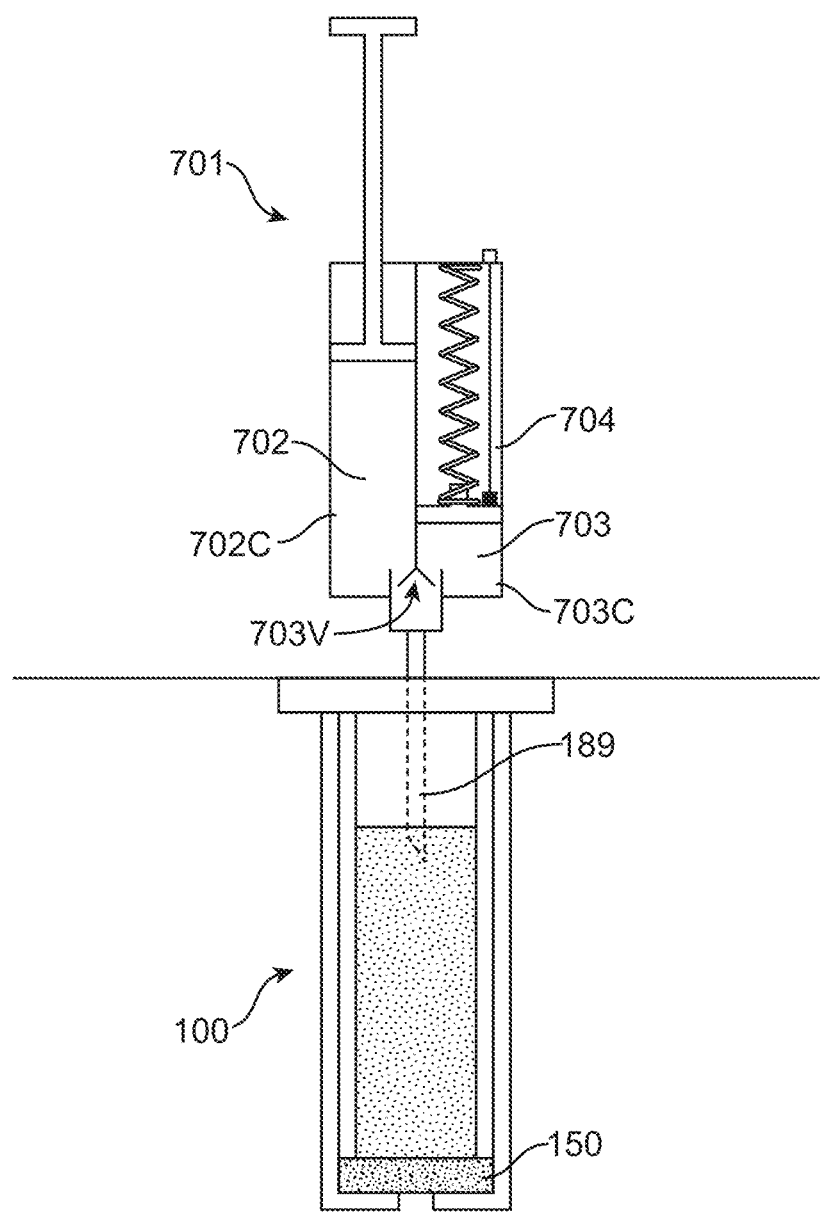
FIG. 7 shows a therapeutic device coupled to an injector that removes material from the device and injects therapeutic agent into the device, according to variations described herein.

FIG. 7 shows a therapeutic device 100 coupled to an injector 701 that removes material from the device and injects therapeutic agent 702 into the device. The injector picks up spent media 703 and refills the therapeutic device with fresh therapeutic agent. The therapeutic agent is injected into the therapeutic device. The spent media is pulled up into the injector. The injector may comprise a stopper mechanism 704.

The injector 701 may comprise a first container 702C to contain a formulation of therapeutic agent 702 and a second container 703C to receive the spent media 703. Work in relation to variations suggests that the removal of spent media 703 comprising material from the container reservoir of the therapeutic device can remove particulate from the therapeutic device, for example particles comprised of aggregated therapeutic agent such as protein. The needle 189 may comprise a double lumen needle with a first lumen coupled to the first container and a second lumen coupled to the second container, such that spent media 703 passes from the container reservoir of device 100 to the injector. A valve 703V, for example a vent, can be disposed between the second lumen and the second container. When the valve is open and therapeutic agent is injected, spent media 703 from the container reservoir of the therapeutic device 100 passes to the second container of the injector, such that at least a portion of the spent media within the therapeutic device is exchanged with the formulation. When the valve is closed and the therapeutic agent is injected, a portion of the therapeutic agent passes from the reservoir of the therapeutic device into the eye. For example, a first portion of formulation of therapeutic agent can be injected into therapeutic device 100 when the valve is open such that the first portion of the formulation is exchanged with material disposed within the reservoir; the valve is then closed and a second portion of the formulation is injected into therapeutic device 100 such that at least a portion of the first portion passes through the porous structure into the eye. Alternatively or in combination, a portion of the second portion of injected formulation may pass through the porous structure when the second portion is injected into the eye. The second portion of formulation injected when the valve is closed may correspond to a volume of formulation that passes through the porous structure into the vitreous humor to treat the patient immediately.

The needle 189 may comprise a dual lumen needle, for example as described in U.S. patent application Ser. No. 12/696,678, filed Jan. 29, 2010, entitled "POSTERIOR SEGMENT DRUG DELIVERY," published Oct. 7, 2010 as U.S. Patent Publication No. 2010/0255061, the full disclosure of which has been previously incorporated herein by reference.

The penetrable barrier 184, for example the septum, can be inserted into the access port 180. The penetrable barrier may comprise an elastic material sized such that the penetrable barrier can be inserted into the access port 180. The penetrable barrier may comprise one or more elastic materials such as siloxane or rubber. The penetrable barrier may comprise tabs 184T to retain the penetrable barrier in the access port. The penetrable barrier 184 may comprise a beveled upper rim 184R sized to seal the access port 180. The access port 180 of the reservoir container 130 may comprise a beveled upper surface to engage the beveled rim and seal the penetrable barrier against the access port 180 when the tabs 184T engage an inner annular or elongate channel of the access port. The penetrable barrier 184 may comprise an opaque material, for example a grey material, for example silicone, such that the penetrable barrier can be visualized by the patient and treating physician.

The reservoir container 130 of the device may comprise a rigid biocompatible material that extends at least from the retention structure to the rigid porous structure, such that the reservoir comprises a substantially constant volume when the therapeutic agent is released with the rigid porous structure so as to maintain a stable release rate profile, for example when the patient moves. Alternatively or in combination, the reservoir container 130 may comprise an optically transmissive material such that the reservoir container 130 can be translucent, for example transparent, such that the chamber of reservoir 140 can be visualized when the device is loaded with therapeutic agent outside the patient prior to implantation, for example when injected with a formulation of therapeutic agent prior to implantation in the physician's office. This visualization of the reservoir 140 can be helpful to ensure that the reservoir 140 is properly filled with therapeutic agent by the treating physician or assistant prior to implantation. The reservoir container may comprise one or more of many biocompatible materials such as acrylates, polymethylmethacrylate, siloxanes, metals, titanium stainless steel, polycarbonate, polyetheretherketone (PEEK), polyethylene, polyethylene terephthalate (PET), polyimide, polyamide-imide, polypropylene, polysulfone, polyurethane, polyvinylidene fluoride or PTFE. The biocompatible material of the reservoir container may comprise an optically transmissive material such as one or more of acrylate, polyacrylate, methlymethacraylate, polymethlymethacrylate (PMMA), polyacarbonate or siloxane. The reservoir container 130 can be machined from a piece of material, or injection molded, so as to form the retention structure 120 comprising flange 122 and the elongate narrow portion 120NE. The flange 122 may comprise a translucent material such that the physician can visualize tissue under the flange to assess the patient and to decrease appearance of the device 100 when implanted. The reservoir container 130 may comprise a channel extending along axis 100A from the access port 180 to porous structure 150, such that formulation injected into device 100 can be released in accordance with the volume of the reservoir and release rate of the porous structure 150, as described herein. The porous structure 150 can be affixed to the distal end of therapeutic device 100, for example with glue. Alternatively or in combination, the distal end of the reservoir container 130 may comprise an inner diameter sized to receive the porous structure 150, and the reservoir container 130 may comprise a stop to position the porous structure 150 at a predetermined location on the distal end so as to define a predetermined size of reservoir 140.

TUNING OF THERAPEUTIC DEVICE FOR SUSTAINED RELEASE BASED ON AN INJECTION OF A FORMULATION OF THERAPEUTIC AGENT HAVING ONE OR MORE OF A LARGE MOLECULAR WEIGHT STABILIZER, ERODIBLE PARTICLES, OR BINDING AGENT PARTICLES, OR COMBINATIONS THEREOF

The tuned release can be used to determine the release of the therapeutic agent and stabilizer combined with one or more of the binding agent or erodible material as described herein. One or more of calculations, computer modeling, numerical simulations or finite element analysis can be used to determine the release rate profile of the therapeutic agent, as described herein. The affect of one or more of the stabilizer, reversible binding agent particles, or erodible particles on the modulation of the rate of release can be determined, for example.

In many variations, the stabilizer may comprise a molecular weight that corresponds to at least about 20% of the molecular weight of the therapeutic agent.

The amount of stabilizer and release rate profile of the stabilizer through the porous structure can be determined based on the concentration of the stabilizer, the volume of the reservoir, and the release rate index of the porous structure 150. The release rate profile may also include the fraction of stabilizer complexed with the therapeutic agent and the corresponding diffusion coefficient of the complexed therapeutic agent.

The reversible binding characteristics of the therapeutic agent and binding agent can be used to determine the release rate profile. The amount of therapeutic agent in solution, the amount of therapeutic agent complexed with the stabilizer, and the amount of therapeutic agent reversibly bound to the binding agent can be determined, for example as a function of pH. The amount of therapeutic agent in solution and the amount of therapeutic agent complexed with the stabilizer and corresponding diffusion coefficients can be used to determine the rate of release of the therapeutic agent through the porous structure. The rate of release of therapeutic agent through the porous structure may comprise the rate of release of the therapeutic agent in solution and the therapeutic agent complexed with the stabilizer.

In many variations, the binding agent is sized such that diffusion through the porous structure is substantially inhibited, and the particles of binding agent may have dimensions greater than the channels of the porous structure 150, or smaller than the channels of the porous structure. For example, particles greater than 5 um may not pass through the porous structure, even when there is convection of fluid through the porous structure such as when the device is refilled with formulation (i.e., the particles may be trapped in the porous structure as in a depth filter or may be trapped on the surface of the porous structure as in a surface filter). Although particles having a size as large as the size of the channels of porous structure 150 may pass through the channels of the porous structure under convection, these particles may have no substantial diffusive flux because the diffusion coefficient may be substantially larger than the diffusion coefficient of the therapeutic agent. For example, particles having a size of about 0.050 um (50 nm) may have a diffusion coefficient that is about one tenth of the diffusion coefficient of ranibizumab, for example. The particles may comprise a size within a range from about 50 um to about 0.5 um, for example, based substantially on the molecular weight of the therapeutic agent and the size of the channels of the porous structure 150.

The rate of erosion of the erodible particles can be used to determine the rate of generation of protons to maintain the pH in the reservoir chamber below about 7. The rate of generation of protons may correspond to one or more of the pH, ionic strength or osmolarity of the components of the formulation 190 in the reservoir chamber of the device.

The therapeutic device 100 can be tuned to deliver a target therapeutic concentration profile based on the volume of formulation injected into the device. The injected volume may comprise a substantially fixed volume, for example within about +/−30% of an intended predetermined target volume. The volume of the reservoir can be sized with the release rate index so as to release the therapeutic agent for an extended time substantially greater than the treatment time of a corresponding bolus injection. The device can also be tuned to release the therapeutic agent based on the half-life of the therapeutic agent in the eye. The device volume and release rate index comprise parameters that can be tuned together based on the volume of formulation injected and the half-life of the therapeutic agent in the eye. The following equations can be used to determine therapeutic device parameters suitable for tuning the device.

$$\text{Rate} = Vr(dCr/dt) = -D(PA/TL)Cr$$

where Rate=Rate of release of therapeutic agent from device
Cr=concentration of therapeutic agent in reservoir
Vr=volume of reservoir
D=Diffusion constant
PA/TL=RRI
P=porosity
A=area
T=tortuosity=F=channel parameter.
For a substantially fixed volume injection,
Cr0=(Injection Volume)(Concentration of Formulation)/Vr
Where Cr0=initial concentration in reservoir following injection of formulation
For Injection Volume=50 uL $$Cr0=(0.05\text{ mL})(10\text{ mg/mL})/Vr(1000\text{ ug/1 mg})=500\text{ ug}/Vr$$

$$\text{Rate}=x(500\text{ ug})\exp(-xt)$$

where $t$=time $$x=(D/Vr)(PA/TL)$$

With a mass balance on the vitreous
Vv(dCv/dt)=Rate from device=kVvCv
where Vv=volume of vitreous (about 4.5 ml)
Cv=concentration of therapeutic agent in vitreous
k=rate of drug from vitreous (proportional to 1/half-life of drug in vitreous)
For the situation appropriate for the variations as described herein where Cv remains substantially constant and changes slowly with time (i.e. dCv/dt is approximately 0),
Cv=(Rate from device)/(kVv)
Since kVv is substantially constant, the max value of Cv will correspond to conditions that maximize the Rate from the device. At a given time since injection into the device (e.g., 180 days), the maximum Cv is found at the value of x that provides the maximum rate. The optimal value of x satisfies d(Rate)/dx=0 at a given time.

$$\text{Rate}=500(x)\exp(-xt)=f(x)g(x)\text{ where }f(x)=500x\text{ and }g(x)=\exp(-xt)$$

$$d(\text{Rate})/dx=f'(x)g(x)+f(x)g'(x)=500(1-xt)\exp(-xt)$$

For a given time, t, d(Rate)/dx=0 when 1−xt=0 and xt=1
The rate is maximum when (D/Vr)(PA/TL)t=1.
For a given volume, optimal PA/TL=optimal RRI=Vr/(Dt)
Therefore the highest Cv at a given time, t, occurs for the optimal RRI=(PA/FL) for a given Vr.
Also, the ratio (Vr)/(RRI)=(Vr)/(PA/TL)=Dt will determine the optimal rate at the time.

The above equations provide approximate optimized values that, when combined with numerical simulations, can provide optimal values of Vr and PA/TL. The final optimum value can depend on additional parameters, such as the filling efficiency.

The above parameters can be used to determine the optimal RRI, and the therapeutic device can be tuned to the volume of formulation injected into the device with a device reservoir volume and release rate index within about +/−50% of the optimal values, for example +/−30% of the optimal values. For example, for an optimal release rate index of the porous structure and an optimal reservoir volume sized to receive a predetermined quantity of therapeutic agent, e.g., 50 uL, so as to achieve therapeutic concentrations above a minimum inhibitory concentration for a predetermined extended time such as 90 days, the maximum volume of the reservoir can be limited to no more than about twice the optimal volume. This tuning of the reservoir volume and the porous structure to the injected volume of the formulation can increase the time of release of therapeutic amounts from the device as compared to a much larger reservoir volume that receives the same volume of injectable formulation. Although many examples as described herein show a porous frit structure and reservoir volume tuned together to receive a quantity of formulation and provide release for an extended time, the porous structure tuned with the reservoir may comprise one or more of a porous frit, a permeable membrane, a semi-permeable membrane, a capillary tube or a tortuous channel, nano-structures, nano-channels or sintered nano-particles, and the release rate characteristics can be determined, for example a release rate index, so as to tune the one or more porous structures and the volume to receive the quantity of the formulation and release therapeutic amounts for an extended time.

As an example, the optimal RRI at 180 days can be determined for a reservoir volume of about 125 uL. Based on the above equations (Vr/Dt)=optimal RRI, such that the optimal RRI at 180 days is about 0.085 for the 50 uL formulation volume injected into the device. The corresponding Cv is about 3.19 ug/mL at 180 days based on the Rate of drug released from the device at 180 days and the rate of the drug from the vitreous (k corresponding to a half life of about 9 days). A device with a container reservoir volume of 63 uL and RRI of 0.044 will also provide the optimal Cv at 180 days since the ratio of Vr to PA/TL is also optimal. Although an optimal value can be determined, the therapeutic device can be tuned to provide therapeutic amounts of drug at a targeted time, for example 180 days, with many values of the reservoir volume and many values of the release rate index near the optimal values, for example within about +/−50% of the optimal values. Although the volume of the reservoir can be substantially fixed, the volume of the reservoir can vary, for example within about +/−50% as with an expandable reservoir such as a balloon reservoir.

The half-life of the drug in the vitreous humor of the eye can be determined based on the therapeutic agent and the type of eye, for example human, rabbit or monkey, such that the half-life may be determined based on the species of the eye, for example. With at least some animal models the half life of the therapeutic agent in the vitreous humor can be shorter than for human eyes, for example by a factor of about two in at least some instances. For example, the half-life of the therapeutic agent Lucentis™ (ranibizumab) can be about nine days in the human eye and about two to four days in the rabbit and monkey animal models. For small molecules, the half life in the vitreous humor of the human eye can be about two to three hours and can be about one hour in the monkey and rabbit animal models. The therapeutic device can be tuned to receive the volume of formulation based on the half-life of the therapeutic agent in the human vitreous humor, or an animal vitreous humor, or combinations thereof. The half life of the therapeutic agent in the eye can be determined empirically based on the type of eye and the therapeutic agent, such that the reservoir and porous structure can be tuned together so as to receive the volume of formulation and provide therapeutic amounts for the extended time.

The formulation 190 may comprise components that result in slowing the diffusion of the therapeutic agent until those components are depleted via release to the vitreous (i.e., effective diffusion coefficient for the therapeutic agent that is lower than that in a dilute solution of the therapeutic agent in water). This may occur due to an increase in the viscosity of the formulation or due to interactions. The component that slows down diffusion may be a high concentration of the therapeutic agent itself. As time proceeds, depletion of the component may correspond to an increase in diffusion coefficient of the therapeutic agent, thereby generating a release profile that is more constant.

Soluble, high molecular weight species that interact with the therapeutic agent 110 of interest can be added to the formation. The interaction of the therapeutic agent 110 and the high molecular weight species will modulate the diffusion of the therapeutic agent 110 through the solution, and thus affect the release rate of the therapeutic agent 110 from the device 100.

Insoluble resins such as ion exchange resins or resins containing hydrophobic groups that reversibly bind the therapeutic agent 110 of interest can be added to the formulation. The interaction of the resins and the therapeutic agent 110 will affect the concentration of the therapeutic agent 110 in solution, and thus modulate the release rate of the therapeutic agent 110 from the device 100.

High molecular weight stabilizers can be added to the formulation of the therapeutic agent 110 of interest. If the molecular weight of the stabilizer is approximately the same as that of the therapeutic agent 110, the two will diffuse from the therapeutic device 100 at approximately the same rate, thus keeping the ratio of stabilizer to therapeutic agent 110 approximately constant over time. If the molecular weight of the stabilizer is higher than that of the therapeutic agent 110, the ratio of stabilizer to therapeutic agent 110 in the device will actually increase over time. Both of these scenarios may increase the stability of the therapeutic agent 110 in the device during the delivery period.

Figure 8A:
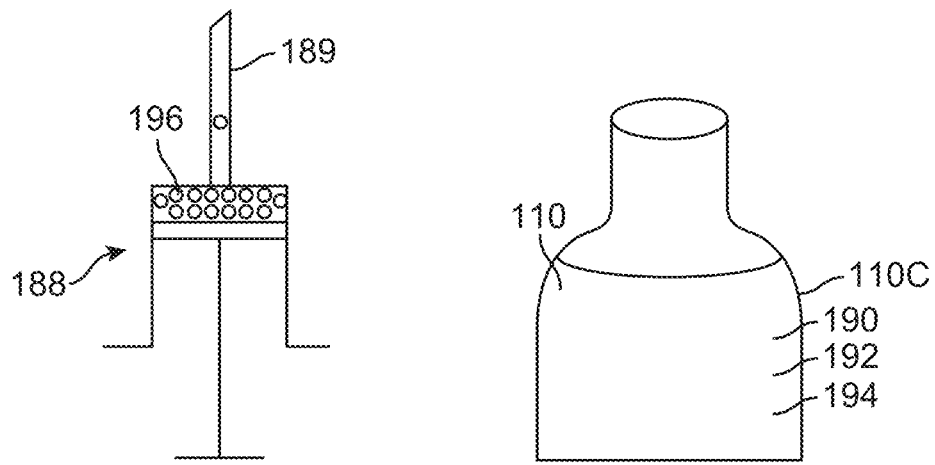
FIG. 8A shows an apparatus comprising a first container having the formulation of therapeutic agent and the second container comprising a syringe having particles of an erodible material loaded thereon to generate a proton of an acid when mixed with the formulation, in accordance with variations described herein.

FIG. 8A shows an apparatus comprising a first container 110C having the formulation 190 of therapeutic agent and the second container comprising a syringe 188 having erodible material 196 to generate a proton of an acid. The particles of erodible material can be mixed with the formulation of therapeutic agent within about one day or less prior to injection such that erosion of the material is decreased and also to maintain the pH of the formulation above about 4.5, for example. The first container 110C may contain formulation 190 comprising the therapeutic agent 110, the stabilizer 192 and the reversible binding agent 194, and may contain a buffer such as a phosphate buffer, for example. The second container may comprise particles of erodible material in a substantially dry configuration so as to decrease erosion of the erodible material.

Figure 8B:
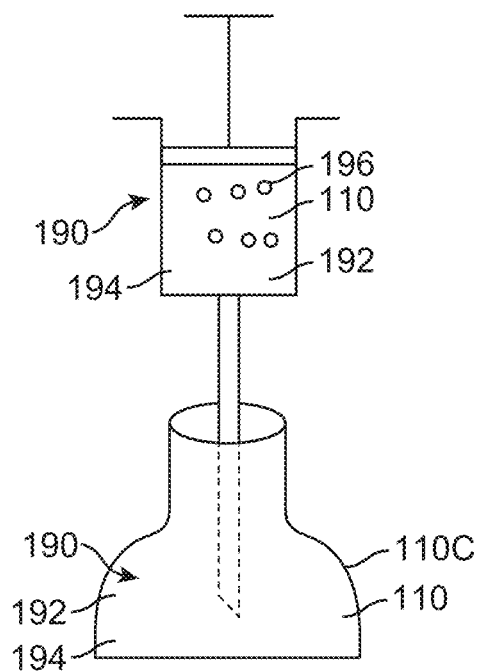
FIG. 8B shows the first and second containers as in FIG. 8A used to prepare the formulation of therapeutic agent prior to injection, in accordance with variations described herein.

FIG. 8B shows the syringe 188 as in FIG. 8A used to prepare the formulation of therapeutic agent prior to injection. A needle 189 can be inserted into container 110C and the formulation 190 drawn into the second container comprising syringe 188 so as to mix the formulation prior to injection into therapeutic device 100. The mixed formulation can be exchanged and the syringe may comprise an exchange syringe, for example.

Figure 8C:
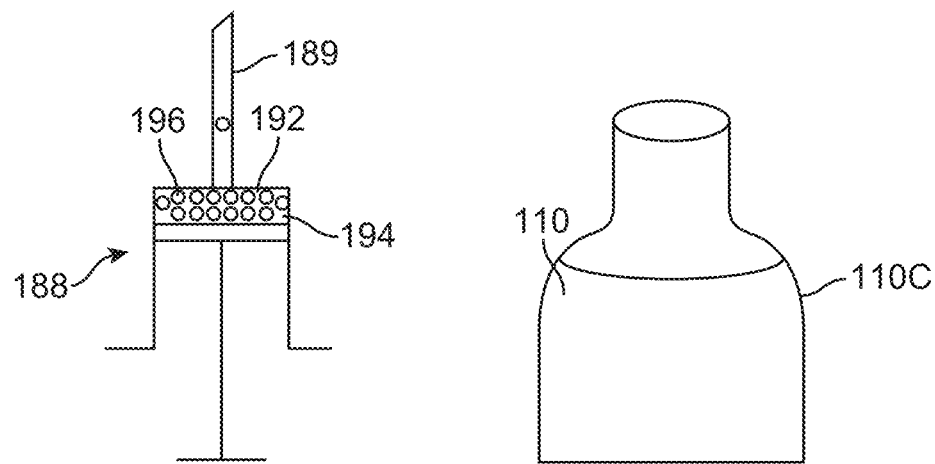
FIG. 8C shows an apparatus comprising a first container having a commercially available formulation of therapeutic agent and the second container comprising a syringe having one or more of, a stabilizer, a binding agent comprising porous particles, an erodible material to generate a proton of an acid, in accordance with variations described herein.
Figure 8D:
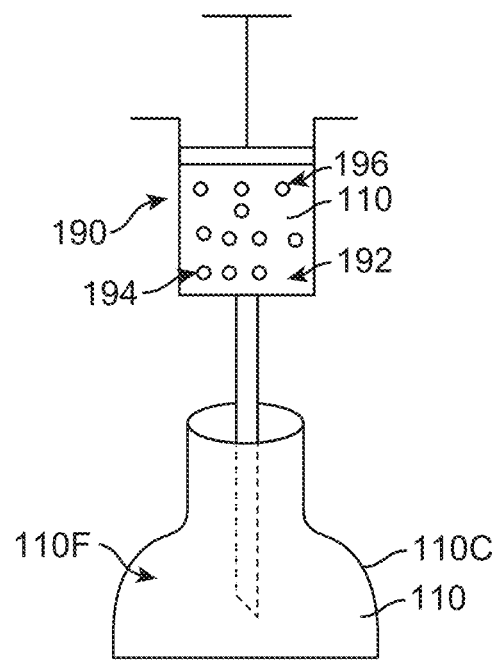
FIG. 8D shows the first and second containers as in FIG. 8C used to prepare the formulation of therapeutic agent prior to injection, in accordance with variations described herein.

FIG. 8C shows an apparatus comprising a first container having a commercially available formulation 110F of therapeutic agent, and the second container comprising a syringe 188 having one or more of, a stabilizer 192, a binding agent 194 comprising porous particles, or an erodible material 196 to generate a proton of an acid, in accordance with variations;

FIG. 8D shows the first and second containers as in FIG. 8C used to prepare the formulation 190 of therapeutic agent prior to injection. A needle 189 can be inserted into container 110C and the formulation 110F drawn into the second container comprising syringe 188 so as to mix and provide the formulation 190 prior to injection into therapeutic device 100. The mixed formulation can be exchanged and the syringe may comprise an exchange syringe, for example. The mixed formulation 190 prior to injection may comprise the therapeutic agent 110, and one or more of a stabilizer 192, a binding agent 194 comprising porous particles, or an erodible material 196 to generate a proton of an acid. For example, prior to drawing formulation 110F, the syringe 188 may comprise a stabilizer 192 and an erodible material 196 as a substantially dry combination, and the formulation 110F of container 110C may comprise Lucentis™. Upon drawing an amount of the commercially available formulation of Lucentis™ into the syringe, the formulation 190 can be provided for injection into therapeutic device 100. Syringe 188 may comprise a substantially single use disposable syringe, for example.

The first and second containers can be configured in many ways. For example, the second container may comprise a cartridge having the erodible material stored therein, in which the cartridge is configured to couple to a syringe having the formulation of the therapeutic agent contained therein, so as to mix the erodible material with the formulation upon injection into or exchange with a therapeutic device. The cartridge may be configured to couple to the needle and the syringe. For example, the cartridge may comprise a first end to couple to the syringe and a second end to couple to a needle. The container may comprise an amount of the particles corresponding to a volume of the reservoir chamber of the device so as to combine with an amount of the formulation corresponding to the volume of the reservoir chamber, so as to provide a concentration of particles and formulation loaded into device 100 corresponding to an intended target concentration of particles and formulation.

Determination of Isoelectric Point of Ranibizumab

Determining the isoelectric point of a protein can be used to determine the stability of a protein formulation, or to develop a related assay. The isoelectric point of Lucentis™ can be estimated from the primary amino acid sequence obtained from the Novartis package insert of Lucentis™ marketed in Australia, CAS number 347396-82-1.

The total number of ionizable acidic and basic amino acids were tabulated. The pKa values of the ionizable side groups were estimated using the Sigma-Aldrich table available on the World Wide Web (sigmaaldrich.com/life-science/metabolomics/bioultra-reagents/amino-acids.html).

The local environments in a protein can shift pKa values of single amino acids, but average values should be useful to estimate the overall effect. Table Y1 is a list of the sequence number position and total number of the acidic and basic amino acids present in Lucentis™. The acidic groups of Asp and Glu total 32 amino acids (pKa ~4), and the basic groups of Tyr, Lys, and Arg, (pKa~10) total 61 amino acids. Therefore with twice as many basic groups as acidic groups, Lucentis™ would be classified as a basic protein with an isoelectric point of about 8.0 to 9.0. After estimating the number of charges versus pH of a solution including the N-terminus and C-terminus, the plot in FIG. 4C shows the zero net charge state (isoelectric point) to be achieved at about pH 8.0 to 9.0.

TABLE Y1

Lucentis™ Amino Acid Positions and Total Number

|  | Asp | Glu | His | Tyr | Lys | Arg |
|---|---|---|---|---|---|---|
| A-chain | 28 | 1 | 31 | 27 | 43 | 19 |
|  | 63 | 6 | 107 | 32 | 65 | 38 |
|  | 73 | 46 | 174 | 54 | 76 | 66 |
|  | 90 | 57 | 210 | 60 | 98 | 67 |
|  | 111 | 89 | 230 | 80 | 127 | 87 |
|  | 154 | 158 |  |  | 94 | 139 |
|  | 218 | 222 |  |  | 95 | 153 |
|  | 227 |  |  |  | 99 | 211 |
|  |  |  |  |  | 101 | 216 |
|  |  |  |  |  | 102 | 219 |
|  |  |  |  |  | 103 | 220 |
|  |  |  |  |  | 109 | 224 |
|  |  |  |  |  | 155 | 228 |
|  |  |  |  |  | 186 |  |
|  |  |  |  |  | 204 |  |
| B-chain | 1 | 81 | 55 | 32 | 39 | 18 |
|  | 17 | 105 | 189 | 36 | 42 | 61 |
|  | 28 | 123 | 198 | 49 | 45 | 108 |
|  | 70 | 143 |  | 86 | 103 | 142 |
|  | 82 | 161 |  | 87 | 107 | 211 |
|  | 122 | 165 |  | 91 | 126 |  |
|  | 151 | 187 |  | 140 | 145 |  |
|  | 167 | 195 |  | 173 | 149 |  |
|  | 170 | 213 |  | 186 | 169 |  |
|  | 175 |  |  | 192 | 183 |  |
|  |  |  |  |  | 188 |  |
|  |  |  |  |  | 190 |  |
|  |  |  |  |  | 207 |  |
| Total A & B | 18 | 16 | 8 | 25 | 26 | 10 |

The charge as a function of pH can be determined for many therapeutic agents as described herein, for example protein based therapeutic agents comprising a Fab antibody fragment and derivatives thereof.

EXPERIMENTAL

Experiments to determine empirically the release rate of the therapeutic agent and the stabilizer from the formulation 190 are described herein.

Example 1

A drug release study was performed using bovine serum albumin (BSA) as a model therapeutic agent and fluorescein as a model stabilizer, so as to show formation of ionic complexes between a model stabilizer and model therapeutic agent, in which the model stabilizer comprises on or more of an ionic group, a hydroxyl group, or an aromatic ring and the therapeutic agent comprises Fab antibody fragment. Similar complexes can be formed with higher molecular weight stabilizers as described herein, so as to decrease the rate of release of the therapeutic agent.

The release rate of BSA and fluorescein were measured from devices initially loaded with formulations listed in Table E1. Buffer containing trehalose, polysorbate 20, and histidine was prepared first and pH was adjusted to 5.5 using HCl. Then BSA and fluorescein was added and pH was determined by pH paper to be in the 6.1-6.5 and 6.6-7.0 range for Formulations I and II respectively.

Devices were fabricated containing sintered porous titanium cylinders (Mott Corporation) with a diameter of 0.038 inches and a thickness of 0.030 inches. The porous cylinders were mounted into devices machined from poly (methyl methacrylate) with a reservoir volume of 0.025 mL and a silicone septum. The devices expose one planar face of the porous titanium to the solution in the reservoir and the other planar face to the receiver solution in the vials.

The devices (n=6 or 7 for each formulation) were filled with 0.05 mL formulation using a tuberculin syringe and a 33 gauge needle inserted through the septum. Excess formulation was expressed through the porous titanium and rinsed off the device prior to the start of the drug release study by submerging in phosphate buffered saline (PBS). The devices were mounted on hangers to suspend the devices in the center of PBS in 1.5 mL microcentrifuge tubes. At periodic intervals, the reservoirs were moved to new tubes containing degassed PBS as the receiver fluid. The amount of BSA transported from the reservoir through the porous cylinder into the receiver fluid was determined by measuring the amount of BSA in the vials using a Micro BCA™ Protein Assay kit (Pierce, 23235) on a Molecular Devices Plate Reader. Fluorescein concentrations in the receiver fluid were determined from absorbance at 492 nm on the plate reader.

TABLE E1

Compositions of formulations injected into devices

|  | Formulation | |
|---|---|---|
|  | I | II |
| BSA (mg/mL) | 20 | 200 |
| Fluorescein (mg/mL) | 1 | 1 |
| Trehalose (wt %) | 10 | 10 |
| Polysorbate 20 (wt %) | 0.01 | 0.01 |
| Histidine HCl (M) | 0.01 | 0.01 |
| Sodium azide (wt %) | 0.02 | 0.02 |

Figure 9:
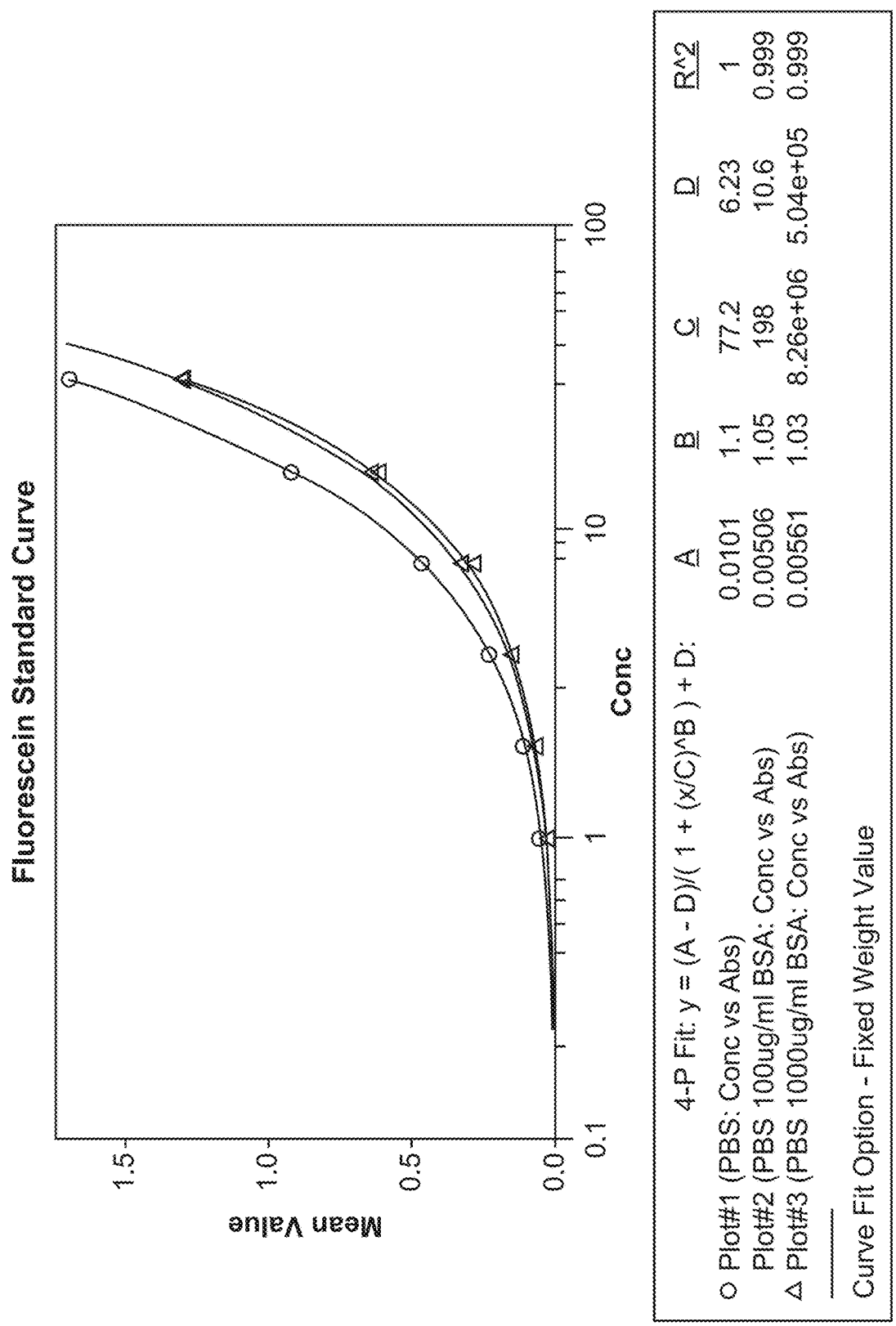
FIG. 9 shows calibration curves of fluorescein serially diluted in PBS or PBS containing 100 or 1000 ug/mL BSA, in accordance with variations described herein.

FIG. 9 shows calibration curves for absorbance of fluorescein in PBS versus PBS containing 100 and 1000 ug/mL BSA as the calibration curve diluent. For a given concentration of fluorescein, the fluorescein absorbance was lower in the standards containing BSA. When the standards containing BSA were assayed using the standards without BSA, the fluorescein concentrations were 74 and 69% of nominal values BSA concentrations of 100 and 1000 ug/mL, respectively, over a fluorescein concentration range of 2 to 30 ug/mL. It is known that fluorescein absorbance is stronger for the dianion form than the other ionic forms of fluorescein (Smith et al., Water S A, 28(4), 2002, 395-402). The lower absorbance from addition of BSA is consistent with formation of an ionic complex between fluorescein and BSA that may lower the concentration of fluorescein dianion in solution. Hence, the release of fluorescein in the presence of BSA is an example of a model stabilizer that forms an ionic complex with the model therapeutic agent.

Table E2 shows the concentrations of BSA and fluorescein measured in the receiver fluid at the start of the release study. The initial release rate of BSA is proportional to the BSA concentration, suggesting the effective diffusion coefficient was not dependent on concentration of BSA. Concentrations of fluorescein are corrected for the impact of the presence of BSA concentration measured in each sample, as described above. The release rate of fluorescein from the formulation containing 200 mg/mL BSA is slower by a factor of two compared to the formulation containing 20 mg/mL. The slower release rate can be described by an effective diffusion coefficient that is lower by a factor of two. These results demonstrate the ability to slow down diffusion and drug release of a model stabilizer by formation of ionic complexes between a model stabilizer and model therapeutic agent.

TABLE E2

Measured concentrations and initial release rates of BSA and fluorescein from Formulations I and II.

|  | Formulation I (20 mg/mL BSA) | | Formulation II (200 mg/mL BSA) | |
|---|---|---|---|---|
|  | Mean | SD | Mean | SD |
| Measured BSA in Receiver (ug/mL) | 105 | 4 | 1154 | 135 |
| Measured fluorescein in Receiver (ug/mL) | 10.9 | 0.5 | 4.6 | 0.5 |
| BSA rate (ug/mL) | 13.3 | 0.5 | 147.8 | 18.4 |
| BSA rate, normalized by initial BSA conc | 0.665 | 0.026 | 0.739 | 0.092 |
| Fluorescein rate (ug/mL), uncorrected | 1.4 | 0.1 | 0.6 | 0.1 |
| Correction factor | 0.74 | 0.74 | 0.69 | 0.69 |
| Fluorescein rate (ug/mL), corrected | 1.9 | 0.1 | 0.8 | 0.1 |

Example 2 Erodible Particles

PLGA may be purchased from a number of supplies, for example, PURASORB® of Purac Biomaterials, RESOMER® of Boehringer Ingelheim, Lakeshore Biomaterials™ of Surmodics Pharmaceuticals and Lactel® of Durect. PLGA is available with a range of properties as stock or custom polymers. For example, Durect produces PLGA with time for resorption ranging from a few months to greater than 24 months. Any commercially available PLGA can be processed into monodisperse microspheres by using processes known in the art, such as single and double emulsion processing schemes. PLGA may be purchased as microparticles. For example, monodisperse PURASORB® PLGA 5004 microspheres are available from Nanomi with particle sizes ranging from 1 to 30 um, prepared by an emulsification technology, and supplied freeze-dried.

Microparticles 1 um in size from Naomi can be added to Lucentis™ at concentrations ranging from 0.01% to 1%. The microparticles can be added just prior to injection into devices. Control devices can also be injected with Lucentis™ only. Drug release testing could be performed as described in Example 1. The stability of ranibizumab could be tested by assays such as ELISA and Ion-Exchange Chromatography HPLC on samples of drug in the receiver fluid. In addition, the contents in the reservoir of the devices could be harvested to assay for drug stability and measurement of pH by, for example, pH paper.

Example 3 Stabilizers

Various forms (e.g., cellulose acetate, ethylcellulose, carboxymethylcellulose, methylcellulose) and molecular weights of cellulose can be purchased from suppliers such as Spectrum Chemicals and Sigma-Aldrich. Excipients can be removed from Lucentis™ by dialysis to obtain ranibizumab. Then, excipients of choice can be added to prepare the desired formulations. An example would be 10 mg/mL ranibizumab, 10% carboxymethyl cellulose with a molecular weight of about 10 kDa, 0.01% polysorbate 20, 10 mM histidine HCl pH 5.5.

Devices can be injected with the various formulations and Lucentis™ as a control and subjected to drug release testing and stability assays as described in Example 2.

Example 4 Stabilizers and Erodible Particles

Stabilizers can be encapsulated into erodible particles using single and double emulsion techniques. PLGA and stabilizers listed in Examples 2 and 4 and buffers such as histidine hydrochloride can be dissolved in solvents such as dichloromethane, tetrahydrofuran, ethyl acetate, chloroform, hexafluoroisopropanol, and acetone. Surfactant such as polysorbate 20 at concentrations on the order of 0.01% can be added to water and the PLGA and stabilizers dissolved in solvent, and sonication applied to form an emulsion. Solvent can be removed to yield the particles. The particles can be added to Lucentis™ at concentrations on the order of 1%. Devices can be injected with the various formulations and Lucentis™ as a control and subjected to drug release testing and stability assays as described in Example 2.

Example 5 Micelle Stabilizer

Excipients can be removed from Lucentis™ by dialysis to obtain ranibizumab. A series of samples can be generated with composition identical to Lucentis™ but with a range of polysorbate 20 concentrations, from 0.0005% to 0.1%. Surface tension measurements may be performed with a Wilhemy plate to determine the CMC; i.e., polysorbate 20 concentration threshold for constant surface tension. Devices can then be filled with formulations containing polysorbate 20 concentrations that are 0, 1, 5 and 20 times the CMC. These devices can be subjected to drug release testing and stability assays as described in Example 2.

TABLE 1A

Therapeutic Agent List

| Generic Name | Brands (Companies) | Category | Indication | Molecular Weight |
|---|---|---|---|---|
| 2-Methoxyestradiol analogs | (Paloma Pharmaceuticals) | Angiogenesis inhibitors | AMD | |
| 3-aminothalidomide | | | | |
| 13-cis retinoic acid | Accutane TM (Roche Pharmaceuticals) | | | |
| A0003 | (Aqumen BioPharmaceuticals) | A0003 | AMD | |
| A5b1 integrin inhibitor | (Jerini Ophthalmic); (Ophthotech) | Inhibitors of a5b1 integrin | AMD | |
| Abarelix | Plenaxis ™ (Praecis Pharmaceuticals) | Anti-Testosterone Agents; Antineoplastic Agents | For palliative treatment of advanced prostate cancer. | 37731 |

TABLE 1A-continued

Therapeutic Agent List

| Generic Name | Brands (Companies) | Category | Indication | Molecular Weight |
|---|---|---|---|---|
| Abatacept | Orencia ™ (Bristol-Myers Squibb) | Antirheumatic Agents | For the second line reduction of the signs and symptoms of moderate-to-severe active rheumatoid arthritis, inducing inducing major clinical response, slowing the progression of structural damage, and improving physical function in adult patients who have | 37697 |
| Abciximab | ReoPro ™; ReoPro ™ (Centocor) | Anticoagulants; Antiplatelet Agents | For treatment of myocardial infarction, adjunct to percutaneous 89oronary intervention, unstable angina | 42632 |
| ABT-578 | (Abbott Laboratories) | Limus Immunophilin Binding Compounds | | |
| Acetonide | | | | |
| Adalimumab | Humira ™ (Abbott Laboratories) | Antirheumatic Agents; Immunomodulatory Agents | Uveitis, AMD | 25645 |
| Aldesleukin | Proleukin ™; Proleukin ™ (Chiron Corp) | Antineoplastic Agents | For treatment of adults with metastatic renal cell carcinoma | 61118 |
| Alefacept | Amevive ™ | Immunomodulatory Agents; Immunosuppressive Agents | For treatment of moderate to severe chronic plaque psoriasis | 42632 |
| Alemtuzumab | Campath ™; Campath ™ (ILEX Pharmaceuticals LP); MabCampath ™ | Antineoplastic Agents | For treatment of B-cell chronic lymphocytic leukemia | 6614 |
| Alpha-1-proteinase inhibitor | Aralast ™ (Baxter); Prolastin ™ (Talecris Biotherapeutics C formerly Bayer) | Enzyme Replacement Agents | For treatment of panacinar emphysema | 28518 |
| Alteplase | Activase ™ (Genentech Inc) | Thrombolytic Agents | For management of acute myocardial infarction, acute ischemic strok and for lysis of acute pulmonary emboli | 54732 |
| AMG-1470 | | | | |
| Anakinra | Kineret ™ (Amgen Inc) | Anti-Inflammatory Agents, Non-Steroidal; Antirheumatic Agents; Immunomodulatory Agents | For the treatment of adult rheumatoid arthritis. | 65403 |
| Anecortave acetate | | | | |
| Angiostatin | | | | |
| Anistreplase | Eminase ™ (Wulfing Pharma GmbH) | Thrombolytic Agents | For lysis of acute pulmonary emboli, intracoronary emboli and management of myocardial infarction | 54732 |
| Anti-angiogenesis peptides | (Eyecopharm) | Anti-angiogenesis peptides | AMD | |
| Anti-angiogenesis antibodies, TRC093, TRC105 | (TRACON Pharma) | Anti-angiogenesis antibodies | AMD | |
| Anti-angiogeric bifunctional protein | Icon-1 ™ (Iconic Therapeutics) | Anti-angiogeric bifunctional protein, Icon-1 | AMD | |
| Anti-endothelial growth factor | | | | |

TABLE 1A-continued

Therapeutic Agent List

| Generic Name | Brands (Companies) | Category | Indication | Molecular Weight |
|---|---|---|---|---|
| Antihemophilic Factor | Advate ™; Alphanate ™; Bioclate ™; Helixate ™; Helixate FS ™; Hemofil M ™; Humate-P ™; Hyate:C ™; Koate-HP ™; Kogenate ™; Kogenate FS ™; Monarc-M ™; Monoclate-P ™; ReFacto ™; Xyntha ™ | Coagulants; Thrombotic Agents | For the treatment of hemophilia A, von Willebrand diseae and Factor XIII deficiency | 70037 |
| Antithymocyte globulin | Genzyme); Thymoglobulin ™ (SangStat Medical | Immunomodulatory Agents | For prevention of renal transplant rejection | 37173 |
| Anti-hypertensive MC1101 Anti-platelet devired growth factor | (MacuCLEAR) | Anti-hypertensive MC1101 | AMD | |
| Anti-VEGF | (Neurotech); Avastin ™ (NeoVista) | Anti-VEGF | AMD | |
| AP23841 | (Ariad) | Limus Immunophilin Binding Compounds | | |
| ARC1905 | Ophthotech | Complement Cascade Inhibitor (Factor C5) | | |
| Aprotinin | Trasylol ™ | Antifibrinolytic Agents | For prophylactic use to reduce perioperative blood loss and the need for blood transfusion in patients undergoing cardiopulmonary bypass in the course of coronary artery bypass graft surgery who are at an increased risk for blood loss and blood transfusio | 90569 |
| Arcitumomab | CEA-Scan ™ | Diagnostic Agents; Imaging Agents | For imaging colorectal tumors | 57561 |
| Asparaginase | Elspar ™ (Merck & Co. Inc) | Antineoplastic Agents | For treatment of acute lympocytic leukemia and non-Hodgkins lymphoma | 132.118 |
| Axitinib | | Tyrosine Kinase Inhibitors | | 386 |
| Basiliximab | Simulect ™ (Novartis Pharmaceuticals) | Immunomodulatory Agents; Immunosuppressive Agents | For prophylactic treatment of kidney transplant rejection | 61118 |
| Becaplermin | Regranex ™; Regranex ™ (OMJ Pharmaceuticals) | Anti-Ulcer Agents; Topical | For topical treatment of skin ulcers (from diabetes) | 123969 |
| Bevacizumab | Avastin ™; Avastin ™ (Genentech Inc) | Antiangiogenesis Agents; Antineoplastic Agents | For treatment of metastatic colorectal cancer | 27043 |
| Bivalirudin | Angiomax ™; Angiomax ™ (Medicines Co or MDCO); Angiox ™ | Anticoagulants; Antithrombotic Agents | For treatment of heparin-induced thrombocytopenia | 70037 |
| Bortezomib | | Proteosome Inhibitors | | |
| Bosutinib | | Tyrosine Kinase Inhibitors | | 530 |

TABLE 1A-continued

Therapeutic Agent List

| Generic Name | Brands (Companies) | Category | Indication | Molecular Weight |
|---|---|---|---|---|
| Botulinum Toxin Type A | BOTOX ™ (Allegran Inc); BOTOX Cosmetic ™ (Allegran Inc); Botox ™; Dysport ™ | Anti-Wrinkle Agents; Antidystonic Agents; Neuromuscular Blocking Agents | For the treatment of cervical dystonia in adults to decrease the severity of abnormal head position and neck pain associated with cervical dystonia. Also for the treatment of severe primary axillary hyperhidrosis that is inadequately managed with topical | 23315 |
| Botulinum Toxin Type B | Myobloc ™ (Solstice Neurosciences); Neurobloc ™ (Solstice Neurosciences) | Antidystonic Agents | For the treatment of patients with cervical dystonia to reduce the severity of abnormal head position and neck pain associated with cervical dystonia. | 12902 |
| C5 inhibitor | (Jerini Ophthalmic); (Ophthotech) | Inhibitors of C5 | AMD | |
| Cal101 | Calistoga | PI3Kdelta Inhibitor | AMD, DME | |
| Canstatin | | | | |
| Capromab | ProstaScint ™ (Cytogen Corp) | Imaging Agents | For diagnosis of prostate cancer and detection of intra-pelvic metastases | 84331 |
| Captopril | | ACE Inhibitors | | |
| CCI-779 | (Wyeth) | Limus Immunophilin Binding Compounds | | |
| Cediranib | | Tyrosine Kinase Inhibitors | | 450 |
| Celecoxib | | Cyclooxygenase Inhibitors | | |
| Cetrorelix | Cetrotide ™ | Hormone Antagonists; Infertility Agents | For the inhibition of premature LH surges in women undergoing controlled ovarian stimulation | 78617 |
| Cetuximab | Erbitux ™; Erbitux ™ (ImClone Systems Inc) | Antineoplastic Agents | For treatment of metastatic colorectal cancer. | 42632 |
| Choriogonadotropin alfa | Novarel ™; Ovidrel ™. Pregnyl ™; Profasi ™ | Fertility Agents; Gonadotropins | For the treatment of female infertility | 78617 |
| Cilary neurotrophic factor | (Neurotech) | Cilary neurotrophic factor | AMD | |
| Coagulation Factor IX | Benefix ™ (Genetics Institute) | Coagulants; Thrombotic Agents | For treatment of hemophilia (Christmas disease). | 267012 |
| Coagulation factor VIIa | NovoSeven ™ (Novo Nordisk) | Coagulants; Thrombotic Agents | For treatment of hemorrhagic complications in hemophilia A and B | 54732 |
| Colchicines | | | | |
| Collagenase | Cordase ™; Santyl ™ (Advance Biofactures Corp); Xiaflextm ™ | Anti-Ulcer Agents; Topical | For treatment of chronic dermal ulcers and severe skin burns | 138885 |
| Complement factor H recombinant | (Optherion); (Taligen Therapeutics) | Complement factor H recombinant | AMD, Geographic Atrophy | |
| Compstatin derivative peptide, POT-4 | (Potentia Pharmaceuticals) | Complement Factor C3 Inhibitors; Compstatin Derivative Peptides | AMD | |

TABLE 1A-continued

Therapeutic Agent List

| Generic Name | Brands (Companies) | Category | Indication | Molecular Weight |
|---|---|---|---|---|
| Corticotropin | ACTH ™; Acethropan ™; Acortan ™; Acthar ™; Exacthin ™; H.P. Acthar Gel ™; Isactid ™; Purified cortrophin gel ™; Reacthin ™; Solacthyl ™; Tubex | Diagnostic Agents | For use as a diagnostic agent in the screening of patients presumed to have adrenocortical insufficiency. | 33927 |
| Cosyntropin | Cortrosyn ™; Synacthen depot ™ | Diagnostic Agents | For use as a diagnostic agent in the screening of patients presumed to have adrenocortical insufficiency. | 33927 |
| Cyclophilins | | Limus Immunophilin Binding Compounds | | |
| Cyclosporine | Gengraf ™ (Abbott labs); Neoral ™ (Novartis); Restasis ™; Restasis ™ (Allergan Inc); Sandimmune ™ (Novartis); Sangcya ™ | Antifungal Agents; Antirheumatic Agents; Dermatologic Agents; Enzyme Inhibitors; Immunomodulatory Agents; Immunosuppressive Agents | For treatment of transplant rejection, rheumatoid arthritis, severe psoriasis | 32953 |
| Daclizumab | Zenapax ™ (Hoffmann-La Roche Inc) | Immunomodulatory Agents; Immunosuppressive Agents | For prevention of renal transplant rejection; Uveitis | 61118 |
| Darbepoetin alfa | Aranesp ™ (Amgen Inc.) | Antianemic Agents | For the treatment of anemia (from renal transplants or certain HIV treatment) | 55066 |
| Dasatinib | | Tyrosine Kinase Inhibitors | | 488 |
| Defibrotide | Dasovas ™; Noravid ™; Prociclide ™ | Antithrombotic Agents | Defibrotide is used to treat or prevent a failure of normal blood flow (occlusive venous disease, OVD) in the liver of patients who have had bone marrow transplants or received certain drugs such as oral estrogens, mercaptopurine, and many others. | 36512 |
| Denileukin diftitox | Ontak ™ | Antineoplastic Agents | For treatment of cutaneous T-cell lymphoma | 61118 |
| Desmopressin | Adiuretin ™; Concentraid ™; Stimate ™ | Antidiuretic Agents; Hemostatics; Renal Agents | For the management of primary nocturnal enuresis and indicated as antidiuretic replacement therapy in the management of central diabetes insipidus and for the management of the temporary polyuria and polydipsia following head trauma or surgery in the pitu | 46800 |
| Dexamethasone | Ozurdex ™ (Allergan) | Glucocorticoid | DME, inflammation, macular edema following branch retinal vein occlusion (BRVO) or central retinal vein occlusion (CRVO) | 392 |

TABLE 1A-continued

Therapeutic Agent List

| Generic Name | Brands (Companies) | Category | Indication | Molecular Weight |
|---|---|---|---|---|
| Diclofenac | | Cyclooxygenase Inhibitors | | |
| Dithiocarbamate | | NFκB Inhibitor | | |
| Dornase Alfa | Dilor ™; Dilor-400 ™; Lufyllin ™; Lufyllin-400 ™; Neothylline ™; Pulmozyme ™ (Genentech Inc) | Enzyme Replacement Agents | For the treatment of cystic fibrosis. | 7656 (double strand) |
| Drotrecogin alfa | Xigris ™; Xigris ™ (Eli Lilly & Co) | Antisepsis Agents | For treatment of severe sepsis | 267012 |
| Eculizumab | Soliris ™; Soliris ™ (Alexion Pharmaceuticals) | Complement Cascade Inhibitor (Factor C5) | AMD | 188333 |
| Efalizumab | Raptiva ™; Raptiva ™ (Genentech Inc) | Immunomodulatory Agents; Immunosuppressive Agents | For the treatment of adult patients with moderate to severe chronic plaque psoriasis, who are candidates for phototherapy or systemic therapy. | 128771 |
| Endostatin | | | | |
| Enfuvirtide | Fuzeon ™; Fuzeon ™ (Roche Pharmaceuticals) | Anti-HIV Agents; HIV Fusion Inhibitors | For treatment of HIV AIDS | 16768 |
| Epoetin alfa | Epogen ™ (Amgen Inc.); Epogin ™ (Chugai); Epomax ™ (Elanex); Eprex ™ (Janssen-Cilag. Ortho Biologics LLC); NeoRecormon ™ (Roche); Procrit ™ (Ortho Biotech); Recormon ™ (Roche) | Antianemic Agents | For treatment of anemia (from renal transplants or certain HIV treatment) | 55066 |
| Eptifibatide | Integrilin ™; Integrilin ™ (Millennium Pharm) | Anticoagulants; Antiplatelet Agents; Platelet Aggregation Inhibitors | For treatment of myocardial infarction and acute coronary syndrome. | 7128 |
| Erlotinib | | Tyrosine Kinase Inhibitors | | 393 |
| Etanercept | Enbrel ™; Enbrel ™ (Immunex Corp) | Antirheumatic Agents; Immunomodulatory Agents | Uveitis, AMD | 25645 |
| Everolimus | Novartis | Limus Immunophilin Binding Compounds, mTOR | AMD | |
| Exenatide | Byetta ™; Byetta ™ (Amylin/Eli Lilly) | | Indicated as adjunctive therapy to improve glycemic control in patients with Type 2 diabetes mellitus who are taking metformin, a sulfonylurea, or a combination of both, but have not achieved adequate glycemic control. | 53060 |
| FCFD4514S | Genentech/Roche | Complement Cascade Inhibitor (Factor D) | AMD, Geographic Atrophy | |

TABLE 1A-continued

Therapeutic Agent List

| Generic Name | Brands (Companies) | Category | Indication | Molecular Weight |
|---|---|---|---|---|
| Felypressin | Felipresina ™ [INN-Spanish]; Felipressina ™ [DCIT]; Felypressin ™ [USAN:BAN:INN]; Felypressine ™ [INN-French]; Felypressinum ™ [INN-Latin]; Octapressin ™ | Renal Agents; Vasoconstrictor Agents | For use as an alternative to adrenaline as a 97ocalizing agent, provided that local ischaemia is not essential. | 46800 |
| Fenretinide | Sirion/reVision Therapeutics | Binding Protein Antagonist for Oral Vitamin A | AMD, Geographic Atrophy | |
| Filgrastim | Neupogen ™ (Amgen Inc.) | Anti-Infective Agents; Antineutropenic Agents; Immunomodulatory Agents | Increases leukocyte production, for treatment in non-myeloid cancer, neutropenia and bone marrow transplant | 28518 |
| FK605-binding proteins, FKBPs | | Limus Immunophilin Binding Compounds | | |
| Fluocinolone Acetonide | Retisert ™ (Bausch & Lomb); Iluvien ™ (Alimera Sciences, Inc.) | Glucocorticoid | Retinal inflammation, diabetic macular edema | 453 |
| Follitropin beta | Follistim ™ (Organon); Gonal F ™; Gonal-F ™ | Fertility Agents | For treatment of female infertility | 78296 |
| Fumagillin | | | | |
| Galsulfase | Naglazyme ™; Naglazyme ™ (BioMarin Pharmaceuticals) | Enzyme Replacement Agents | For the treatment of adults and children with Mucopolysaccharidosis VI. | 47047 |
| Gefitinib | | Tyrosine Kinase Inhibitors | | 447 |
| Gemtuzumab ozogamicin | Mylotarg ™; Mylotarg ™ (Wyeth) | Antineoplastic Agents | For treatment of acute myeloid leukemia | 39826 |
| Glatiramer Acetate | Copaxone ™ | Adjuvants, Immunologic; Immunosuppressive Agents | For reduction of the frequency of relapses in patients with Relapsing-Remitting Multiple Sclerosis. | 29914 |
| Glucagon recombinant | GlucaGen ™ (Novo Nordisk); Glucagon ™ (Eli Lilly) | Antihypoglycemic Agents | For treatment of severe hypoglycemia, also used in gastrointestinal imaging | 54009 |
| Goserelin | Zoladex ™ | Antineoplastic Agents; Antineoplastic Agents, Hormonal | Breast cancer; Prostate carcinoma; Endometriosis | 78617 |
| Human Serum Albumin | Albutein ™ (Alpha Therapeutic Corp) | Serum substitutes | For treatment of severe blood loss, hypervolemia, hypoproteinemia | 39000 |
| Hyaluronidase | Vitragan ™; Vitrase ™; Vitrase ™ (Ista Pharma) | Anesthetic Adjuvants; Permeabilizing Agents | For increase of absorption and distribution of other injected drugs and for rehydration | 69367 |
| Ibritumomab | Zevalin ™ (IDEC Pharmaceuticals) | Antineoplastic Agents | For treatment of non-Hodgkin's lymphoma | 33078 |
| Idursulfase | Elaprase ™ (Shire Pharmaceuticals) | Enzyme Replacement Agents | For the treatment of Hunter syndrome in adults and children ages 5 and older. | 47047 |
| Imatinib | | Tyrosine Kinase Inhibitors | AMD, DME | 494 |

TABLE 1A-continued

Therapeutic Agent List

| Generic Name | Brands (Companies) | Category | Indication | Molecular Weight |
|---|---|---|---|---|
| Immune globulin | Civacir ™; Flebogamma ™ (Instituto Grifols SA); Gamunex ™ (Talecris Biotherapeutics) | Anti-Infectives; Immunomodulatory Agents | For treatment of immunodeficiencies, thrombocytopenic purpura, Kawasaki disease, gammablobulinemia, leukemia, bone transplant | 42632 |
| Infliximab | Remicade ™ (Centocor Inc) | Immunomodulatory Agents; Immunosuppressive Agents | Uveitis, AMD | 25645 |
| Insulin Glargine recombinant | Lantus ™ | Hypoglycemic Agents | For treatment of diabetes (type I and II) | 156308 |
| Insulin Lyspro recombinant | Humalog ™ (Eli Lily); Insulin Lispro (Eli Lily) | Hypoglycemic Agents | For treatment of diabetes (type I and II) | 154795 |
| Insulin recombinant | Novolin R ™ (Novo Nordisk) | Hypoglycemic Agents | For treatment of diabetes (type I and II) | 156308 |
| Insulin, porcine | Iletin II ™ | Hypoglycemic Agents | For the treatment of diabetes (type I and II) | 156308 |
| Interferon Interferon Alfa-2a, Recombinant | Roferon A ™ (Hoffmann-La Roche Inc); Veldona ™ (Amarillo Biosciences) | Antineoplastic Agents; Antiviral Agents | For treatment of chronic hepatitis C, hairy cell leukemia, AIDS-related Kaposi's sarcoma, and chronic myelogenous leukemia. Also for the treatment of oral warts arising from HIV infection. | 57759 |
| Interferon Alfa-2b, Recombinant | Intron A ™ (Schering Corp) | Antineoplastic Agents; Antiviral Agents; Immunomodulatory Agents | For the treatment of hairy cell leukemia, malignant melanoma, and AIDS-related Kaposi's sarcoma. | 57759 |
| Interferon alfacon-1 | Advaferon ™; Infergen ™ (InterMune Inc) | Antineoplastic Agents; Antiviral Agents; Immunomodulatory Agents | For treatment of hairy cell leukemia, malignant melanoma, and AIDS-related Kaposi's sarcoma | 57759 |
| Interferon alfa-n1 | Wellferon ™ (GlaxoSmithKline) | Antiviral Agents; Immunomodulatory Agents | For treatment of venereal or genital warts caused by the Human Papiloma Virus | 57759 |
| Interferon alfa-n3 | Alferon ™ (Interferon Sciences Inc.); Alferon LDO ™; Alferon N Injection ™ | Antineoplastic Agents; Antiviral Agents; Immunomodulatory Agents | For the intralesional treatment of refractory or recurring external condylomata 100cuminate. | 57759 |
| Interferon beta-1b | Betaseron ™ (Chiron Corp) | Antiviral Agents; Immunomodulatory Agents | For treatment of relapsing/remitting multiple sclerosis | 57759 |
| Interferon gamma-1b | Actimmune ™; Actimmune ™ (InterMune Inc) | Antiviral Agents; Immunomodulatory Agents | For treatment of Chronic granulomatous disease, Osteopetrosis | 37835 |
| Lapatinib | | Tyrosine Kinase Inhibitors | | 581 |
| Lepirudin | Refludan ™ | Anticoagulants; Antithrombotic Agents; Fibrinolytic Agents | For the treatment of heparin-induced thrombocytopenia | 70037 |
| Lestaurtinib | | Tyrosine Kinase Inhibitors | | 439 |
| Leuprolide | Eligard ™ (Atrix Labs/QLT Inc) | Anti-Estrogen Agents; Antineoplastic Agents | For treatment of prostate cancer, endometriosis, uterine fibroids and premature puberty | 37731 |
| Lutropin alfa | Luveris ™ (Serono) | Fertility Agents | For treatment of female infertility | 78617 |
| Mecasermin | Increlex ™; Increlex ™ (Tercica); Iplex | | For the long-term treatment of growth failure in pediatric | 154795 |

TABLE 1A-continued

Therapeutic Agent List

| Generic Name | Brands (Companies) | Category | Indication | Molecular Weight |
|---|---|---|---|---|
| | | | patients with Primary IGFD or with GH gene deletion who have developed neutralizing antibodies to GH. It is not indicated to treat Secondary IGFD resulting from GH deficiency, malnutrition, hypoth | |
| Menotropins | Repronex ™ | Fertility Agents | For treatment of female infertility | 78617 |
| Methotrexate | | Immunomodulatory | Uveitis, DME | |
| mTOR inhibitors | | | | |
| Muromonab | Orthoclone OKT3 ™ (Ortho Biotech) | Immunomodulatory Agents; Immunosuppressive Agents | For treatment of organ transplant recipients, prevention of organ rejection | 23148 |
| Natalizumab | Tysabri ™ | Immunomodulatory Agents | For treatment of multiple sclerosis. | 115334 |
| Nepafenac | | Cyclooxygenase Inhibitors | | |
| Nesiritide | Natrecor ™ | Cardiac drugs | For the intravenous treatment of patients with acutely decompensated congestive heart failure who have dyspnea at rest or with minimal activity. | 118921 |
| Nilotinib | | Tyrosine Kinase Inhibitors | | 530 |
| NS398 | | Cyclooxygenase Inhibitors | | |
| Octreotide | Atrigel ™; Longastatin ™; Sandostatin ™; Sandostatin LAR ™; Sandostatin LAR ™ (Novartis) | Anabolic Agents; Antineoplastic Agents, Hormonal; Gastrointestinal Agents; Hormone Replacement Agents | For treatment of acromegaly and reduction of side effects from cancer chemotherapy | 42687 |
| Omalizumab | Xolair ™ (Genentech Inc) | Anti-Asthmatic Agents; Immunomodulatory Agents | For treatment of asthma caused by allergies | 29596 |
| Oprelvekin | Neumega ™; Neumega ™ (Genetics Institute Inc) | Coagulants; Thrombotics | Increases reduced platelet levels due to chemotherapy | 45223 |
| OspA lipoprotein | LYMErix ™ (SmithKline Beecham) | Vaccines | For prophylactic treatment of Lyme Disease | 95348 |
| OT-551 | (Othera) | Anti-oxidant eyedrop | AMD | |
| Oxytocin | Oxytocin ™ (BAM Biotech); Pitocin ™ (Parke-Davis); Syntocinon ™ (Sandoz) | Anti-tocolytic Agents; Labor Induction Agents; Oxytocics | To assist in labor, elective labor induction, uterine contraction induction | 12722 |
| Palifermin | Kepivance ™ (Amgen Inc) | Antimucositis Agents | For treatment of mucositis (mouth sores) | 138885 |
| Palivizumab | Synagis ™ | Antiviral Agents | For treatment of respiratory diseases casued by respiratory syncytial virus | 63689 |
| Panitumumab | Vectibix ™; Vectibix ™ (Amgen) | Antineoplastic Agents | For the treatment of EGFR-expressing, metastatic colorectal carcinoma with disease progression on or following fluoropyrimidine-, oxaliplatin-, and irinotecan-containing | 134279 |

TABLE 1A-continued

Therapeutic Agent List

| Generic Name | Brands (Companies) | Category | Indication | Molecular Weight |
|---|---|---|---|---|
| | | | chemotherapy regimens. | |
| PDGF inhibitor | (Jerini Ophthalmic); (Ophthotech) | Inhibitors of PDGF | AMD | |
| PEDF (pigment epithelium derived factor) | | | | |
| Pegademase bovine | Adagen ™ (Enzon Inc.) | Enzyme Replacement Agents | For treatment of adenosine deaminase deficiency | 36512 |
| Pegaptanib | Macugen ™ | Oligonucleotide | For the treatment of neovascular (wet) age-related macular degeneration. | 103121 |
| Pegaspargase | Oncaspar ™ (Enzon Inc) | Antineoplastic Agents | For treatment of acute lymphoblastic leukemia | 132.118 |
| Pegfilgrastim | Neulasta ™ (Amgen Inc.) | Anti-Infective Agents; Antineutropenic Agents; Immunomodulatory Agents | Increases leukocyte production, for treatment in non-myeloid cancer, neutropenia and bone marrow transplant | 28518 |
| Peginterferon alfa-2a | Pegasys ™ (Hoffman-La Roche Inc) | Antineoplastic Agents; Antiviral Agents; Immunomodulatory Agents | For treatment of hairy cell leukemia, malignant melanoma, and AIDS-related Kaposi's sarcoma. | 57759 |
| Peginterferon alfa-2b | PEG-Intron (Schering Corp); Unitron PEG ™ | Antineoplastic Agents; Antiviral Agents; Immunomodulatory Agents | For the treatment of chronic hepatitis C in patients not previously treated with interferon alpha who have compensated liver disease and are at least 18 years of age. | 57759 |
| Pegvisomant | Somavert ™ (Pfizer Inc) | Anabolic Agents; Hormone Replacement Agents | For treatment of acromegaly | 71500 |
| Pentoxifylline | | | | |
| Perindozril | | ACE Inhibitors | | |
| Pimecrolimus | | Limus Immunophilin Binding Compounds | | |
| PKC (protein kinase C) inhibitors | | | | |
| POT-4 | Potentia/Alcon | Complement Cascade Inhibitor (Factor C3) | AMD | |
| Pramlintide | Symlin ™; Symlin ™ (Amylin Pharmaceuticals) | | For the mealtime treatment of Type I and Type II diabetes in combination with standard insulin therapy, in patients who have failed to achieve adequate glucose control on insulin monotherapy. | 16988 |
| Proteosome inhibitors | Velcade ™ | | Proteosome inhibitors | |
| Pyrrolidine | | | | |
| Quinopril | | ACE Inhibitors | | |
| Ranibizumab | Lucentis ™ | | For the treatment of patients with neovascular (wet) age-related macular degeneration. | 27043 |
| Rapamycin (siroliums) | (MacuSight) | Limus Immunophilin Binding Compounds | AMD | |

TABLE 1A-continued

Therapeutic Agent List

| Generic Name | Brands (Companies) | Category | Indication | Molecular Weight |
|---|---|---|---|---|
| Rasburicase | Elitek ™; Elitek ™ (Sanofi-Synthelabo Inc); Fasturtec ™ | Antihyperuricemic Agents | For treatment of hyperuricemia, reduces elevated plasma uric acid levels (from chemotherapy) | 168.11 |
| Reteplase | Retavase ™ (Centocor); Retavase ™ (Roche) | Thrombolytic Agents | For lysis of acute pulmonary emboli, intracoronary emboli and management of myocardial infarction | 54732 |
| Retinal stimulant | Neurosolve ™ (Vitreoretinal Technologies) | Retinal stimulants | AMD | |
| Retinoid(s) | | | | |
| Rituximab | MabThera ™; Rituxan ™ | Antineoplastic Agents | For treatment of B-cell non-Hodgkins lymphoma (CD20 positive) | 33078 |
| RNAI (RNA interference of angiogenic factors) | | | | |
| Rofecoxib | Vioxx ™; Ceoxx ™; Ceeoxx ™ (Merck & Co.) | Cyclooxygenase Inhibitors | | |
| Rosiglitazone | | Thiazolidinediones | | |
| Ruboxistaurin | Eli Lilly | Protein Kinase C (PKC)-b Inhibitor | DME, diabetic peripheral retinopathy | 469 |
| Salmon Calcitonin | Calcimar ™; Miacalcin ™ (Novartis) | Antihypocalcemic Agents; Antiosteporotic Agents; Bone Density Conservation Agents | For the treatment of post-menopausal osteoporosis | 57304 |
| Sargramostim | Immunex ™; Leucomax ™ (Novartis); Leukine ™; Leukine ™ (Berlex Laboratories Inc) | Anti-Infective Agents; Antineoplastic Agents; Immunomodulatory Agents | For the treatment of cancer and bone marrow transplant | 46207 |
| SAR 1118 | SARCode | Immunomodulatory Agent | Dry eye, DME, conjunctivitis | |
| SDZ-RAD | | Limus Immunophilin Binding Compounds | | |
| Secretin | SecreFlo ™; Secremax ™, SecreFlo ™ (Repligen Corp) | Diagnostic Agents | For diagnosis of pancreatic exocrine dysfunction and gastrinoma | 50207 |
| Selective inhibitor of the factor 3 complement cascade | | | | |
| Selective inhibitor of the factor 5 complement cascade | | | | |
| Semaxanib | | Tyrosine Kinase Inhibitors | | 238 |
| Sermorelin | Geref ™ (Serono Pharma) | Anabolic Agents; Hormone Replacement Agents | For the treatment of dwarfism, prevention of HIV-induced weight loss | 47402 |
| Serum albumin iodinated | Megatope ™ (IsoTex Diagnostics) | Imaging Agents | For determination of total blood and plasma volumes | 39000 |
| SF1126 | Semafore | Pl3k/mTOR Inhibition | AMD, DME | |
| Sirolimus reformulation (rapamycin) | (MacuSight) | Limus Immunophilin Binding Compounds | AMD | |
| siRNA molecule synthetic, FTP-801i-14 | (Quark Pharmaceuticals) | siRNA molecule synthetic | AMD | |

TABLE 1A-continued

Therapeutic Agent List

| Generic Name | Brands (Companies) | Category | Indication | Molecular Weight |
|---|---|---|---|---|
| Somatropin recombinant | BioTropin ™ (Biotech General); Genotropin ™ (Pfizer); Humatrope ™ (Eli Lilly); Norditropin ™ (Novo Nordisk); Nutropin ™ (Genentech Inc.); NutropinAQ ™ (Genentech Inc.); Protropin ™ (Genentech Inc.); Saizen ™ (Serono SA); Serostim ™; Serostim ™ (Serono SA); Tev-Tropin ™ (GATE) | Anabolic Agents; Hormone Replacement Agents | For treatment of dwarfism, acromegaly and prevention of HIV-induced weight loss | 71500 |
| Squalamine | | | | |
| Streptokinase | Streptase ™ (Aventis Behringer GmbH) | Thrombolytic Agents | For the treatment of acute evolving transmural myocardial infarction, pulmonary embolism, deep vein thrombosis, arterial thrombosis or embolism and occlusion of arteriovenous cannulae | 90569 |
| Sunitinib | | Tyrosine Kinase Inhibitors | | 398 |
| TA106 | Taligen | Complement Cascade Inhibitor (Factor B) | AMD | |
| Tacrolimus | | Limus Immunophilin Binding Compounds | | |
| Tenecteplase | TNKase ™ (Genentech Inc) | Thrombolytic Agents | For treatment of myocardial infarction and lysis of intracoronary emboli | 54732 |
| Teriparatide | Apthela ™; Forsteo ™; Forteo ™; Fortessa ™; Opthia ™; Optia ™; Optiah ™; Zalectra ™; Zelletra ™ | Bone Density Conservation Agents | For the treatment of osteoporosis in men and postmenopausal women who are at high risk for having a fracture. Also used to increase bone mass in men with primary or hypogonadal osteoporosis who are at high risk for fracture. | 66361 |
| Tetrathiomolybdate | | | | |
| Thalidomide | Celgene | Anti-inflammatory, Anti-proliferative | Uveitis | |
| Thyrotropin Alfa | Thyrogen ™ (Genzyme Inc) | Diagnostic Agents | For detection of residueal or recurrent thyroid cancer | 86831 |
| Tie-1 and Tie-2 kinase inhibitors | | | | |
| Toceranib | | Tyrosine Kinase Inhibitors | | 396 |
| Tositumomab | Bexxar ™ (Corixa Corp) | Antineoplastic Agents | For treatment of non-Hodgkin's lymphoma (CD20 positive, follicular) | 33078 |
| TPN 470 analogue | | | | |
| Trastuzumab | Herceptin ™ (Genentech) | Antineoplastic Agents | For treatment of HER2-positive pulmonary breast cancer | 137912 |
| Triamcinolone acetonide | Triesence ™ | Glucocorticoid | DME, For treatment of inflammation of the retina | 435 |

TABLE 1A-continued

Therapeutic Agent List

| Generic Name | Brands (Companies) | Category | Indication | Molecular Weight |
|---|---|---|---|---|
| Troglitazone | | Thiazolidinediones | | |
| Tumistatin | | | | |
| Urofollitropin | Fertinex ™ (Serono S.A.) | Fertility Agents | For treatment of female infertility | 78296 |
| Urokinase | Abbokinase ™; Abbokinase ™ (Abbott Laboratories) | Thrombolytic Agents | For the treatment of 107ulmonary embolism, coronary artery thrombosis and IV catheter clearance | 90569 |
| Vandetanib | | Tyrosine Kinase Inhibitors | | 475 |
| Vasopressin | Pitressin ™; Pressyn ™ | Antidiuretics; Oxytocics; Vasoconstrictor Agents | For the treatment of enuresis, polyuria, diabetes insipidus, polydipsia and oesophageal varices with bleeding | 46800 |
| Vatalanib | | Tyrosine Kinase Inhibitors | | 347 |
| VEGF receptor kinase inhibitor | | | | |
| VEGF Trap | Aflibercept ™ (Regneron Pharmaceuticals, Bayer HealthCare AG) | Genetically Engineered Antibodies | DME, cancer, retinal vein occlusion, choroidal neovascularization, delay wound healing, cancer treatment | 96600 |
| Visual Cycle Modulator ACU-4229 | (Acucela) | Visual Cycle Modulator | AMD | |
| Vitamin(s) | | | | |
| Vitronectin receptor antagonists | | | | |
| Volociximab | Ophthotech | alpha5beta1 Integrin Inhibitor | AMD | |
| XL765 | Exelixis/Sanofi-Aventis | Pl3k/mTOR Inhibition | AMD, DME | |

TABLE 1B

Surfactants

Surfactants include:
Iconic
    Anionic: based on permanent anions (sulfate, sulfonate, phosphate) or pH-dependent anions
    (carboxylate):
        Sulfates:
            Alkyl sulfates: ammonium lauryl sulfate, sodium lauryl sulfate (SDS);
            Alkyl ether sulfates: sodium laureth sulfate, also known as sodium lauryl
            ether sulfate (SLES), sodium myreth sulfate;
        Sulfonates:
            Docusates: dioctyl sodium sulfosucciate;
            Sulfonate fluorosurfactants: perfluorooctanesulfonate (PFOS),
            perfluorobutanesulfonate;
            Alkyl benzne sulfonates;
        Phosphates:
            Alkyl aryl ether phosphate
            Alkyl ether phosphate
        Carboxylates:
            Alkyl carboxylates: Fatty acid salts (soaps): sodium stearate;
            Sodium lauroyl sarcosinate;
            Carboxylate fluorsurfactants: perfluoronoanoate, perfluoroocanoate
            (PFOA OR PFO)
Cationic: based on:
    pH-dependent primary, secondary or tertiary amines become positively charged at pH <10,
    secondary amines become charged at pH <4:
        Octenidine dihydrochloride;
    Permanently charged quaternary ammonium cation:
        Alkyltrimethylammonium sals: cetyl trimthylammonium bromide (CTAB) a.k.a.
        hexadecyl trimethyl ammonium bromide, cetyl trimethylammonium chloride (CTAC);
        Cetylpyridinium chloride (CPC);
        Polyethoxylated tallow amine (POEA);

TABLE 1B-continued

| Surfactants |
|---|
| Benzalkonium chloride (BAC);<br>Benzethonium chloride (BZT);<br>5-Bromo-5-nitro-1,2-dioxane;<br>Dimethyldioctadecylammonium chloride<br>Dioctadecyldimethylammonium bromide (DODAB) . . . |

Zitterionic (amphoteric): based on primary, secondary or tertiary amines or uaternary ammonium cation with:
    Sulfonates:
        CHAPS (3-[(3-Cholamidopropyl)dimethylammonio]-1-propanesulfonate);
        Sultaines: cocamidopropyl hyroxysultaine;
    Carboxylates:
        Amino acids
        Imino acids
        Betaines: cocamidopropyl betaine;
    Phosphates: lecithin . . .
Nonionic
    Fatty alcohol,
    Stearyl alcohol,
    Cetostearyl alcohol (consistently predominantly of cetyl and stearyl alcohols),
    Oleyl alcohol;
    Polyoxyethylene glycol alkyl ethers (Brij): $CH_3-(CH_2)_{10-16}-(O-C_2H_4)_{1-25}-OH$:
        Octaethylene glycol monododecyl ether,
        Pentaethylene glycol monododecyl ether;
    Polyoxypropylene glycol alkyl ethers: $CH_3-(CH_2)_{10-16}-(O-C_2H_6)_{1-25}-OH$:
    Glcoside alkyl ethers: $CH_3-(CH_2)_{10-16}-(O\text{-Glucoside})_{1-3}-OH$:
        Decyl glucoside,
        Lauryl glucoside,
        Octyl glucoside;
    Polyoxyethylene glycol octylphenol ethers: $C_8H_{17}-(C_6H_4)-(O-C_2H_4)_{1-25}-OH$:
        Triton X-100;
    Polyoxyethylene glycol alkyphenol ethers: $C_9H_{19}-(C_6H_4)-(O-C_2H_4)_{1-25}-OH$:
        Nonxynol-9;
    Glycerol alkyl esters:
        Glyceryl laurate
    Polyoxyethylene glycol sorbitn alkyl esters: Polysorbates;
    Sorbitan alkyl esters: Spans;
    Cocamide MEA, cocamide DEA;
    Dodecyl dimethylamine oxide;
    Block copolymers of polyethylene glycol and polypropylene glycol: Poloxamers . . .

TABLE 1C

| Types of Carbohydrates | | | |
|---|---|---|---|
| General: | Aldose • Ketose • Pyranose • Furanose | | |
| Geometry | Cyclohexane conformation • Anomer • Mutarotation | | |
| | Trioses | Ketotriose (Dihydroyacetone) Aldotriose (Glyceraldehyde) | |
| | Tetroses | Ketotetrose (Erythrulose) | |
| | | Ketopentose (Ribulose, Xylulose) | |
| | Pentoses | Aldopentose (Ribose, Arabinose, Xylose, Lyxose) | |
| Monosaccharides | | Deoxy sugar (Deoxyribose) | |
| | | Ketohexose (Psicose, Fructose, Sorbose, Tagatose) | |
| | Hexoses | Aldohexose (Alose, Altrose, Glucose, Mannose, Gulose, Idose, Galactose, Talose) | |
| | | Deoxy sugar (Fucoe, Fuculose, Rhamnose) | |
| | >6 | Heptose (Sedoheptulose) • Octose • Nonose (Neuraminic acid) | |
| | | Disaccharides | Sucrose • Lactose • Maltose • Trehalose • Turanose • Cellobiose |
| | | Trisaccharides | Raffinose • Melezitose • Maltotriose |
| | | Tetrasaccharides | Acarbose • Stachyose |
| | | Other oligosaccharides | Fructooligosaccharide (FOS) • Galactooligosaccharides (GOS) • Mannan-oligosaccharides (MOS) |
| Multiple | | | Glucose/Glucan: Glycogen • Starch (Amylose, Amylopectin) • Cellulose • Dextrin/Dextran • Beta-glucan (Zymosan, Lentinan, Sizofiran) • Maltodextrin |
| | | Polysaccharides | Fructose/Fructan: Inulin • Levan beta 2-6<br>Mannose/Mannan<br>Galactose/alactan<br>N-Acetylglucosemine: Chitin |

The variations set forth in the foregoing description do not represent all variations consistent with the subject matter described herein. Instead, they are merely some examples consistent with aspects related to the described subject matter. Wherever possible, the same reference numbers will be used throughout the drawings to refer to the same or like parts.

Although a few variations have been described in detail above, other modifications or additions are possible. In particular, further features and/or variations can be provided in addition to those set forth herein. For example, the variations described above can be directed to various combinations and sub-combinations of the disclosed features and/or combinations and sub-combinations of several further features disclosed above. In addition, the logic flows and steps for use described herein do not require the particular order shown, or sequential order, to achieve desirable results. Other variations can be within the scope of the claims.

What is claimed is:

1. An aqueous composition comprising:
   (i) a therapeutic agent;
   (ii) a stabilizer having a molecular weight of at least 2 kilodaltons, wherein the molecular weight of the stabilizer is at least 25% of the molecular weight of the therapeutic agent; and
   (iii) a complex comprising the therapeutic agent and the stabilizer;
   wherein the therapeutic agent, the stabilizer, and the complex are in equilibrium in the aqueous composition.

2. The aqueous composition of claim 1, wherein the therapeutic agent, the stabilizer, and the complex are in solution in the aqueous composition.

3. The aqueous composition of claim 1, wherein the therapeutic agent is an antibody or a Fab antibody fragment.

4. The aqueous composition of claim 1, wherein the stabilizer has a plurality of hydrophilic functional groups.

5. The aqueous composition of claim 1, wherein the stabilizer has a molecular weight of at least 5 kilodaltons.

6. The aqueous composition of claim 5, wherein the stabilizer has a molecular weight of at least 10 kilodaltons.

7. The aqueous composition of claim 1, wherein the stabilizer is a metal ion, carboxymethyl cellulose, hydroxyethyl cellulose, hydroxypropyl cellulose, hydroxypropylmethyl cellulose, methylcellulose, chitosan, hyaluronic acid, a histidine polymer, polyethylene oxide, or a combination of two or more thereof.

8. The aqueous composition of claim 1, further comprising a particulate binding agent that is capable of reversibly binding with the therapeutic agent.

9. The aqueous composition of claim 8, wherein the particulate binding agent is non-biodegradable.

10. The aqueous composition of claim 8, wherein the particulate binding agent is a chromatographic binding agent.

11. The aqueous composition of claim 1, further comprising an erodible polymer.

12. The aqueous composition of claim 11, wherein the erodible polymer is polylactic acid, polyglutamic acid, polylactic acid/polyglutamic acid copolymer, polyglycolic acid, or poly(lactide-co-glycolide) copolymer.

13. The aqueous composition of claim 1, further comprising a surfactant.

14. The aqueous composition of claim 13, wherein the surfactant is polysorbate 20, polysorbate 80, an ethylene oxide-propylene oxide block copolymer, an ethoxylated emulsifier, or a combination of two or more thereof.

15. The aqueous composition of claim 1, further comprising a buffer.

16. The aqueous composition of claim 15, wherein the buffer is an acetate buffer, a succinate buffer, a gluconate buffer, a histidine buffer, or a citrate buffer.

* * * * *